(12) United States Patent
Xu et al.

(10) Patent No.: US 11,072,601 B2
(45) Date of Patent: Jul. 27, 2021

(54) µ-OPIOID RECEPTOR AGONIST AND PREPARATION METHOD THEREFOR AND USE THEREOF IN FIELD OF MEDICINE

(71) Applicants: SHANGHAI SYNERGY PHARMACEUTICAL SCIENCES CO., LTD., Shanghai (CN); ZHEJIANG HUAHAI PHARMACEUTICAL CO., LTD., Linhai (CN)

(72) Inventors: Xin Xu, Shanghai (CN); Zhen Zhang, Shanghai (CN); Yunfei Li, Shanghai (CN); Liming Zhang, Shanghai (CN); Fengying Guo, Shanghai (CN); Qingyun Jiang, Shanghai (CN); Dongsheng Li, Shanghai (CN); Linli Zhang, Shanghai (CN); Jinqian Song, Shanghai (CN); Lei Liu, Shanghai (CN); Qiang Liu, Shanghai (CN); Jing Su, Shanghai (CN); Yijin Wang, Shanghai (CN); Jian Ge, Shanghai (CN)

(73) Assignees: SHANGHAI SYNERGY PHARMACEUTICAL SCIENCES CO., LTD., Shanghai (CN); ZHEJIANG HUAHAI PHARMACEUTICAL CO., LTD., Linhai (CN)

( * ) Notice: Subject to any disclaimer, the term of this patent is extended or adjusted under 35 U.S.C. 154(b) by 0 days.

(21) Appl. No.: 16/645,777

(22) PCT Filed: Sep. 17, 2018

(86) PCT No.: PCT/CN2018/105946
§ 371 (c)(1),
(2) Date: Mar. 9, 2020

(87) PCT Pub. No.: WO2019/052557
PCT Pub. Date: Mar. 21, 2019

(65) Prior Publication Data
US 2020/0270230 A1  Aug. 27, 2020

(30) Foreign Application Priority Data
Sep. 18, 2017 (CN) .......................... 201710840488.2

(51) Int. Cl.
*C07D 405/04* (2006.01)
*C07D 405/14* (2006.01)
*C07D 495/04* (2006.01)
*C07D 417/14* (2006.01)

(52) U.S. Cl.
CPC .......... *C07D 405/04* (2013.01); *C07D 405/14* (2013.01); *C07D 417/14* (2013.01); *C07D 495/04* (2013.01)

(58) Field of Classification Search
CPC .. C07D 405/04; C07D 405/14; C07D 495/04; C07D 417/14
USPC .......................................................... 514/301
See application file for complete search history.

(56) References Cited

U.S. PATENT DOCUMENTS 8,835,488 B2 * 9/2014 Yamashita ........... A61K 31/444
514/444
2018/0297988 A1  10/2018 Li et al.

FOREIGN PATENT DOCUMENTS

| CN | 106588899 A | 4/2017 |
| WO | WO-2012129495 A1 | 9/2012 |
| WO | 2017106306 | * 12/2016 |
| WO | WO-2017063509 A1 | 4/2017 |
| WO | WO-2017106547 A1 | 6/2017 |

OTHER PUBLICATIONS

Okude et al., Angewandte Chemie, International Edition (2015), 54(52), 15771-15776.*
Zheng et al., Bioorganic & Medicinal Chemistry Letters (2014), 24(16), 3673-3682.*
Dewire et al., Journal of Pharmacology and Experimental Therapeutics (2013), 344(3), 708-717.*
International Search Report and Written Opinion for Application No. PCT/CN2018/105946, dated Dec. 19, 2018.
Chen, Xiaotao et al. "Structure-Activity Relationships and Discovery of a G Protein Biased µ Opioid Receptor Ligand, [93-Methoxythiophen-2-yl)methyl]({2-[(9R)-9-(pyridin-2-yl)-6-oxaspiro-[4.5]decan-9-yl]ethylpamine (TRV130), for the Treatment of Acute Severe Pain," *Journal of Medicinal Chemistry*, vol. 56, pp. 8019-8031 (2013).
Schneider, S. et al., "How Oliceridine (TRV-130) Binds and Stabilizes µ-Opioid Receptor Conformational State that Selectively Triggers G Protein Signaling Pathways," *Biochemistry*, vol. 55, No. 46, pp. 6456-6466 (2016).
Manglik et al., "Structure-based discovery of opioid analgesics with reduced side effects," *Nature*, vol. 537, pp. 185-206 (2016).
Freye et al., "Development of Opioid Tolerance—Molecular Mechanisms and Clinical Consequences," *Anasthesiol Intensivmed Notfallmed Schmerzther*, vol. 38, pp. 14-26 (2003).
Bohn et al., "Enhanced Morphine Analgesia in Mice Lacking β-Arrestin 2," *Science*, vol. 286, pp. 2495-2498 (1999).
Raehal et al., "Morphine Side Effects in β-Arrestin 2 Knockout Mice," *The Journal of Pharmacology and Experimental Therapeutics*, vol. 314, No. 3, pp. 1195-1201 (2005).
Extended European Search Report for Application No. 18857198.8, dated Mar. 19, 2021.

* cited by examiner

Primary Examiner — Niloofar Rahmani
(74) Attorney, Agent, or Firm — Marshall, Gerstein & Borun LLP

(57) ABSTRACT

Disclosed are a class of µ-opioid receptor agonists and a preparation method therefor and the use thereof in the field of medicine, belonging to the field of medicinal chemistry. The µ-opioid receptor agonists significantly increase the selectivity for a G protein signaling pathway, and not only can exhibit excellent pharmacodynamic effects, but also significantly improve safety.

5 Claims, No Drawings

μ-OPIOID RECEPTOR AGONIST AND PREPARATION METHOD THEREFOR AND USE THEREOF IN FIELD OF MEDICINE

CROSS-REFERENCE TO RELATED APPLICATION

This application is a U.S. national phase of International Application No. PCT/CN2018/105946 filed Sep. 17, 2018, which is based upon and claims priority to Chinese Patent Application No. 201710840488.2 filed Sep. 18, 2017, the entire contents of which are incorporated herein by reference.

TECHNICAL FIELD

The invention belongs to the field of pharmaceutical chemistry, and particularly relates to a class of oxa-spirocyclic small molecule compounds, preparation methods thereof and applications in the field of medicine.

TECHNICAL BACKGROUND

Opioid receptors which belong to one of the members of the G protein-coupled receptor (GPCR) family, are highly expressed in the central nervous system and regulate a series of body behaviors including pain, emotion, stress, etc. through the central nervous system; and there are mainly three subtypes: μ opioid receptor (MOR), δ opioid receptor (DOR), and κ opioid receptor (KOR) (Nature, 2016, 537 (7619): 185). Opioid receptor agonists are currently the most widely used analgesics, among which the agonists acting on μ-opioid receptors (MOR) have the advantages of strong analgesic activity and broad anti-pain effects, and play an irreplaceable role in the treatment of moderate and severe pain.

MOR agonist morphine is a natural product extracted from poppy, having been used as an analgesic for the treatment of acute severe pain for hundreds of years. Since then, a wide variety of morphine derivatives and synthetic compounds such as oxycodone, hydromorphone, oxymorphone, levorphanol, buprenorphine, fentanyl, sufentanil, pethidine and the like as MOR agonists have been developed into clinical analgesics, although these MOR agonists have powerful analgesics effects, all compounds show similar clinical side effects: constipation, nausea, vomiting, sedation, respiratory depression, etc., in addition, the pleasure and physical dependence induced by these MOR agonists are highly prone to addiction and abuse, thus leading to social problems (Journal of Medicinal Chemistry, 2013, 56 (20): 8019-31), and the long-term use of MOR agonists can also lead to analgesic tolerance, which requires dose escalation to control pain, thereby further increasing the clinical side effects mentioned above (Anasthesiol Intensivmed Notfallmed Schmerzther. 2003, 38, 14-26.).

In addition to coupling G protein subunits to activate G protein signaling pathway, most GPCR agonists including MOR agonists can also activate other signaling pathways, wherein the activation of signaling pathways mediated by β-arrestin has a greater impact, β-arrestin can bind to activated GPCR, which results to receptor desensitizing of the GPCR, and stop G protein signaling; β-arrestin can also recruit endocytosis proteins to induce GPCR endocytosis; form complexes with downstream signal molecules of GPCR and activate other signaling molecules, such as MAPK, Src and other kinases. Recent studies have found that β-arrestin pathway is associated with multiple side effects of MOR agonists, such as constipation, respiratory depression, and analgesic tolerance (Science 1999, 286, 2495-2498; J. Pharmacol. Exp. Ther. 2005, 314, 1195-1201). Therefore, the development of a "biased" MOR agonist drug that can selectively activate the G protein signaling pathway may reduce β-arrestin-mediated side effects, which has significant clinical value and social significance.

At present, there are a series of G protein-biased MOR agonists which have been disclosed in patent WO2012129495 filed by Trevena Inc. and WO2017063509 of Jiangsu Hengrui Pharmaceutical Co., Ltd. The compounds disclosed in both patents are oxa-spirocyclic derivatives. The compound of Trevena Inc. has limited selectivity for the G protein signaling pathway (J. Med. Chem. 2013, 56, 8019-8031), and in the patent WO2017063509 of Jiangsu Hengrui Pharmaceutical Co., Ltd., the benzyl position of the aryl group of the compound is formed into a ring, the Emax of the compound is improved, but the selectivity of G protein signaling pathways is still limited. Although a series of patents for G protein-biased MOR agonists have been disclosed, there still needs to develop new MOR agonists with better efficacy, selectivity, and drug metabolism results.

SUMMARY

According to the requirement of the prior art, the inventors have redesigned and synthesized a class of MOR agonists, such compounds have significantly improved selectivity to G protein signaling pathway.

An object of the present invention is to provide a compound represented by the general formula (I), and stereoisomers, tautomers, enantiomers, diastereomers, racemates, and pharmaceutically acceptable salts thereof,

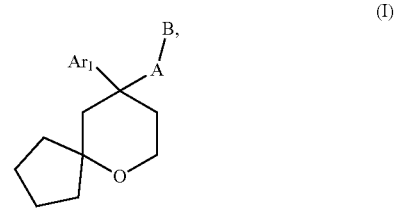

wherein, $Ar_1$ is a substituted or unsubstituted aryl, a substituted or unsubstituted heteroaryl; specifically, $Ar_1$ can be phenyl, pyridyl, a substituted phenyl, or a substituted pyridyl, wherein the phenyl or the pyridyl is optionally substituted by one or more of the following substituents: —$C_{1-3}$ alkyl, —$C_{1-3}$ alkoxy, or halogen;

When A is a —$C_{1-2}$ alkylene or a —$C_{1-3}$ alkyl-substituted —$C_{1-2}$ alkylene, B is —NH—$CH_2$—$Ar_2$, —NH—C(O)—$Ar_2$ or —$NR^1R^2$, wherein $R^1$ and $R^2$ together with the nitrogen atom to which they are attached form a 6-12 membered heteroaryl substituted by T or unsubstituted;

T is —OH, a —$C_{1-3}$ alkyl, a —$C_{1-3}$ alkoxy, a hydroxyl-substituted $C_{1-3}$ alkyl, a halogen-substituted —$C_{1-3}$ alkyl, a halogen-substituted —$C_{1-3}$ alkoxy, halogen, amino, a mono ($C_{1-3}$ alkyl) -amino-, a bis ($C_{1-3}$ alkyl) -amino-, nitrile group, benzyl or phenyl.

Furthermore, when A is a —$C_{1-2}$ alkylene, or a methyl-substituted —$C_{1-2}$ alkylene, —$NR^1R^2$ is

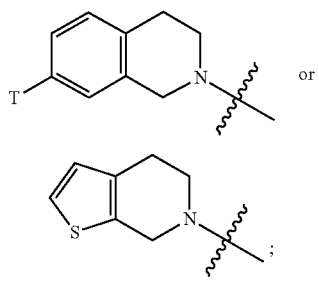

Ar₂ is a substituted or unsubstituted phenyl, a substituted or unsubstituted 5-6 membered heteroaryl, wherein the phenyl or the 5-6 membered heteroaryl is optionally substituted by one or more of the following substituents: —OH, —$C_{1-3}$ alkyl, —$C_{1-3}$ alkoxy, hydroxy-substituted —$C_{1-3}$ alkyl, halogen-substituted —$C_{1-3}$ alkyl, halogen-substituted —$C_{1-3}$ alkoxy, halogen, amino, mono ($C_{1-3}$ alkyl) -amino-, bis ($C_{1-3}$ alkyl) -amino-, nitrile group, benzyl or phenyl;

wherein specifically, Ar₂ can be phenyl, thienyl, imidazolyl, pyridyl or pyrazolyl substituted by the above substituents;

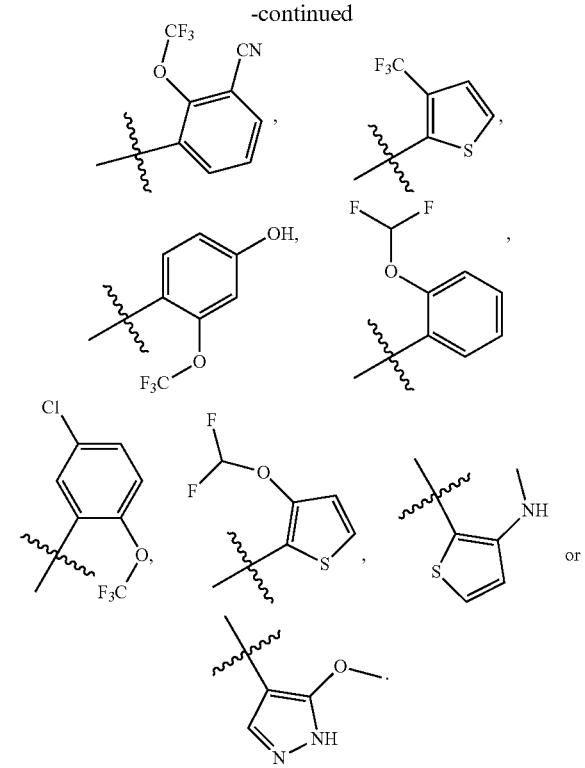

specifically, Ar₂ can also be

In a specific embodiment, the compound represented by the general formula (I) as described above is:

(3-trifluoromethoxybenzyl)-[2-(9-(pyridin-2-yl)-6-oxaspiro[4.5]decan-9-yl)ethyl]amine; (2-chloro-4-trifluoromethoxybenzyl)-[2-(9-(pyridin-2-yl)-6-oxaspiro[4.5]decan-9-yl)ethyl]amine; N-methyl-2-(((2-(9-(pyridin-2-yl)-6-oxaspiro[4.5]decan-9-yl)ethyl)amino)methyl)aniline; (3-chloro-2-methylbenzyl)-[2-(9- pyridin-2-yl)-6-oxaspiro [4.5]decan-9-yl)ethyl]amine; ((3-chloro-thiophen-2-yl)methyl)-[2-(9-(pyridin-2-yl)-6-oxaspiro[4.5]decan-9-yl) ethyl]amine; (4-trifluoromethoxybenzyl)-[2-(9-(pyridin-2-yl)-6-oxaspiro[4.5]decan-9-yl)ethyl]amine; (3,4-dimethylbenzyl)-[2-(9-(pyridin-2-yl)-6-oxaspiro[4.5]decan-9-yl)ethyl]amine; (2,4-dimethylbenzyl)-[2-(9-(pyridin-2-yl)-6-oxaspiro[4.5]decan-9-yl)ethyl]amine; (2-trifluoromethoxybenzyl)-[2-(9-(3-chloro-5-fluoropyridin-2-yl)-6-oxaspiro[4.5]decan-9-yl)ethyl]amine; (2-trifluoromethoxybenzyl)-[2-(9-(3-methyl-5-fluoropyridin-2-yl)-6-oxaspiro[4.5]decan-9-yl)ethyl]amine; (4-bromo-2-trifluoromethoxybenzyl)-[2-(9-(pyridin-2-yl)-6-oxaspiro [4.5]decan-9-yl)ethyl]amine; (4-methyl-2-trifluoromethoxybenzyl)-[2-(9-(pyridin-2-yl)-6-oxaspiro [4.5]decan-9-yl)ethyl]amine; 3-{[(2-(9-(pyridin-2-yl)-6-oxaspiro[4.5]decan-9-yl)ethyl]aminomethyl}-2-trifluoromethoxybenzonitrile; ((3-trifluoromethylthiophen-2-yl)methyl)-[2-(9-(pyridin-2-yl)-6-oxaspiro[4.5]decan-9-yl)ethyl]amine; 4-{[2-(9-(pyridin-2-yl)-6-oxaspiro[4.5] decan-9-yl)ethylamine]methyl}-3-trifluoromethoxyphenol; (2-difluoromethoxybenzyl)-[2-(9-(pyridin-2-yl)-6-oxaspiro [4.5]decan-9-yl)ethyl]amine; (5-chloro-2-trifluoromethoxybenzyl)-[2-(9-(pyridin-2-yl)-6-oxaspiro[4.5]decan-9-yl) ethyl]amine; ((3-difluoromethoxythiophen-2-yl)methyl)-[2-(9-(pyridin-2-yl)-6-oxaspiro[4.5]decan-9-yl)ethyl]amine; 2-[2-(9-(pyridin-2-yl)-6-oxaspiro[4.5]decan-9-yl)ethyl]-7-trifluoromethyl-1,2,3,4-tetrahydroisoquinoline; 7-methoxy- 2-[2-(9-pyridin-2-yl-6-oxa-spiro[4.5]decan-9-yl)-ethyl]-1,2,3,4-tetrahydroisoquinoline; {2-[9-(5-fluoro-pyridin-2-yl)-6-oxa-spiro[4.5] decan-9-yl]-ethyl}-(2-(trifluoromethoxy)-benzyl)-amine; (2-trifluoromethoxyphenmethyl)-[2-(9-pyridin-2-yl-6-oxa-spiro[4.5]decan-9-yl)-ethyl]-amine; 6-[2-(9-pyridin-2-yl-6-oxa-spiro[4.5]decan-9-yl)-ethyl]-4,5,6,7-tetrahydro-thieno[2,3-c]pyridine; 3-methylamino-thiophen-2-carboxylic acid[2-(9-pyridin-2-yl-6-oxa-spiro[4.5]decan-9-yl)-ethyl]amide; [(5-methoxy-1H-pyrazol-4-yl)methyl]-[2-(9-(pyridin-2-yl)-6-oxaspiro[4.5]decan-9-yl) ethyl]amine; ((3-methoxythiophen-2-yl)methyl)-2-(9-(pyridin-2-yl)-6-oxaspiro[4.5]decan-9-yl)propyl]-1-amine; ((3-methoxythiophen-2-yl)methyl)-1-(9-(pyridin-2-yl)-6-oxaspiro[4.5]decan-9-yl)propyl]-2-amine; (3-bromo-2-trifluoromethoxyphenmethyl)-[2-(9-pyridin-2-yl-6-oxa-spiro[4.5]decan-9-yl)-ethyl]-amine; {2-[9-(5-fluoro-pyridin-2-yl)-6-oxa-spiro[4.5]decan-9-yl]-ethyl}-(2-(difluoromethoxy)-benzyl)-amine; {2-[9-(5-fluoro-pyridin-2-yl)-6-oxa-spiro[4.5]decan-9-yl]-ethyl}-((3-chlorothiophene-2-yl)-methyl)-amine; {2-[9-(5-fluoro-pyridin-2-yl)-6-oxa-spiro[4.5]decan-9-yl]-ethyl}-(3,4-dimethyl-benzyl)-amine; {2-[9-(5-fluoro-pyridin-2-yl)-6-oxa-spiro[4.5]decan-9-yl]-ethyl}-(3-chloro-2-methyl-benzyl)-amine; or {2-[9-(5-fluoro-pyridin-2-yl)-6-oxa-spiro[4.5]decan-9-yl]-ethyl}-((3-difluoromethoxythiophen-2-yl)-methyl)-amine.

As describe above, the present invention also comprises pharmaceutically acceptable salts and stereoisomers of the compounds of formula (I).

The pharmaceutically acceptable salts include inorganic alkali salts such as sodium salts, potassium salts, calcium salts or aluminum salts; organic alkali salts such as lysine salt, arginine salt, triethylamine salt, and dibenzylamine salts, piperidine salt and other pharmaceutically acceptable organic amine salts.

When the molecule of the compound of the present invention contains at least one salifiable nitrogen atom, the compound of the present invention can be converted into the corresponding salt by reacting with the corresponding organic acid or inorganic acid in an organic solvent (such as acetonitrile, tetrahydrofuran). Typical organic acids include oxalic acid, tartaric acid, maleic acid, succinic acid, and citric acid; typical inorganic acids include nitric acid, hydrochloric acid, sulfuric acid, and phosphoric acid, preferably nitric acid.

When the compound of the present invention has one or more asymmetric carbon atoms, they can exist in the following forms: optically pure enantiomers, pure diastereomers, mixture of enantiomers, mixture of diastereoisomers, racemic mixture of enantiomers, racemates or mixture of racemate. All possible isomers, stereoisomers of the compound of formula (I) and mixtures thereof are also within the scope of the invention.

The invention relates to a method for preparing the compound represented by general formula (I), wherein: when A is a —$C_{1-2}$ alkylene, and B is —NH—$CH_2$—$Ar_2$, the synthesis route is as shown in Scheme 1:

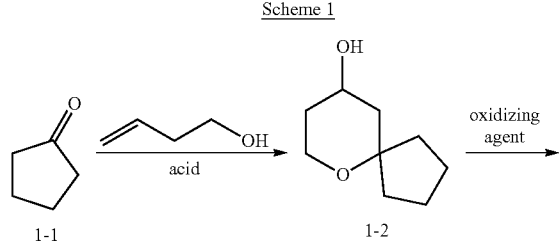

Scheme 1

Wherein Ar1 and Ar2 are as defined in claim 1, 2, 3, 4 or 5, the acid is preferably sulfuric acid, hydrochloric acid, phosphoric acid, trifluoromethanesulfonic acid, hydrobromic acid or a combination thereof; the oxidizing agent is preferably pyridinium chlorochromate (PCC), pyridinium dichromate (PDC), or a combination thereof; the aryl Grignard reagent is preferably aryl magnesium bromide, aryl magnesium chloride, or a combination thereof; the base is preferably potassium hydroxide, sodium hydroxide or a combination thereof; the reducing agent 1 is preferably lithium aluminum tetrahydride, borane tetrahydrofuran, borane dimethyl sulfide or a combination thereof; and the reducing agent 2 is preferably sodium borohydride, potassium borohydride, sodium triacetoxyborohydride, sodium cyanoborohydride or a combination thereof;

When A is a $C_{1-3}$ alkyl-substituted —$C_{1-2}$ alkylene, and B is —NH—$CH_2$—$Ar_2$, the synthesis route is as shown in Scheme 2 or Scheme 3,

Scheme 2

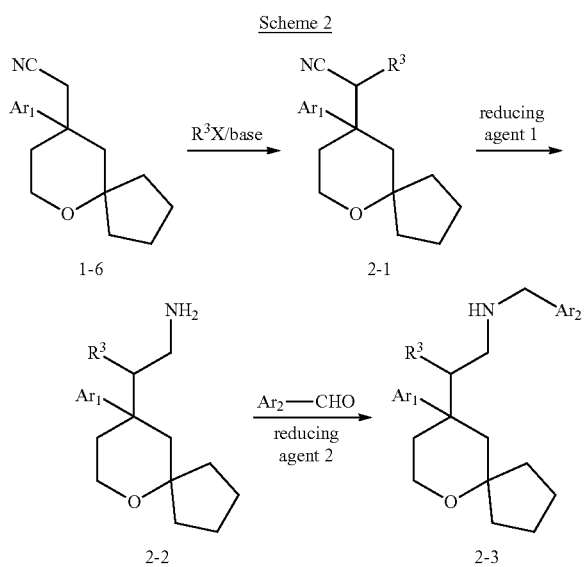

Wherein Ar1 and Ar2 are as defined in claim 1, 2, 3 or 4, R3 is C1-3 alkyl, and the base is preferably sodium hydride, lithium diisopropylamide, butyllithium, potassium tert-butoxide, sodium ethoxide, lithium hexamethyldisilazide, potassium hexamethyldisilazide, or a combination thereof; the reducing agent 1 is preferably lithium aluminum tetrahydride, borane tetrahydrofuran, borane dimethyl sulfide or a combination thereof; and the reducing agent 2 is preferably sodium borohydride, potassium borohydride, sodium triacetoxyborohydride, sodium cyanoborohydride or a combination thereof;

Scheme 3

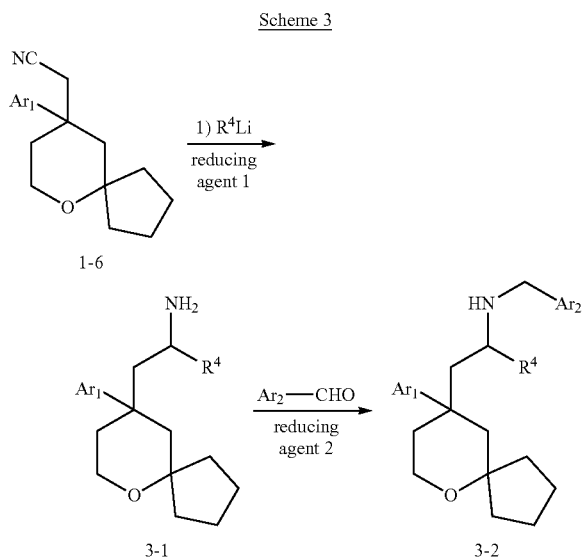

Wherein Ar1 and Ar2 are as defined in claim 1, 2, 3 or 4, R4 is C1-3 alkyl, and the reducing agent 1 is preferably lithium aluminum tetrahydride, borane tetrahydrofuran, borane dimethyl sulfide or a combination thereof; and the reducing agent 2 is preferably sodium borohydride, potassium borohydride, sodium triacetoxyborohydride, sodium cyanoborohydride or a combination thereof;

When A is a $-C_{1-2}$ alkylene, and B is $-NH-C(O)-Ar_2$, the synthesis route is as shown in Scheme 4,

Scheme 4

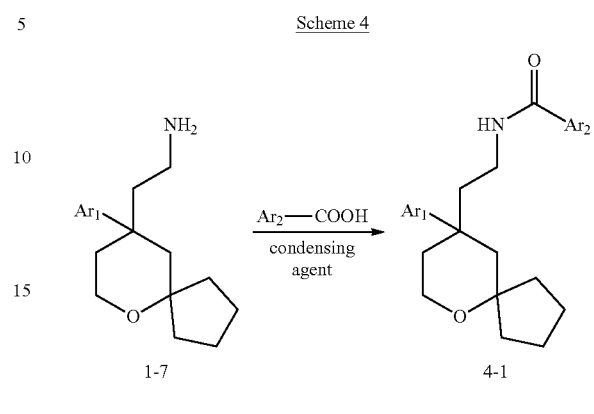

Wherein Ar1 and Ar2 are as defined in claim 1, 2, 3 or 4, preferably the condensing agent is 1-ethyl-(3-dimethylaminopropyl) carbodiimide hydrochloride (EDCI)/1-hydroxybenzotriazole (HOBT), dicyclohexylcarbodiimide (DCC), 2-(7-azabenzotriazol-1-yl)-N,N,N',N'-tetramethyluronium hexafluorophosphate (HATU) or a combination thereof;

When A is a $-C_{1-2}$ alkylene, and B is $-NR^1R^2$, the synthesis route is as shown in Scheme 5,

Scheme 5

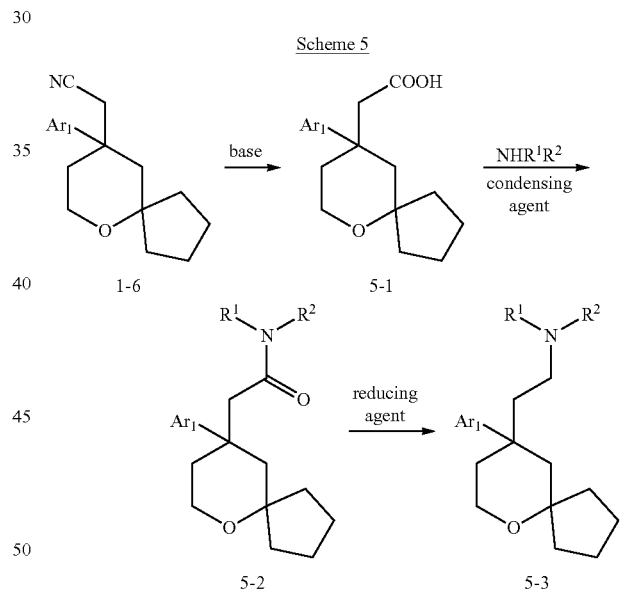

Wherein $Ar_1$, $R^1$, and $R^2$ are as defined in claim 1, 2, 3, or 4, the base is preferably sodium hydroxide, potassium hydroxide, or a combination thereof, and the condensing agent is preferably 1-ethyl-(3-dimethylaminopropyl)carbodiimide hydrochloride (EDCI)/1-hydroxybenzotriazole (HOBT), dicyclohexylcarbodiimide (DCC), 2-(7-azabenzotriazol-1-yl)-N,N,N',N'-tetramethyluronium hexafluorophosphate (HATU) or a combination thereof, and the reducing agent is preferably lithium aluminum tetrahydride, borane tetrahydrofuran, borane dimethyl sulfide or a combination thereof.

The present invention relates to a method for preparing a compound represented by general formula (I) or pharmaceutically acceptable salts thereof, wherein when A is a —$C_{1-2}$ alkylene and B is —NH—$CH_2$—$Ar_2$, the synthesis route is summarized as follows (Scheme 1'):

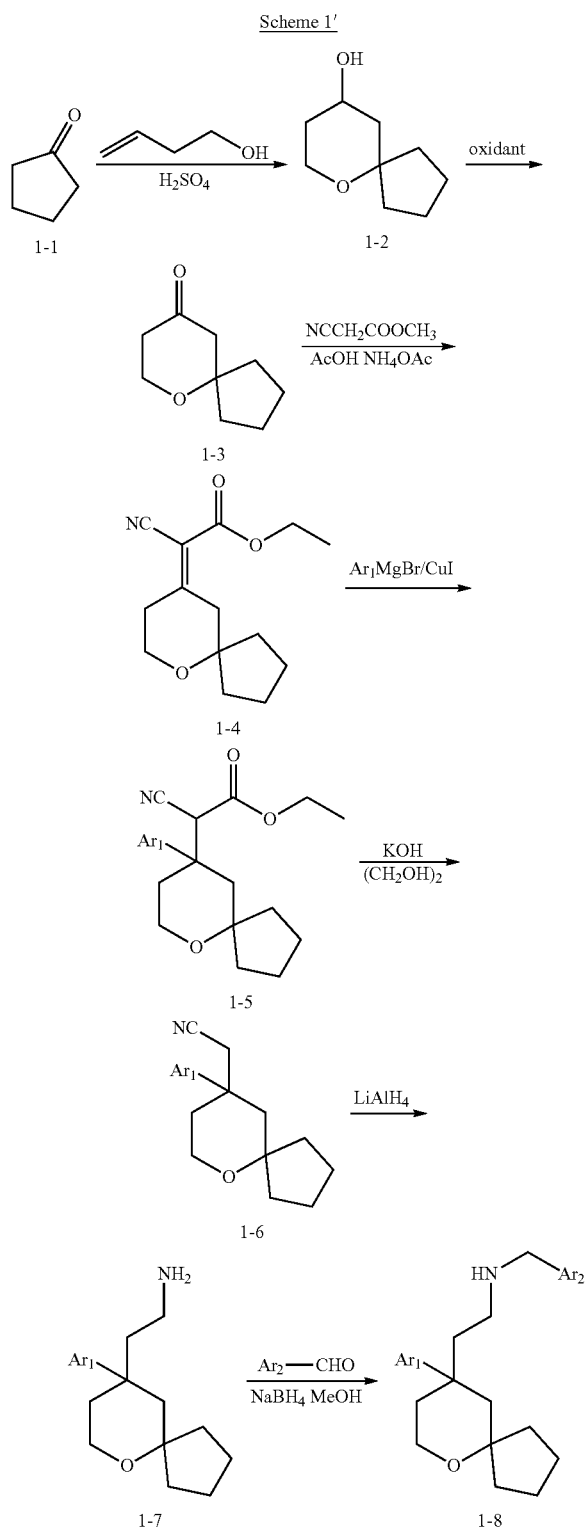

Wherein $Ar_1$ and $Ar_2$ are as defined above.

Cyclopentanone and 3-buten-1-ol form spiro intermediate 1-2 under the condition of sulfuric acid, the 1-2 is oxidized by a suitable oxidant to prepare compound 1-3, the 1-3 is reacted with ethyl cyanoacetate to obtain intermediate 1-4, the 1-4 is reacted with the Grignard reagent to obtain compound 1-5, the 1-5 is hydrolyzed and decarboxylated under a basic condition, and the cyano group is further reduced to obtain alkylamine 1-7, the 1-7 is reduced and aminated with a corresponding aldehyde to obtain final compound 1-8.

The present invention relates to a method for preparing a compound represented by general formula (I) or pharmaceutically acceptable salts thereof, wherein when A is a —$C_{1-3}$ alkyl-substituted —$C_{1-2}$ alkylene, B is —NH—$CH_2$—$Ar_2$, the synthesis route is summarized as follows (Scheme 2' and Scheme 3'):

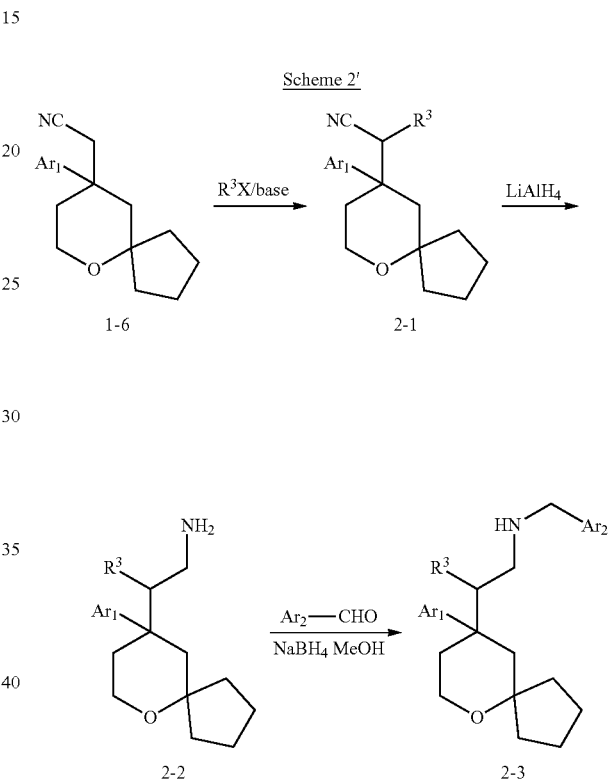

Wherein $Ar_1$ and $Ar_2$ are as defined above, $R^3$ is a $C_{1-3}$ alkyl.

After the reaction of compound 1-6 with haloalkane $R^3X$ under the action of a base, the cyano group is reduced to obtain compound 2-2, and the 2-2 is reduced and aminated with a corresponding aldehyde to obtain final compound 2-3.

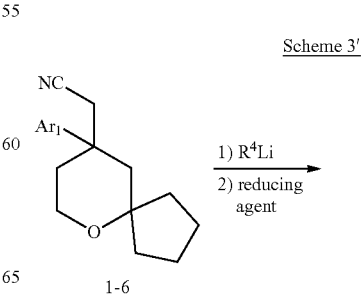

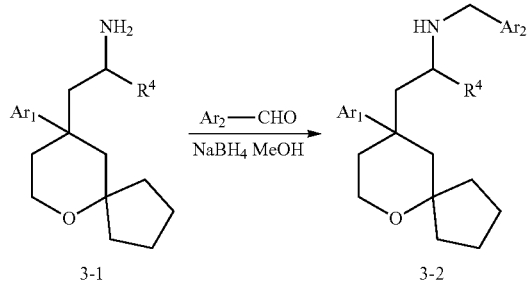

Wherein $Ar_1$ and $Ar_2$ are as defined above, $R^4$ is a $C_{1-3}$ alkyl.

The compound 1-6 is reacted with alkyl lithium compound $R^4Li$, then is reduced by a reducing agent to obtain intermediate 3-1, the 3-1 is reduced and aminated with a corresponding aldehyde to obtain final compound 3-2.

The present invention relates to a method for preparing a compound represented by general formula (I) or pharmaceutically acceptable salts thereof, wherein when A is —$C_{1-2}$ alkylene and B is —NH—C(O)—$Ar_2$, the synthesis route is summarized as follows (Scheme 4'):

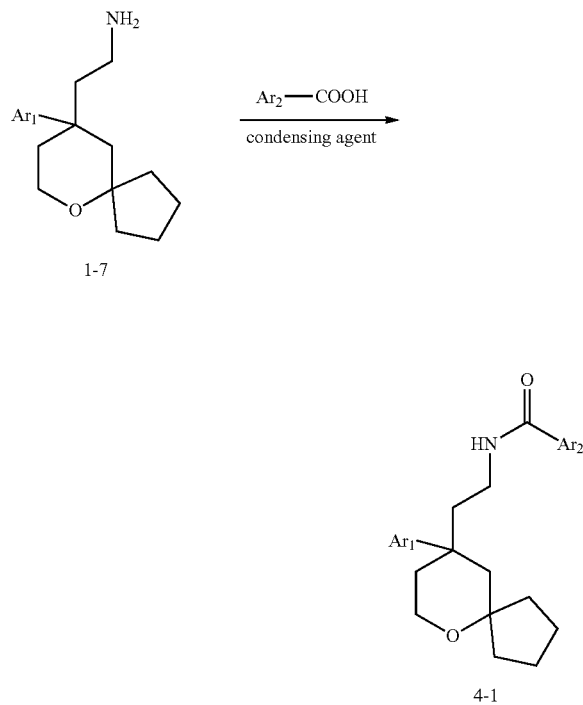

Wherein $Ar_1$ and $Ar_2$ are as defined above.

The intermediate 1-7 reacts with a corresponding carboxylic acid $Ar_2COOH$ under the action of a condensing agent to produce compound 4-1.

The present invention relates to a method for preparing a compound represented by general formula (I) or pharmaceutically acceptable salts thereof, wherein when A is —$C_{1-2}$ alkylene, B is —$NR^1R^2$, the synthesis route is summarized as follows (Scheme 5'):

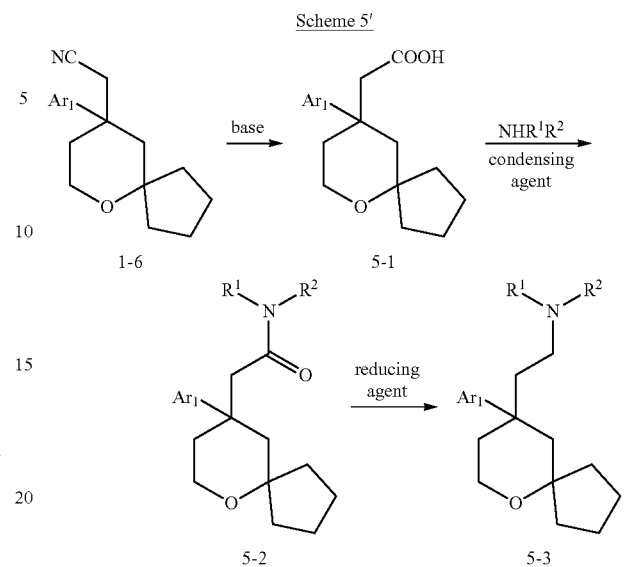

Wherein $Ar_1$, $R^1$, $R^2$ are as defined above.

The intermediate 1-6 is hydrolyzed under alkaline conditions to prepare acid 5-1, and the 5-1 is condensed with a corresponding amine under the condition of a condensing agent, and the final product 5-3 is obtained after a reduction.

The present invention also provides a pharmaceutical composition comprising at least one of the compounds described above and optionally one or more medically acceptable carriers and/or additives.

The pharmaceutical composition provided by the present invention can be prepared into any forms, such as granule, powder, tablet, coated tablet, capsule, pill, syrup, drop, solution, suspension and emulsion, or sustained-release preparation of the active ingredient, wherein examples of the capsule includes hard or soft gelatin capsules, the granule and powder may be in non-effervescent or effervescent forms.

The pharmaceutical composition of the invention may further include one or more medically or physiologically acceptable carriers, such carriers will be suitably formulated for ease of administration. For example, medically or physiologically acceptable carriers may be saline, hot-pressed water, Ringer's solution, buffered saline, glucose, maltodextrin, glycerol, ethanol, and mixtures thereof.

The pharmaceutical composition of the present invention may also include medically or physiologically acceptable additives such as diluents, lubricants, adhesives, glidants, disintegrants, sweeteners, flavoring agents, wetting agents, dispersants, surfactants, buffered saline, coating agents, foaming agents, preservatives, stabilizers or fragrances.

Examples of diluent that can be used include, but are not limited to, lactose, sucrose, starch, kaolin, salt, mannitol and dicalcium phosphate; examples of lubricant include, but are not limited to, talc, starch, stearate of magnesium or calcium, lycopodium and stearic acid; examples of adhesive include, but are not limited to, microcrystalline cellulose, tragacanth, glucose solution, acaciae mucilago, gelatin solution, sucrose, and starch paste; examples of glidant include, but are not limited to, colloidal silicon dioxide; examples of disintegrant include, but are not limited to, cross-linked sodium carboxymethyl cellulose, sodium starch glycolate, alginic acid, corn starch, potato starch, bentonite, methyl cellulose, agar, and carboxymethyl cellulose; examples of sweetener include, but are not limited to, sucrose, lactose, mannitol, and artificial sweeteners, such as sodium cyclamate and saccharin, and any number of spray-dried flavoring agents; examples of flavoring agent include, but are not limited to, natural flavoring agents extracted from plants, such as fruits, and better-tasting compounds, such as but not limited to mint and methyl salicylate; examples of wetting agent include, but are not limited to, propylene glycol monostearate, sorbitan monooleate, diethylene glycol monolaurate and polyoxyethylene lauryl ether.

The surfactant may be selected from detergents, ethoxylated castor oil, pegylated glycerides, acetylated monoglycerides, sorbitan fatty acid esters, poloxamers such as 188 and 407, polyoxyethylene sorbitan fatty acid esters, polyoxyethylene derivatives such as alkylated and alkoxylated derivatives (Tween, such as Tween-20, or Tween-80), monoglycerides or their ethoxylated derivatives, diglycerides or their polyoxyethylene derivatives, glycerol, cholic acid or derivatives thereof, lecithin, alcohols and phospholipids, glycerophospholipids (lecithin, brain phospholipid, phosphatidylserine), glyceroglycolipid (galactopyranoside), sphingomyelin, and glycosphingolipid (ceramide, ganglioside), DSS (docusate sodium), docusate calcium, docusate potassium, SDS (sodium lauryl sulfate), dipalmitoyl phosphatidic acid, sodium caprylate, bile acid and salts thereof, and glycine or taurine conjugate, ursodeoxycholic acid, sodium cholate, sodium deoxycholate, sodium taurocholate, sodium glycocholate, N-hexadecyl-N, N-dimethyl-3-ammonium-1-propanesulfonate, anionic (alkyl-aryl-sulfonate) monovalent surfactant, palmitoyl lysophosphatidyl-L-serine, lysophospholipids (for example, 1-acyl-sn-glycerol-3-phosphate of ethanolamine, choline, serine or threonine), alkyl, alkoxy (alkyl ester), alkoxy (alkyl ether-derivative) of lysophosphatidylcholine and alkoxy (alkyl ether-derivative) of phosphatidylcholine, such as dodecanoyl derivatives and myristoyl derivatives of lysophosphatidylcholine, dipalmitoyl phosphatidylcholine, and modification of polar head groups, namely choline, ethanolamine, phosphatidic acid, serine, threonine, glycerol, inositol, and positively charged DODAC, DOTMA, DCP, BISHOP, lysophosphatidylserine and lysophosphatidylthreonine, zwitterionic surfactants (such as N-alkyl-N, N-dimethylammonium-1-propanesulfonate, 3-cholamido-1-propyldimethyl ammonium-1-propanesulfonate, dodecylphosphocholine, myristoyl lysophosphatidylcholine, egg lysolecithin), cationic surfactants (quarternary ammonium bases) (for example, hexadecyltrimethylammonium bromide, cetylpyridinium chloride), non-ionic surfactants, polyethyleneoxide/polypropyleneoxide block copolymers (Pluronics/Tetronics, Triton X-100, dodecyl β-D-glucopyranoside) or polymer surfactants (Tween-40, Tween-80, Brij-35), fusidic acid derivatives (such as sodium taurodihydrofusidate, etc.), C6-C12 long-chain fatty acids and salts thereof (e.g., oleic acid and caprylic acid), acylcarnitines and derivatives, Nα-acylated derivatives of lysine, arginine or histidine, or side-chain acylated derivatives of lysine or arginine, Nα-acylated derivatives of dipeptides comprising any combination of lysine, arginine or histidine and a neutral or acidic amino acid, Nα-acylated derivatives of tripeptides comprising any combination of a neutral amino acid and two charged amino acids, or mixtures thereof.

The buffered saline can be selected from sodium acetate buffer, sodium carbonate buffer, citrate buffer, glycylglycine buffer, histidine buffer, glycine buffer, lysine buffer, and arginine buffer, sodium phosphate buffer, and tris(hydroxymethyl)-aminomethane buffer, or a mixture thereof, and may also be glycylglycine buffer, sodium phosphate buffer, or a mixture thereof.

The preservative may be selected from phenol, m-cresol, methylparaben, propylparaben, 2-phenoxyethanol, butylparaben, 2-phenylethanol, benzyl alcohol, and chlorbutanol, thiomerosal, or a mixture thereof, may also be phenol or m-cresol.

The preservative exists at a concentration of about 0.1 mg/ml to about 50 mg/ml, at a concentration of about 0.1 mg/ml to about 25 mg/ml, or at a concentration of about 0.1 mg/ml to about 10 mg/ml.

The above stabilizer includes but are not limited to polyethylene glycol (such as PEG3350), polyvinyl alcohol (PVA), polyvinylpyrrolidone, carboxymethyl cellulose, different salts (such as sodium chloride), L-glycine, L-histidine, imidazole, arginine, lysine, isoleucine, aspartic acid, tryptophan, and threonine or any mixtures thereof.

The invention also provides the use of the above-mentioned compounds or pharmaceutical compositions in the preparation of medicaments for the prevention and/or treatment of the related diseases mediated by MOR receptor agonists.

The related diseases mediated by MOR receptor agonists as described above include, but are not limited to, pain, inflammation, immune dysfunction, esophageal reflux, neurological and psychiatric disorders, or respiratory diseases.

The pain mentioned above includes, but is not limited to, traumatic pain, neuropathic pain, inflammatory pain, visceral pain, migraine, and cancer-related pain. The pain mentioned above may be postoperative pain, pain caused by cancer, neuropathic pain, pain caused by trauma, or pain caused by inflammation.

The compound or pharmaceutical compositions provided by the present invention can also be used in urinary and reproductive disorders, drug and alcohol abuse, gastritis or diarrhea. Accordingly, the present invention provides the use of the compounds or pharmaceutical compositions provided by the present invention in the preparation of medicaments for improving urinary and reproductive disorders, drug and alcohol abuse, gastritis or diarrhea.

The amount and frequency of administration of the compounds described herein and/or pharmaceutical salts thereof will be adjusted according to the judgment of the attending clinician by considering such factors as age, disorder and patient size, and the severity of the symptoms being treated. Generally, it is considered that an effective amount may be 0.001 mg/kg to 10 mg/kg body weight, and may specifically be 0.01 mg/kg to 1 mg/kg body weight.

In some embodiments, the pharmaceutical preparation is in the form of a unit dose. The amount of active compounds in a unit dose of the formulation can be varied or adjusted according to the specific application: from about 0.01 mg to about 1000 mg, from about 0.01 mg to about 750 mg, from about 0.01 mg to about 500 mg, or from about 0.01 mg to about 250 mg.

The compounds of the present invention remarkably improve the selectivity to the G protein signaling pathway, and not only can show excellent medicinal effects, but also have significantly improved safety.

EMBODIMENTS

Unless stated to the contrary, some of the terms used herein have the following meanings:

Herein, the term "—$C_{1-3}$ alkyl" includes an alkyl containing from 1 to 3 carbon atoms.

Herein, the term "aryl" includes 5- and 6-membered monocyclic aromatic groups, which may contain 0-4 heteroatoms, such as benzene, phenyl, pyrrole, furan, thiophene, thiazole, isothiazole, imidazole, triazole, tetrazole, pyrazole, azole, isoxazole, pyridine, pyrazine, pyridazine, and pyrimidine, etc. In addition, the term "aryl" also includes polycyclic aryl, such as tricyclic, bicyclic, such as naphthalene, benzoxazole, benzodioxolyl, benzothiazole, benzimidazole, benzothiophene, methylenedioxyphenyl, quinoline, isoquinoline, naphthyridine, indole, benzofuran, purine, benzofuran, deazapurine, or indolizine. Such an aryl with heteroatom is also referred to "aryl heterocycle", "heterocycle", "heteroaryl" or "heteroaromatic group".

Typical heteroaryl includes 2- or 3-thienyl; 2- or 3-furyl; 2- or 3-pyrrolyl; 2-, 4- or 5-imidazolyl; 3-, 4- or 5-pyrazolyl; 2-, 4- or 5-thiazolyl; 3-, 4- or 5-isothiazolyl; 2-, 4- or 5-oxazolyl; 3-, 4- or 5- isoxazolyl; 3- or 5-1,2,4-triazolyl; 4- or 5-1,2,3-triazolyl; tetrazolyl; 2-, 3- or 4-pyridyl; 3- or 4-pyridazinyl; 3-, 4- or 5-pyrazinyl; 2-pyrazinyl; 2-, 4- or 5-pyrimidinyl.

The term "heteroaryl" as used herein also refers to a group in which a heteroaromatic ring is fused with one or more aryl, cycloaliphatic, or heterocyclic rings, wherein the linking group or the linking point is located at the heteraromatic ring. Examples thereof include, but are not limited to, 1-, 2-, 3-, 5-, 6-, 7-, or 8-indolizinyl; 1-, 3-, 4-, 5-, 6-, or 7-isoindolyl; 2-, 3-, 4-, 5-, 6-, or 7-indolyl; 2-, 3-, 4-, 5-, 6-, or 7-indazolyl; 2-, 4- , 5-, 6-, 7- or 8-purinyl; 1-, 2-, 3-, 4-, 6-, 7-, 8- or 9-quinolizinyl; 2-, 3-, 4- , 5-, 6-, 7- or 8-quinolinyl; 1-, 3-, 4-, 5-, 6-, 7- or 8-isoquinolinyl; 1-, 4-, 5-, 6-, 7- or 8-phthalazinyl; 2-, 3-, 4-, 5- or 6-naphthyridinyl; 2-, 3-, 5-, 6-, 7- or 8-quinazolinyl; 3-, 4-, 5-, 6-, 7- or 8-cinnolinyl; 2-, 4-, 6- or 7-pteridyl; 1-, 2-, 3-, 4-, 5-, 6-, 7- or 8-4aH carbazolyl; 1-, 2-, 3-, 4-, 5-, 6-, 7- or 8-carbazolyl; 1-, 3-, 4-, 5-, 6-, 7-, 8- or 9-carbolinyl; 1-, 2-, 3-, 4-, 6-, 7-, 8-, 9- or 10-phenanthridinyl; 1-, 2-, 3-, 4-, 5-, 6-, 7-, 8- or 9-acridinyl; 1-, 2-, 4-, 5-, 6-, 7-, 8- or 9- perimidinyl; 2-, 3-, 4-, 5-, 6-, 8-, 9- or 10- phenathrolinyl; 1-, 2-, 3-, 4-, 6-, 7-, 8- or 9-phenazinyl; 1-, 2-, 3-, 4-, 6-, 7-, 8-, 9- or 10-phenothiazinyl; 1-, 2-, 3-, 4-, 6-, 7-, 8-, 9- or 10-phenazinyl; 2-, 3-, 4- , 5-, 6- or 1-, 3-, 4-, 5-, 6-, 7-, 8-, 9- or 10- benzoisoqinolinyl; 2-, 3-, 4- or thieno[2,3-b]furanyl; 2-, 3-, 5-, 6-, 7-, 8-, 9-, 10- or 11-7H- pyrazino [2,3-c] carbazolyl; 2-, 3-, 5-, 6- or 7-2H-furo[3,2-b]-pyranyl; 2-, 3-, 4-, 5-, 7- or 8-5H-pyrido [2,3-d]-o- oxazinyl; 1-, 3- or 5-1H-pyrazolo [4,3-d]-oxazolyl; 2-, 4- or 5-4H-imidazo[4,5-d]thiazolyl; 3-, 5- or 8-pyrazino [2,3-d] pyridazinyl; 2-, 3-, 5- or 6-imidazo[2, 1-b]thiazolyl; 1-, 3-, 6-, 7-, 8- or 9-furo[3,4-c] cinnolinyl; 1-, 2-, 3-, 4-, 5-, 6-, 8-, 9-, 10, or 11-4H-pyrido[2,3-c]carbazolyl; 2-, 3-, 6-, or 7-imidazo[1,2-b][1,2,4]triazinyl; 7-benzo[b]thienyl; 2-, 4-, 5-, 6- or 7- benzoxazolyl; 2-, 4-, 5-, 6- or 7-benzimidazolyl; 2-, 3-, 4-, 5-, 6- or 7-benzothiazolyl; 1-, 2-, 4-, 5-, 6-, 7-, 8- or 9-benzoxapinyl; 2-, 4-, 5- 6-, 7- or 8-benzoxazinyl; 1-, 2-, 3-, 5-, 6-, 7-, 8-, 9-, 10- or 11-1H-pyrrolo[1,2-b][2]benzoazecyl. Typical fused heteroaryl includes 2-, 3-, 4-, 5-, 6-, 7- or 8-quinolinyl; 1-, 3-, 4-, 5-, 6-, 7- or 8-isoquinolinyl; 2-, 3-, 4-, 5-, 6-, or 7-indolyl; 2-, 3-, 4-, 5-, 6-, or 7-benzo[b]thienyl; 2-, 4-, 5-, 6-, or 7-benzoxazolyl; 2-, 4-, 5-, 6-, or 7-benzimidazolyl; 2-, 4-, 5-, 6- or 7-benzothiazolyl.

The aromatic ring of "aryl" or "heteroaryl" used herein may be substituted at one or more ring positions with the substituents as described above, such as halogen, hydroxy, alkoxy, alkylcarbonyloxy, arylcarbonyloxy, alkoxycarbonyloxy, aryloxycarbonyloxy, hydroxycarbonyl, alkylcarbonyl, alkylaminocarbonyl, arylalkylaminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonate, cyano, amino (including alkylamino, dialkylamino, arylamino, diarylamino and alkylarylamino), acylamino (including alkylcarbonylamino, arylcarbonylamino, carbamoyl and ureido), amidino, imino, mercapto, alkylthio, arylthio, hydroxythiocarbonyl, sulfate, alkylsulfinyl, sulfonate, sulfamoyl, sulfonylamino, nitro, trifluoromethyl, cyano, azido, heterocyclyl, alkylaryl, or aromatic groups or heteroaromatic groups, wherein aryl groups can also be fused or bridged with non-aromatic alicyclic or heterocyclic rings to form a polycycle (e.g., tetralin).

Herein, the term "alkoxy" includes substituted and unsubstituted alkyl which is covalently attached to an oxygen atom. Examples of alkoxy include methoxy, ethoxy, isopropyloxy, propoxy, butoxy and amoxy. Examples of substituted alkoxy includes haloalkoxy. The alkoxy can be substituted by the following groups: alkenyl, alkynyl, halogen, hydroxy, alkylcarbonyloxy, arylcarbonyloxy, alkoxycarbonyloxy, aryloxycarbonyloxy, hydroxycarbonyl, alkylcarbonyl, arylcarbonyl, alkoxycarbonyl, aminocarbonyl, alkylaminocarbonyl, dialkylaminocarbonyl, alkylthiocarbonyl, phosphate, cyano, amino (including alkylamino, dialkylamino, arylamino, diarylamino and alkylarylamino), acylamino (including alkylcarbonylamino, arylcarbonylamino, carbamoyl, and ureido), amidino, imino, mercapto, alkylthio, arylthio, hydroxythiocarbonyl, alkylsulfinyl, sulfo, sulfamoyl, sulfonylamino, nitro, trifluoromethyl, cyano, azido, heterocyclyl, alkylaryl or an aromatic group.

The present invention is further described in combination with the following embodiments, but these embodiments do not limit the scope of the present invention.

Example 1: Preparation of (3-trifluoromethoxybenzyl)-[2-(9-(pyridin-2-yl)-6-oxaspiro[4.5]decan-9-yl)ethyl]amine (H01)

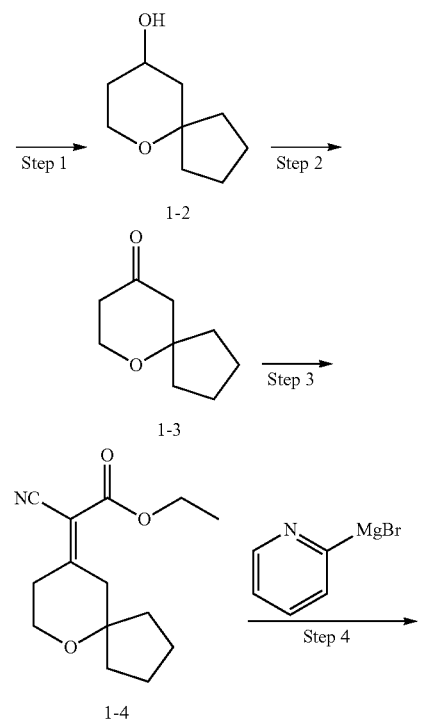

-continued

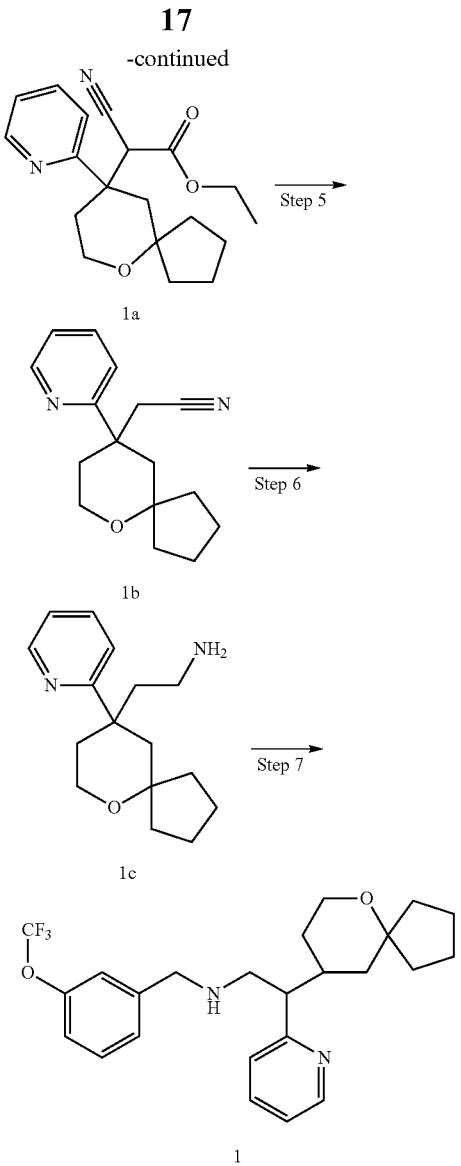

Step 1: Preparing 6-Oxaspiro[4.5]Decan-9-Ol (1-2)

3-buten-1-ol (10 g, 142 mmol) and cyclopentanone (6 g, 71 mmol) were added into the eggplant-shaped bottle and cooled to 0° C. 75% sulfuric acid was slowly added into the reaction solution dropwise, gradually warmed to room temperature then reacted overnight. Water (100 ml) was added into the reaction system, the pH was adjusted to 8 with sodium hydroxide, and the system was extracted with diethyl ether (3×150 ml), the diethyl ether layer was washed with saturated sodium bisulfite (40 ml), dried with magnesium sulfate, and evaporated to dryness, then distilled to obtain 6-oxaspiro[4.5]decan-9-ol (1-2, 4 g), with a yield of: 36%.

Step 2: Preparing 6-Oxaspiro[4.5]Decan-9-One (1-3)

6-oxaspiro[4.5]decan-9-ol (4 g, 25.6 mmol) was dissolved in dichloromethane (100 ml), and pyridinium chlorochromate (PCC, 8.3 g, 39 mmol) was added thereto, the system was reacted at room temperature, after raw material was detected to be disappeared by TCL, the system was filtered, then the filtrate was concentrated and then was subjected to column chromatography (developing solvent was 0% to 50% ethyl acetate/petroleum ether) to obtain 6-oxaspiro[4.5]decan-9-one (1-3, 3.1 g), with a yield of: 78%.

Step 3: Preparing 2-cyano-[(9Z)-6-oxaspiro [4.5] decan-9-ylidene] ethyl acetate (1-4)

6-oxaspiro[4.5]decan-9-one (1-3, 3.1 g, 20 mmol), ethyl cyanoacetate (3.1 g, 24 mmol), ammonium acetate (0.385 g, 5 mmol), acetic acid (0.24 g), and toluene (30 ml) were respectively added into a 50 ml round bottom flask equipped with a Dean-Stark distillation apparatus and a condenser. The system was heated and refluxed until no more water was collected in Dean-Stark, cooled down, toluene was added, and the organic layer was washed with water (30 ml). The aqueous layer was extracted with ethyl acetate (3×50 ml). The combined organic layer was washed with saturated sodium bicarbonate (100 ml) and saline (100 ml), dried with magnesium sulfate, filtered and concentrated. The obtained product was purified by column chromatography (developing solvent was 0% to 60% ethyl acetate/n-hexane) to obtain 2-cyano-[(9Z)-6-oxaspiro[4.5]decan-9-ylidene]ethyl acetate (1-4, 3.5 g), with a yield of: 70%.

Step 4: Preparing 2-cyano-2[9-(pyridin-2-yl)-6-oxaspiro[4.5]decan-9-ylidene]ethyl acetate (1a)

2-pyridine magnesium bromide (1M, 6 mL), cuprous iodide (96 mg, 0.5 mmol), and dry diethyl ether (10 ml) were added into a round bottom flask equipped with a condenser, an addition funnel and a rubber septum with a nitrogen inlet, and cooled to 0° C. 2-cyano-[(9Z)-6-oxaspiro[4.5]decan-9-ylidene] ethyl acetate (1-4, 1.25 g, 5 mmol) was dissolved in anhydrous diethyl ether (10 ml), and was slowly added into the reaction dropwise. After 3 hours, the reaction was complete, and the reaction solution was poured into a mixture of ice/hydrochloric acid (1N, 10 ml), extracted with diethyl ether (3×50 ml), and washed with saturated saline (50 ml), dried with magnesium sulfate, filtered, the filtrate was concentrated and was then subjected to column chromatography (developing solvent: 7% to 60% ethyl acetate/petroleum ether) to obtain 2-cyano-2-[9-(pyridin-2-yl)-6-oxaspiro[4.5]decan-9-ylidene]ethyl acetate (1a, 0.7 g), with a yield of: 43%.

Step 5: Preparing 2-[9-(pyridin-2-yl)-6-oxaspiro [4.5]decan-9-yl]acetonitrile (1b)

2-cyano-2-[9-(pyridin-2-yl)-6-oxaspiro[4.5]decan-9-ylidene]ethyl acetate (1a, 0.66 g, 2 mmol) was added into a pre-dissolved solution of the potassium hydroxide (112 mg, 2 mmol) in ethylene glycol (5 ml). The mixture was heated to 120° C. and reacted for 3 hours, then cooled down. Water (50 ml) was added, the system was extracted with diethyl ether (3×50 ml), washed with water (50 ml), dried with anhydrous magnesium sulfate, filtered and concentrated, and purified by column chromatography (developing solvent was 5% to 40% ethyl acetate/n-hexane) to obtain 2-[9-(pyridin-2-yl)-6-oxaspiro[4.5]decan-9-yl]acetonitrile (1b, 400 mg), with a yield of: 80%.

Step 6: Preparing 2-(9-(pyridin-2-yl)-6-oxaspiro [4.5]decan-9-yl)ethylamine (1c)

Lithium aluminum tetrahydride (120 mg, 3 mmol) was added into a solution of 2-[9-(pyridin-2-yl)-6-oxaspiro[4.5]

decan-9-yl]acetonitrile (1b, 256 mg, 1.0 mmol) in anhydrous diethyl ether (15 ml) at 0° C. After 2 hours, water (0.1 ml) and 15% aqueous sodium hydroxide solution (0.1 ml) were added into the reaction solution respectively, and then quenched with water (0.1 ml). The reaction mixture was extracted with diethyl ether (3×20 ml), dried with anhydrous magnesium sulfate, filtered then concentrated to obtain 2-(9-(pyridin-2-yl)-6-oxaspiro[4.5]decan-9-yl) ethylamine (1c, 200 mg), with a yield of: 77%, as a yellow oily substance, which was used without further purification.

1H NMR (400 MHz, CDCl3) ppm 8.58 (ddd, J=4.8, 1.9, 0.9, 1H), 7.63 (m, 1H), 7.30 (m, 1H), 7.12 (ddd, J=7.4, 4.8, 1.0, 1H), 3.76 (m, 2H), 2.55 (td, J~11.6, 5.1, 1H), 2.46 (ddd, J=13.7, 5.1, 2.7, 1H), 2.37 (dd, J=13.7, 2.1, 1H), 2.14 (td, J=11.6, 5.0, 1H), 1.92 (m, 2H), 1.70 (m, 4H), 1.46 (m, 4H), 1.13 (m, 1H), 0.71 (dt, J=13.4, 8.8, 1H). LC-MS: m/z (ES+) was calculated to be $C_{16}H_{24}N_2O$ 261 [M+1]$^+$.

Step 7: Preparing (3-trifluoromethoxybenzyl)-[2-(9-(pyridin-2-yl)-6-oxaspiro[4.5]decan-9-yl)ethyl]amine

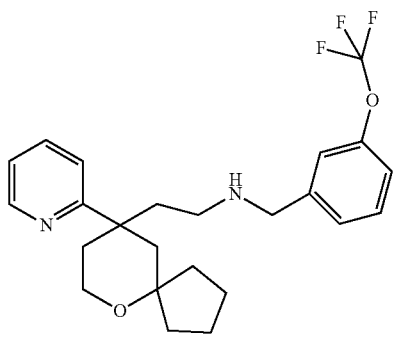 [SMILES: FC(F)(F)Oc1cccc(CNCCC2(c3ccccn3)CCOC3(CCCC3)C2)c1]

2-(9-(pyridin-2-yl)-6-oxaspiro[4.5]decan-9-yl)ethylamine (130 mg, 0.5 mmol), anhydrous magnesium sulfate (72 mg, 0.6 mmol) were added into anhydrous dichloromethane (8 ml), and 3-trifluoromethoxybenzaldehyde (105 mg, 0.55 mmol) was added, and stirred at room temperature overnight. The reaction solution was filtered, and the filtrate was concentrated and then added into anhydrous methanol (5 ml), sodium borohydride (38 mg, 1 mmol) was added at 0° C., 1 hour later, water (10 ml) was added, the system was extracted with dichloromethane (3×20 ml), washed with saturated saline (10 ml), and dried with anhydrous sodium sulfate. Purified by thin layer chromatography (developing solvent was 0-10% methanol/dichloromethane) to obtain compound (3-trifluoromethoxybenzyl)-[2-(9-(pyridin-2-yl)-6-oxaspiro[4.5]decan-9-yl)ethyl]amine (76 mg, yellow oily substance), yield: 50%.

1H NMR (400 MHz, CDCl3) ppm 8.49 (dd, J=4.8, 1.2 Hz, 1H), 7.58 (td, J=7.6, 2.0 Hz, 1H), 7.30-7.21 (m, 3H), 7.09-7.07(m, 3H), 3.72-3.68 (m, 4H), 2.56 (td, J=10.8, 5.2 Hz, 1H), 2.38 (dd, J=13.6, 2.0 Hz, 1H), 2.32(dd, J=13.6, 2.0 Hz, 1H), 2.16-2.03 (m, 2H), 1.87 (d, J=13.6 Hz, 2H), 1.72-1.56 (m, 3H), 1.50-1.34 (m, 4H), 1.06 (m, 1H), 0.67-0.60 (m, 1H). LC-MS: m/z (ES+) was calculated to be $C_{24}H_{29}F_3N_2O_2$ 435 [M+1]$^+$.

Example 2: Preparation of (2-chloro-4-trifluoromethoxybenzyl)-[2-(9-(pyridin-2-yl)-6-oxaspiro[4.5]decan-9-yl)ethyl]amine (H02)

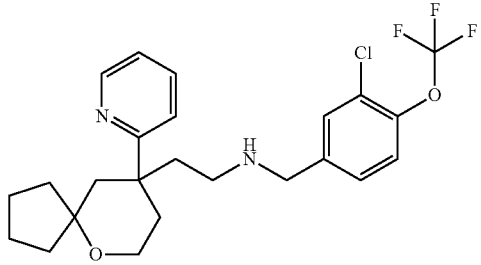 [SMILES: FC(F)(F)Oc1ccc(CNCCC2(c3ccccn3)CCOC3(CCCC3)C2)cc1Cl]

The preparation method was the same as that in Example 1, and the 3-trifluoromethoxybenzaldehyde in the step 7 was replaced by 3-chloro-4-trifluoromethoxybenzaldehyde to obtain (2-chloro-4-trifluoromethoxybenzyl)-[2-(9-(pyridin-2-yl)-6-oxaspiro[4.5]decan-9-yl)ethyl]amine 100 mg, with a yield of 75%, the appearance was a light yellow sticky substance.

1H NMR (400 MHz, CDCl$_3$) ppm 8.51 (dd, J=4.8, 1.2 Hz, 1H), 7.60 (td, J=7.6, 2.0 Hz, 1H), 7.31 (d, J=1.6 Hz, 1H), 7.10 (d, J=8.4 Hz, 1H), 7.20-7.07 (m, 3H), 3.74-3.72 (m, 2H), 3.61 (s, 2H), 2.50 (td, J=10.8, 5.2 Hz, 1H), 2.39 (dd, J=14.0, 2.0 Hz, 1H), 2.32 (dd, J=13.6, 2.0 Hz, 1H), 2.14-1.97 (m, 2H), 1.90 (d, J=13.6 Hz, 1H), 1.81-1.57 (m, 4H), 1.52-1.43 (m, 3H), 1.36 (m, 1H), 1.08 (m, 1H), 0.70-0.62 (m, 1H). LC-MS: m/z (ES+) was calculated to be $C_{24}H_{28}ClF_3N_2O_2$ 469 [M+1]$^+$.

Example 3: Preparation of N-methyl-2-((((2-(9-(pyridin-2-yl)-6-oxaspiro[4.5]decan-9-yl)ethyl)amino)methyl)aniline (H03)

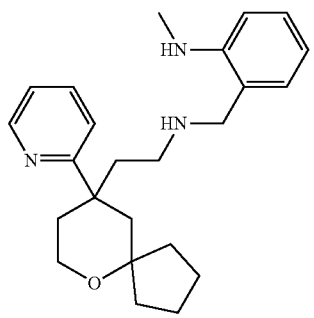 [SMILES: CNc1ccccc1CNCCC1(c2ccccn2)CCOC2(CCCC2)C1]

The preparation method was the same as that in Example 1, and the 3-trifluoromethoxybenzaldehyde in the step 7 was replaced by 2-methylaminobenzaldehyde to prepare N-methyl-2-((((2-(9-(pyridin-2-yl)-6-oxaspiro[4.5]decan-9-yl)ethyl)amino)methyl)aniline 38 mg, with a yield of 32%, the appearance was a light yellow sticky substance.

1H NMR (400 MHz, CDCl$_3$) ppm 8.55 (dd, J=4.8, 1.2 Hz, 1H), 7.60 (td, J=7.6, 2.0 Hz, 1H), 7.15 (td, J=7.6, 1.6 Hz, 1H), 7.10 (qd, J=4.8, 0.8 Hz, 1H), 6.87 (dd, J=7.2, 1.2 Hz, 1H), 6.58-6.55 (m, 2H), 3.74 (dd, J=8.0, 2.8 Hz, 2H), 3.55 (d, J=1.6 Hz, 2H), 2.78 (s, 3H), 2.47-2.31 (m, 3H), 2.08 (td, J=11.2, 5.2 Hz, 1H), 1.97-1.88 (m, 2H), 1.73-1.64 (m, 3H), 1.53-1.44 (m, 5H), 1.10 (m, 1H), 0.72-0.64 (m, 1H). LC-MS: m/z (ES+) was calculated to be $C_{24}H_{33}N_3O$ 380 $[M+1]^+$.

Example 4: Preparation of (3-chloro-2-methylbenzyl)-[2-(9-(pyridin-2-yl)-6-oxaspiro[4.5]decan-9-yl)ethyl]amine (H04)

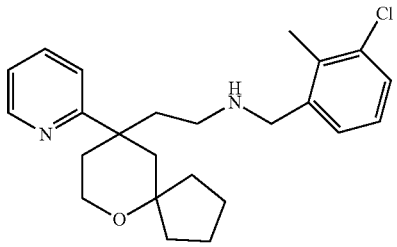 [SMILES: Cc1c(Cl)cccc1CNCCC1(c2ccccn2)CCOC2(CCCC2)C1]

The preparation method was the same as that in Example 1, and the 3-trifluoromethoxybenzaldehyde in the step 7 was replaced by 2-methyl-3-chlorobenzaldehyde to prepare (3-chloro-2-methylbenzyl)-[2-(9-(pyridin-2-yl)-6-oxaspiro[4.5]decan-9-yl)ethyl]amine 95 mg, with a yield of 63%, the appearance was a light yellow sticky substance.

1H NMR (400 MHz, CDCl$_3$) ppm 8.52 (dd, J=4.8, 1.2 Hz, 1H), 7.60 (td, J=7.6, 2.0 Hz, 1H), 7.26 (d, J=8.0 Hz, 1H), 7.20 (d, J=7.6 Hz, 1H), 7.10-6.98 (m, 3H), 3.74-3.71 (m, 2H), 3.60 (d, J=2.0 Hz, 2H), 2.54 (td, J=11.2, 5.2 Hz, 1H), 2.40 (dd, J=14.0, 2.4 Hz, 1H), 8.52 (dd, J=13.6, 1.6 Hz, 1H), 2.26 (s, 3H), 2.12 (td, J=11.2, 4.8 Hz, 1H), 2.03-1.96 (m, 1H), 1.88 (d, J=13.6 Hz, 1H), 1.81-1.60 (m, 4H), 1.52-1.35 (m, 4H), 1.07 (m, 1H), 0.67-0.62 (m, 1H). LC-MS: m/z (ES+) was calculated to be $C_{24}H_{31}ClN_2O$ 399 $[M+1]^+$.

Example 5: Preparation of ((3-chloro-thiophen-2-yl)methyl)-[2-(9-(pyridin-2-yl)-6-oxaspiro[4.5]decan-9-yl)ethyl]amine (H05)

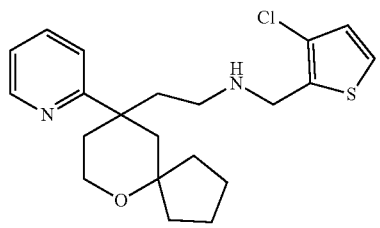 [SMILES: Clc1ccsc1CNCCC1(c2ccccn2)CCOC2(CCCC2)C1]

The preparation method was the same as that in Example 1, and the 3-trifluoromethoxybenzaldehyde in the step 7 was replaced by 3-chlorothiophene-2-formaldehyde to prepare ((3-chloro-thiophen-2-yl)methyl)-[2-(9-(pyridin-2-yl)-6-oxaspiro[4.5]decan-9-yl)ethyl]amine 64 mg, with a yield of 45%, the appearance was a light yellow sticky substance.

1H NMR (400 MHz, CDCl$_3$) ppm 8.53 (dd, J=4.8, 0.8 Hz, 1H), 7.60 (td, J=7.6, 2.0 Hz, 1H), 7.26 (d, J=8.0 Hz, 1H), 7.13 (d, J=5.2 Hz, 1H), 7.10-7.07 (qd, J=4.8, 1.2 Hz, 1H), 6.80 (d, J=5.6 Hz, 1H), 3.78 (d, J=3.6 Hz, 2H), 3.74-3.71 (m, 2H), 2.53 (td, J=10.8, 5.2 Hz, 1H), 2.42-2.30 (m, 2H), 2.12 (td, J=11.2, 5.2 Hz, 1H), 2.01-1.94 (m, 1H), 1.89 (d, J=13.6 Hz, 1H), 1.77-1.60 (m, 4H), 1.50-1.35 (m, 4H), 1.07 (m, 1H), 0.70-0.64 (m, 1H). LC-MS: m/z (ES+) was calculated to be $C_{21}H_{27}ClN_2OS$ 391 $[M+1]^+$.

Example 6: Preparation of (4-trifluoromethoxybenzyl)-[2-(9-(pyridin-2-yl)-6-oxaspiro[4.5]decan-9-yl)ethyl]amine (H06)

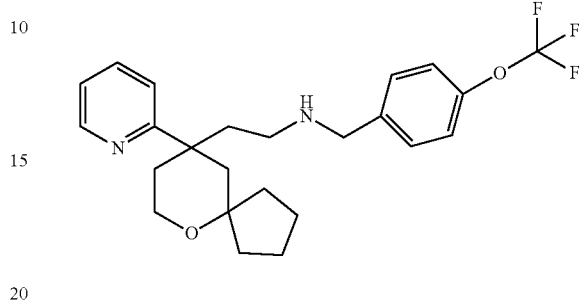

The preparation method was the same as that in Example 1, and the 3-trifluoromethoxybenzaldehyde in the step 7 was replaced by 4-trifluoromethoxybenzaldehyde to prepare (4-trifluoromethoxybenzyl)-[2-(9-(pyridin-2-yl)-6-oxaspiro[4.5]decan-9-yl)ethyl]amine 40 mg, with a yield of 52%, the appearance was a light yellow sticky substance.

1H NMR (400 MHz, CDCl$_3$) ppm 8.50 (d, J=3.6 Hz, 1H), 7.60 (td, J=7.6, 1.6.0 Hz, 1H), 7.29-7.25 (m, 3H), 7.11-7.09 (m, 3H), 3.73 (m, 2H), 3.68 (d, J=2.4 Hz, 2H), 2.60-2.5 (m, 1H), 2.40-2.31 (m, 2H), 2.16-2.03 (m, 2H), 1.90 (d, J=13.6 Hz, 2H), 1.75-1.61 (m, 3H), 1.47 (m, 4H), 1.09 (m, 1H), 0.70-0.62 (m, 1H). LC-MS: m/z (ES+) was calculated to be $C_{24}H_{29}F_3N_2O_2$ 435 $[M+1]^+$.

Example 7: Preparation of (3,4-dimethylbenzyl)-[2-(9-(pyridin-2-yl)-6-oxaspiro[4.5]decan-9-yl)ethyl]amine (H07)

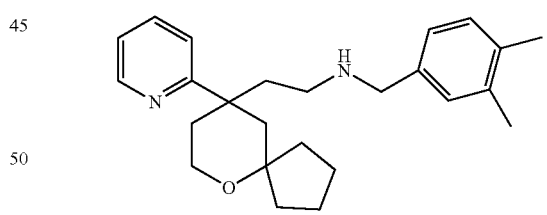

The preparation method was the same as that in Example 1, and the 3-trifluoromethoxybenzaldehyde in the step 7 was replaced by 3,4-dimethylbenzaldehyde to prepare (3,4-dimethylbenzyl)-[2-(9-(pyridin-2-yl)-6-oxaspiro[4.5]decan-9-yl)ethyl]amine 40 mg, with a yield of 50%, the appearance was a light yellow sticky substance.

1H NMR (400 MHz, CDCl$_3$) ppm 8.46 (d, J=4.0 Hz, 1H), 7.60 (td, J=7.6, 2.0 Hz, 1H), 7.26 (s, 1H), 7.10-7.03 (m, 4H), 3.73-3.64 (m, 5H), 3.47 (s, 1H), 2.70 (m, 1H), 2.29-2.23 (m, 4H), 2.17 (d, J=8.4 Hz, 6H), 2.05 (m, 2H), 1.87 (d, J=13.6 Hz, 2H), 1.77-1.60 (m, 4H), 1.47-1.25 2.59 (m, 6H), 1.06 (m, 1H), 0.62 (m, 1H). LC-MS: m/z (ES+) was calculated to be $C_{25}H_{34}N_2O$ 379 $[M+1]^+$.

Example 8: Preparation of (2,4-dimethylbenzyl)-[2-(9-(pyridin-2-yl)-6-oxaspiro[4.5]decan-9-yl)ethyl]amine (H08)

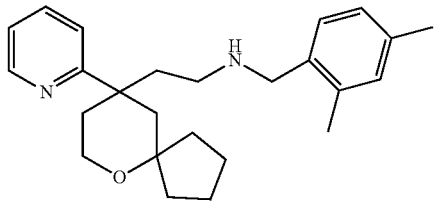 [SMILES: Cc1ccc(CNCCC2(c3ccccn3)CCOC3(CCCC3)C2)c(C)c1]

The preparation method was the same as that in Example 1, and the 3-trifluoromethoxybenzaldehyde in the step 7 was replaced by 2,4-dimethylbenzaldehyde to prepare (2,4-dimethylbenzyl)-[2-(9-(pyridin-2-yl)-6-oxaspiro[4.5]decan-9-yl)ethyl]amine 60 mg, with a yield of 65%, the appearance was a light yellow sticky substance.

1H NMR (400 MHz, CDCl$_3$) ppm 8.45 (d, J=4.4 Hz, 1H), 7.62 (td, J=7.6, 2.0 Hz, 1H), 7.28 (d, J=8.0 Hz, 1H), 7.23 (d, J=8.0 Hz, 1H), 7.10 (q, 1H), 6.93 (s, 2H), 3.79-3.65 (m, 4H), 2.76 (td, J=11.6, 5.2 Hz, 1H), 2.26 (s, 5H), 2.21 (s, 4H), 2.06 (m, 2H), 1.87 (d, J=13.6 Hz, 1H), 1.75 (t, J=9.2 Hz, 1H), 1.69-1.62 (m, 2H), 1.45 (m, 2H), 1.06 (m, 1H), 0.64 (m, 1H). LC-MS: m/z (ES+) was calculated to be $C_{25}H_{34}N_2O$ 379 [M+1]$^+$.

Example 9: Preparation of (2-trifluoromethoxybenzyl)-[2-(9-(3-chloro-5-fluoropyridin-2-yl)-6-oxaspiro[4.5]decan-9-yl)ethyl]amine (H09)

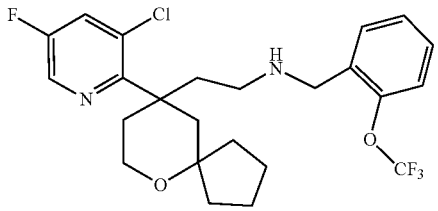 [SMILES: Fc1cnc(C2(CCNCc3ccccc3OC(F)(F)F)CCOC3(CCCC3)C2)c(Cl)c1]

The preparation method was the same as that in Example 1, and the pyridine-2-magnesium bromide in the step 4 was replaced by 3-chloro-5-fluoropyridine-2-magnesium bromide, the 3-trifluoromethoxybenzaldehyde in the step 7 was replaced by 2-trifluoromethoxybenzaldehyde, to prepare (2-trifluoromethoxybenzyl)-[2-(9-(3-chloro-5-fluoropyridin-2-yl)-6-oxaspiro[4.5]decan-9-yl)ethyl]amine 20 mg, with a yield of 38%, the appearance was a light yellow sticky substance.

1H NMR (400 MHz, CDCl$_3$) ppm 8.35 (d, J=2.8 Hz, 1H), 7.33-7.27 (m, 2H), 7.26-7.15 (m, 3H), 3.71-3.65 (m, 4H), 2.42 (td, J=11.2, 5.2 Hz, 1H), 2.35 (dd, J=14.0, 2.0 Hz, 1H), 2.26 (dd, J=13.6, 2.0 Hz, 1H), 2.42 (td, J=11.2, 4.8 Hz, 1H), 1.96-1.87 (m, 2H), 1.76-1.64 (m, 4H), 1.52-1.35 (m, 4H), 1.09 (m, 1H), 0.71-0.61 (m, 1H). LC-MS: m/z (ES+) was calculated to be $C_{24}H_{27}ClF_4N_2O_2$ 486 [M+1]$^+$.

Example 10: Preparation of (2-trifluoromethoxybenzyl)-[2-(9-(3-methyl-5-fluoropyridin-2-yl)-6-oxaspiro[4.5]decan-9-yl)ethyl]amine (H10)

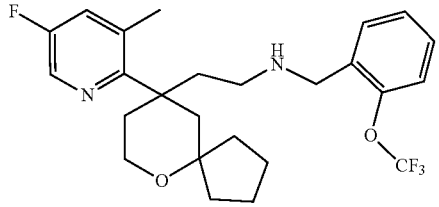 [SMILES: Cc1cc(F)cnc1C1(CCNCc2ccccc2OC(F)(F)F)CCOC2(CCCC2)C1]

The preparation method was the same as that in Example 1, and the pyridine-2-magnesium bromide in the step 4 was replaced by 3-methyl-5-fluoropyridine-2-magnesium bromide, the 3-trifluoromethoxybenzaldehyde in the step 7 was replaced by 2-trifluoromethoxybenzaldehyde, to prepare (2-trifluoromethoxybenzyl)-[2-(9-(3-methyl-5-fluoropyridin-2-yl)-6-oxaspiro[4.5]decan-9-yl)ethyl]amine 35 mg, with a yield of 34%, the appearance was a light yellow sticky substance.

1H NMR (400 MHz, CDCl$_3$) ppm 8.33 (d, J=2.8 Hz, 1H), 7.34-7.25 (m, 2H), 7.26-7.15 (m, 3H), 3.71-3.65 (m, 4H), 2.42 (td, J=11.2, 5.2 Hz, 1H), 2.35 (m, 4H), 2.26 (dd, J=13.6, 2.0 Hz, 1H), 2.42 (td, J=11.2, 4.8 Hz, 1H), 1.96-1.87 (m, 2H), 1.76-1.64 (m, 4H), 1.52-1.35 (m, 4H), 1.09 (m, 1H), 0.71-0.61 (m, 1H). LC-MS: m/z (ES+) was calculated to be $C_{25}H_{30}F_2N_2O_2$ 467 [M+1]$^+$.

Example 11: Preparation of (4-bromo-2-trifluoromethoxybenzyl)-[2-(9-(pyridin-2-yl)-6-oxaspiro[4.5]decan-9-yl)ethyl]amine (H11)

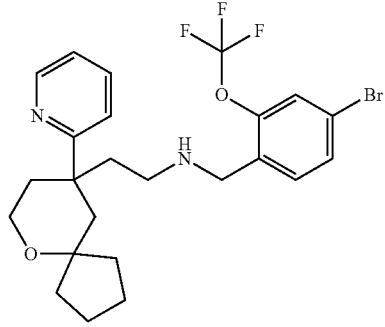 [SMILES: FC(F)(F)Oc1cc(Br)ccc1CNCCC1(c2ccccn2)CCOC2(CCCC2)C1]

The preparation method was the same as that in Example 1, and the 3-trifluoromethoxybenzaldehyde in the step 7 was replaced by 2-trifluoromethoxy-4-bromobenzaldehyde to prepare (4-bromo-2-trifluoromethoxybenzyl)-[2-(9-(pyridin-2-yl)-6-oxaspiro[4.5]decan-9-yl)ethyl]amine 78 mg, with a yield of 58%, the appearance was a light yellow sticky substance.

1H NMR (400 MHz, CDCl$_3$) ppm 8.50 (dd, J=4.0, 0.8 Hz, 1H), 7.60 (td, J=7.6, 2.0 Hz, 1H), 7.34-7.33 (m, 2H), 7.28 (s, 1H), 7.20 (d, J=8.4 Hz, 1H), 7.10 (q, J=4.8, 6.8 Hz, 1H), 3.75 (d, J=2.8 Hz, 1H), 3.73 (d, J=2.4 Hz, 1H), 3.36 (s, 2H), 2.50-2.32 (m, 3H), 2.07 (td, J=11.2, 5.2 Hz, 1H), 2.00-1.96 (m, 1H), 1.90 (d, J=14.0 Hz, 1H), 1.78-1.65 (m, 6H), 1.54-1.48 (m, 3H), 1.10 (m, 1H), 0.72-0.65 (m, 1H). LC-MS: m/z (ES+) was calculated to be $C_{24}H_{28}BrF_3N_2O_2$ 513 $[M+1]^+$.

Example 12: Preparation of (4-methyl-2-trifluoromethoxybenzyl)-[2-(9-(pyridin-2-yl)-6-oxaspiro[4.5]decan-9-yl)ethyl]amine (H12)

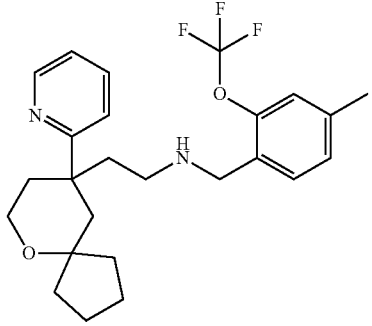 [SMILES: Cc1ccc(CNCCC2(c3ccccn3)CCOC3(CCCC3)C2)c(OC(F)(F)F)c1]

The preparation method was the same as that in Example 1, and the 3-trifluoromethoxybenzaldehyde in the step 7 was replaced by 2-trifluoromethoxy-4-methylbenzaldehyde to prepare (4-methyl-2-trifluoromethoxybenzyl)-[2-(9-(pyridin-2-yl)-6-oxaspiro[4.5]decan-9-yl)ethyl]amine 91 mg, with a yield of 70%, the appearance was a light yellow sticky substance.

1H NMR (400 MHz, CDCl$_3$) ppm 8.50 (dd, J=4.8, 1.2 Hz, 1H), 7.60 (td, J=7.6, 2.0 Hz, 1H), 7.28(t, J=8.0 Hz, 2H), 7.08(q, J=4.8, 6.8 Hz, 1H), 7.01 (d, J=8.0 Hz, 1H), 6.98 (s, 1H), 3.74-3.69 (m, 4H), 2.53 (td, J=11.6, 5.6 Hz, 1H), 2.4-2.37 (m, 1H), 2.32-2.29 (m, 4H), 2.13 (td, J=11.2, 4.8 Hz, 1H), 2.06-1.99 (m, 1H), 1.88 (d, J=14.0 Hz, 1H), 1.85-1.77 (m, 1H), 1.73-1.58 (m, 3H), 1.51-1.45 (m, 3H), 1.38-1.35 (m, 1H), 1.11-1.07 (m, 1H), 0.70-0.62 (m, 1H). LC-MS: m/z (ES+) was calculated to be $C_{25}H_{31}F_3N_2O_2$ 449 $[M+1]^+$.

Example 13: Preparation of 3-{[(2-(9-(pyridin-2-yl)-6-oxaspiro[4.5]decan-9-yl)ethyl]aminemethyl}-2-trifluoromethoxybenzo nitrile (H13)

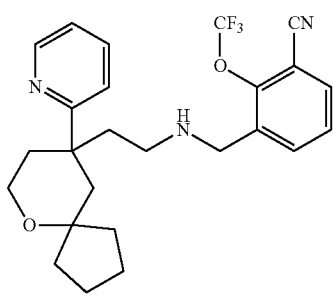 [SMILES: N#Cc1cccc(CNCCC2(c3ccccn3)CCOC3(CCCC3)C2)c1OC(F)(F)F]

The preparation method was the same as that in Example 1, and the 3-trifluoromethoxybenzaldehyde in the step 7 was replaced by 2-trifluoromethoxy-4-cyanobenzaldehyde to prepare 3-{[(2-(9-(pyridin-2-yl)-6-oxaspiro[4.5]decan-9-yl)ethyl]aminemethyl}-2-trifluoromethoxybenzonitrile 45 mg, with a yield of 51%, the appearance was a light yellow sticky substance.

1H NMR (400 MHz, CDCl$_3$) ppm 8.54-8.52 (m, 1H), 7.59 (dd, J=1.2 Hz, 1H), 7.25-7.30 (m, 2H), 7.25-7.18 (m, 3H), 3.75-3.64 (m, 4H), 2.62-2.32 (m, 3H), 1.91-1.73 (m, 3H), 1.69-1.40 (m, 8H), 1.09 (m, 1H), 0.70-0.62 (m, 1H). LC-MS: m/z (ES+) was calculated to be C25H28F3N3O2 460 [M+1]+.

Example 14: Preparation of ((3-trifluoromethylthiophen-2-yl)methyl)-[2-(9-(pyridin-2-yl)-6-oxaspiro[4.5]decan-9-yl)ethyl]a mine (H14)

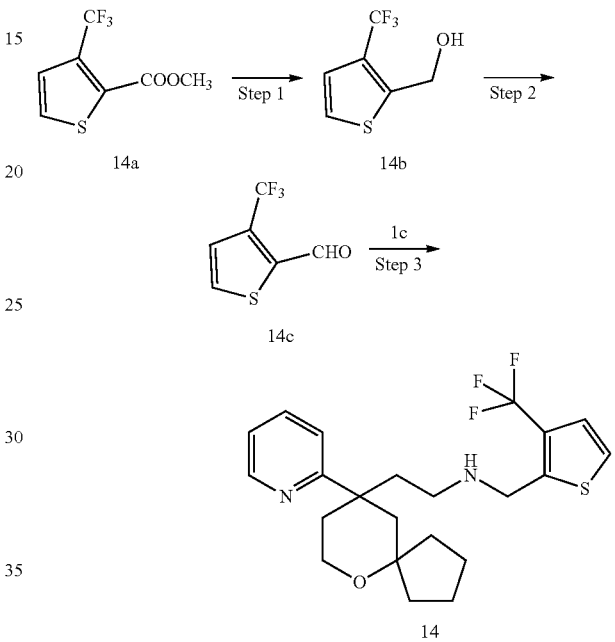

Step 1: Preparing 3-(trifluoromethylthiophen-2-yl)methanol (14b)

Lithium aluminum tetrahydride (240 mg, 6 mmol) was added dropwise into a solution of 3-trifluoromethylthiophene-2-carboxylic acid methyl ester (14a, 1 g, 4.7 mmol) in anhydrous diethyl ether (20 ml) at 0° C. After 2 hours, water (0.1 ml) and 15% aqueous sodium hydroxide solution (0.1 ml) were added into the reaction solution respectively, and then quenched with water (0.1 ml). The reaction mixture was extracted with ethyl acetate (3×20 ml), dried with anhydrous magnesium sulfate, filtered then concentrated to obtain 3-(trifluoromethylthiophen-2-yl)methanol (14b) (14b, 500 mg), yield: 57%, as a yellow oily substance, which was used without further purification.

Step 2: Preparing 3-trifluoromethylthiophene-2-carbaldehyde (14c)

3-(trifluoromethylthiophen-2-yl)methanol (14b, 0.364 g, 2 mmol) was dissolved in dichloromethane (10 ml), and pyridinium chlorochromate (PCC, 830 mg, 3.9 mmol) was added thereto, reacted at room temperature, after the disappearance of raw materials was detected by TLC, filtered, and after the concentration of the filtrate, column chromatography (developing agent was 0% to 50% ethyl acetate/petroleum ether) was performed to obtain 3-trifluoromethylthiophene-2-carbaldehyde (14c, 0.2 g), yield: 55%.

Step 3

Consistent with the step 7 in the preparation method described in Example 1, 3-trifluoromethoxybenzaldehyde in the step 7 of Example 1 was replaced by 3-trifluoromethylthiophene-2-carbaldehyde to prepare ((3-trifluoromethyl-thiophen-2-yl)methyl)-[2-(9-(pyridin-2-yl)-6-oxaspiro[4.5]decan-9-yl)ethyl]amine 21 mg, with a yield of 25%, and the appearance was a light yellow sticky substance.

1H NMR (400 MHz, CDCl$_3$) ppm 8.55 (dd, J=4.8, 1.2 Hz, 1H), 7.61 (td, J=7.6, 2.0 Hz, 1H), 7.32 (d, J=8.0 Hz, 1H), 7.24 (d, J=5.2 Hz, 1H), 7.10-7.06 (qd, J=4.8, 1.2 Hz, 1H), 6.93 (d, J=5.2 Hz, 1H), 6.44 (s, 1H), 4.63 (s, 2H), 3.76-3.73 (m, 2H), 3.34-3.26 (m, 1H), 2.99-2.90 (m, 1H), 2.47 (dd, J=13.6, 2.0 Hz, 1H), 2.38 (dd, J=13.6, 2.0 Hz, 1H), 2.13-2.05 (m, 1H), 1.90 (d, J=13.6 Hz, 2H), 1.83-1.58 (m, 5H), 1.53-1.44 (m, 3H), 1.09 (m, 1H), 0.71-0.64 (m, 1H). LC-MS: m/z (ES+) was calculated to be C$_{22}$H$_{27}$F$_3$N$_2$OS 425 [M+1]$^+$.

Example 15: Preparation of 4-{[2-(9-(pyridin-2-yl)-6-oxaspiro[4.5]decan-9-yl)ethylamine]methyl}-3-trifluoromethoxyphenol (H15)

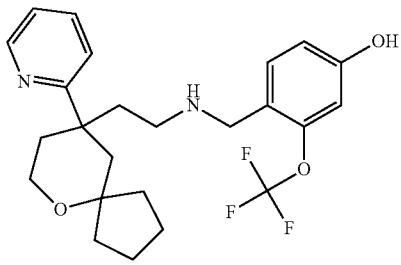 [SMILES: Oc1ccc(CNCCC2(c3ccccn3)CCOC3(CCCC3)C2)c(OC(F)(F)F)c1]

The preparation method was the same as that in Example 1, and the 3-trifluoromethoxybenzaldehyde in the step 7 was replaced by 2-trifluoromethoxy-4-hydroxybenzaldehyde to prepare 4-{[2-(9-(pyridin-2-yl)-6-oxaspiro[4.5]decan-9-yl)ethylamine]methyl}-3-trifluoromethoxyphenol 56 mg, with a yield of 52%, the appearance was a light yellow sticky substance.

1H NMR (400 MHz, CDCl$_3$) ppm 8.46 (d, J=4.4 Hz, 1H), 7.65 (td, J=7.6, 1.6 Hz, 1H), 7.31 (d, J=8.0 Hz, 1H), 7.18-7.14 (m, 2H), 6.61 (s, 1H), 6.48 (d, J=7.2 Hz, 1H), 3.73 (m, 4H), 2.76 (m, 1H), 2.39-2.30 (m, 3H), 2.13 (m, 1H), 1.94 (m, 1H), 1.87 (d, J=14.0 Hz, 1H), 1.74-1.62 (m, 3H), 1.48-1.37 (m, 4H), 1.09 (m, 1H), 0.69-0.61 (m, 1H). LC-MS: m/z (ES+) was calculated to be C$_{24}$H$_{29}$F$_3$N$_2$O$_3$ 451 [M+1]$^+$.

Example 16: Preparation of (2-difluoromethoxybenzyl)-[2-(9-(pyridin-2-yl)-6-oxaspiro[4.5]decan-9-yl)ethyl]amine (H16)

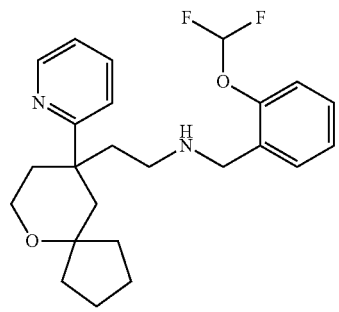 [SMILES: FC(F)Oc1ccccc1CNCCC1(c2ccccn2)CCOC2(CCCC2)C1]

The preparation method was the same as that in Example 1, and the 3-trifluoromethoxybenzaldehyde in the step 7 was replaced by 2-difluoromethoxybenzaldehyde to prepare (2-difluoromethoxybenzyl)-[2-(9-(pyridin-2-yl)-6-oxa-spiro[4.5]decan-9-yl)ethyl]amine 16 mg, with a yield of 28%, the appearance was a light yellow sticky substance.

1H NMR (400 MHz, CDCl$_3$) ppm 8.49 (d, J=4.4 Hz, 1H), 7.61 (td, J=7.6, 2.0 Hz, 1H), 7.38 (d, J=8.4 Hz, 1H), 7.28-7.27 (m, 2H), 7.15-7.06 (m, 3H), 6.78-6.42 (t, J=73.6 Hz, 1H), 3.78-3.71 (m, 4H), 2.62 (td, J=11.2, 5.2 Hz, 1H), 2.36 (d, J=13.6 Hz, 1H), 2.30 (d, J=14.0 Hz, 1H), 2.18 (td, J=11.2, 4.8 Hz, 1H), 2.08 (td, J=13.2, 4.8 Hz, 1H), 1.90-1.87 (m, 2H), 1.78-1.63 (m, 3H), 1.49-1.36 (m, 4H), 1.09 (m, 1H), 0.70-0.62 (m, 1H). LC-MS: m/z (ES+) was calculated to be C$_{24}$H$_{30}$F$_2$N$_2$O$_2$ 417 [M+1]$^+$.

Example 17: Preparation of (5-chloro-2-trifluoromethoxybenzyl)-[2-(9-(pyridin-2-yl)-6-oxaspiro[4.5]decan-9-yl) ethyl]amine (H17)

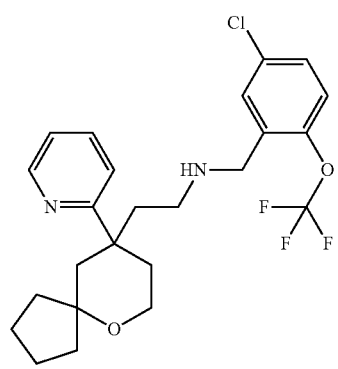 [SMILES: FC(F)(F)Oc1ccc(Cl)cc1CNCCC1(c2ccccn2)CCOC2(CCCC2)C1]

The preparation method was the same as that in Example 1, and the 3-trifluoromethoxybenzaldehyde in the step 7 was replaced by 2-trifluoromethoxy-5-chlorobenzaldehyde to prepare (2-difluoromethoxybenzyl)-[2-(9-(pyridin-2-yl)-6-oxaspiro[4.5]decan-9-yl)ethyl]amine 100 mg, with a yield of 80%, the appearance was a light yellow sticky substance.

1H NMR (400 MHz, CDCl$_3$) ppm 8.55 (dd, J=4.8, 1.2 Hz, 1H), 7.61 (td, J=7.6, 2.0 Hz, 1H), 7.32 (d, J=2.8 Hz, 1H), 7.28 (d, J=8.4 Hz, 1H), 7.18 (dd, J=8.8, 2.4 Hz, 1H), 7.12-7.08 (m, 2H), 3.75 (dd, J=8.4, 2.8 Hz, 2H), 3.63 (s, 2H), 2.51-2.33 (m, 3H), 2.10 (td, J=10.8, 5.2 Hz, 1H), 2.03-1.95

(m, 1H), 1.91 (d, J=13.6 Hz, 1H), 1.78-1.61 (m, 5H), 1.54-1.50 (m, 3H), 1.10 (m, 1H), 0.73-0.66 (m, 1H). LC-MS: m/z (ES+) was calculated to be $C_{24}H_{28}ClF_3N_2O_2$ 469 $[M+1]^+$.

Example 18: Preparation of ((3-difluoromethoxy-thiophen-2-yl)methyl)-[2-(9-(pyridin-2-yl)-6-oxas-piro[4.5]decan-9-yl)ethyl]a mine (H18)

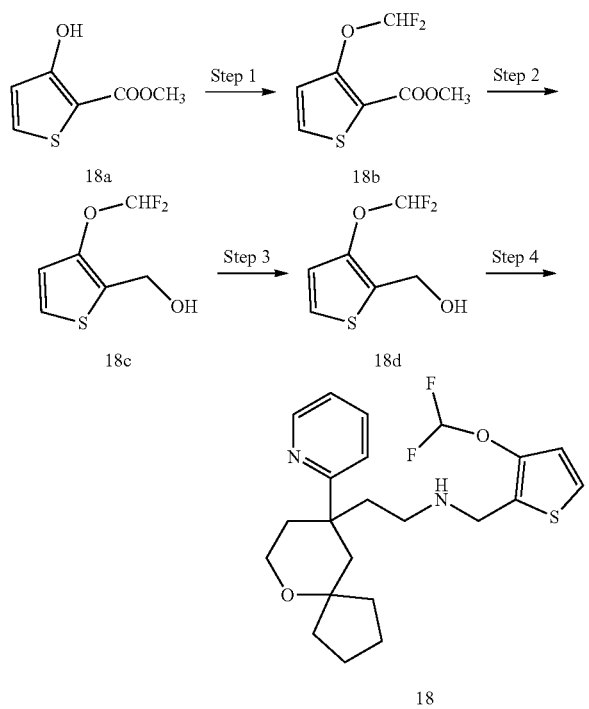

Step 1: Preparing 3-difluoromethoxythiophene-2-formic acid methyl ester (18b)

At room temperature, 3-hydroxythiophene-2-formic acid methyl ester (18a, 1 g, 6.3 mmol) and sodium hydroxide (0.51 g, 12.7 mmol) were respectively added to toluene/water (10 ml/0.8 ml), warmed to 90° C., and tetra-n-butylphosphine bromide (0.11 g, 0.32 mmol) and monochlorodifluoromethane (3.28 g, 37.8 mmol) were respectively added to the reaction solution. The reaction was continued for 1 hour, cooled, water (15 ml) was added, and the organic phase was separated and then dried, dried with magnesium sulfate, and after concentration, column chromatography (developing solvent: ethyl acetate/petroleum ether=1:3) was performed to obtain 3-difluoromethoxythiophene-2-carboxylic acid methyl ester (18b, 0.4 g), yield: 31%.

Step 2: Preparing 3-(difluoromethoxythiophen-2-yl) methanol (18c)

Lithium aluminum tetrahydride (120 mg, 3 mmol) was added to a solution of 3-difluoromethoxythiophene-2-formic acid methyl ester (18b, 0.4 g, 1.9 mmol) in anhydrous diethyl ether (15 ml) at 0° C. After 1 hours, water (0.1 ml) and 15% aqueous sodium hydroxide solution (0.1 ml) were added to the reaction solution respectively, and then quenched with water (0.1 ml). The reaction mixture was extracted with ethyl acetate (3×20 ml), dried with anhydrous magnesium sulfate, filtered then concentrated to obtain 3-(difluoromethoxythiophen-2-yl) methanol (18c, 300 mg), yield: 83%, as a yellow oily substance, which was used without further purification.

Step 3: Preparing 3-difluoromethoxythiophene-2-carbaldehyde (18d)

3-(difluoromethoxythiophen-2-yl)methanol (18c, 0.3 g, 1.67 mmol) was dissolved in dichloromethane (10 ml), and pyridinium chlorochromate (PCC, 830 mg, 3.9 mmol) was added thereto, the reaction was conducted at room temperature, after the disappearance of raw materials was detected by TLC, filtered, after the concentration of the filtrate, column chromatography (developing agent was 0% to 50% ethyl acetate/n-hexane) was performed to obtain 3-difluoromethoxythiophene-2-carboxaldehyde (18d, 0.15 g), yield: 50%.

Step 4

Consistent with the step 7 described in the preparation of Example 1, the 3-trifluoromethoxybenzaldehyde in the step 7 of the preparation method of Example 1 was replaced by 3-difluoromethoxythiophene-2-carboxaldehyde to prepare ((3-difluoromethoxythiophen-2-yl)methyl)-[2-(9-(pyridin-2-yl)-6-oxaspiro[4.5]decan-9-yl) ethyl]amine 34 mg, with a yield of 28%, and the appearance was a light yellow sticky substance.

1H NMR (400 MHz, CDCl₃) ppm 8.51 (dd, J=4.8, 1.2 Hz, 1H), 7.62 (td, J=7.6, 1.6 Hz, 1H), 7.28 (d, J=8.0 Hz, 1H), 7.26 (s, 1H), 7.18 (d, J=5.6 Hz, 1H), 7.10 (q, J=4.8, 6.8 Hz, 1H), 6.81 (d, J=5.6 Hz, 1H), 6.65-6.29 (t, J=73.6 Hz, 1H), 3.90 (d, J=5.6 Hz, 2H), 3.74-3.69 (m, 2H), 2.64 (td, J=11.6, 5.2 Hz, 1H), 2.38 (d, J=12.0 Hz, 1H), 2.32 (d, J=13.6 Hz, 1H), 2.21 (td, J=11.2, 5.2 Hz, 1H), 2.08 (td, J=11.2, 3.2 Hz, 1H), 1.89 (d, J=13.6 Hz, 2H), 1.76-1.63 (m, 4H), 1.52-1.45 (m, 2H), 1.10 (m, 1H), 0.70-0.62 (m, 1H). LC-MS: m/z (ES+) was calculated to be $C_{22}H_{28}F_2N_2O_2S$ 423 $[M+1]^+$.

Example 19: Preparation of 2-[2-(9-(pyridin-2-yl)-6-oxaspiro[4.5]decan-9-yl)ethyl]-7-trifluoromethyl-1,2,3,4-tetrahydroisoquinoline (H19)

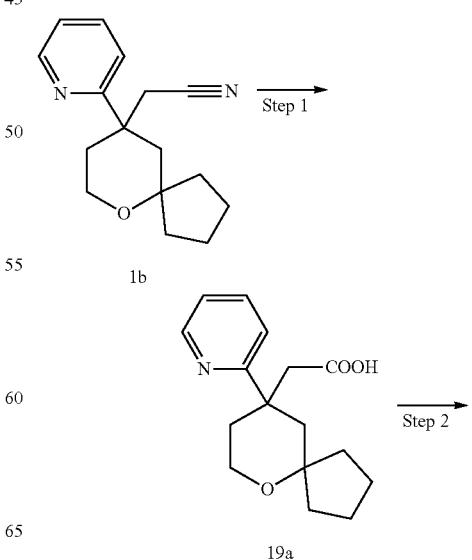

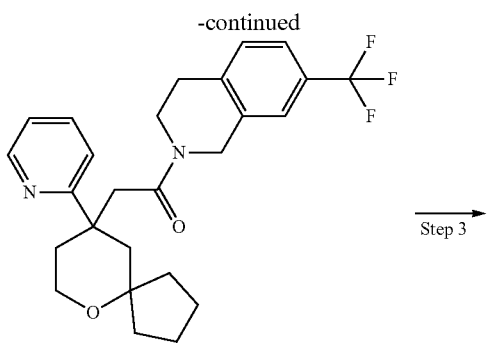

19b

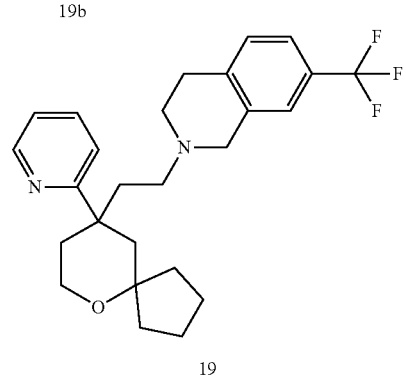

19

Step 1: Preparing 2-[9-(pyridin-2-yl)-6-oxaspiro[4.5]decan-9-yl] acetic acid (19a)

2-[9-(pyridin-2-yl)-6-oxaspiro[4.5]decan-9-yl]acetonitrile (1b, 500 mg, 2 mmol) was added to a solution of potassium hydroxide (560 mg, 10 mmol) in ethylene glycol/water (20 ml/10 ml), the reaction solution was heated to 100° C. and kept overnight. TLC test found that the raw materials disappeared, the reaction solution was cooled to room temperature, diluted with water (20 ml), and adjusted to pH=3-4 with hydrochloric acid, extracted with ethyl acetate (40 ml×3), the organic phases were combined, washed with water (50 ml), and washed with saturated saline (50 ml), dried with anhydrous sodium sulfate, and concentrated to give the yellow oily compound 2-[9-(pyridin-2-yl)-6-oxaspiro[4.5]decan-9-yl]acetic acid (19a, 320 mg), with a yield of 60%.

Step 2: Preparing 2-[9-(pyridin-2-yl)-6-oxaspiro[4.5]decan-9-yl]-1-(7-(trifluoromethyl)-3,4-dihydroisoquinoline-2(1H)-yl) ethan-1-one (19b)

1-hydroxybenzotriazole (HOBT, 135 mg, 1 mmol), 1-ethyl-(3-dimethylaminopropyl) carbodiimide hydrochloride (EDCI, 191 mg, 1 mmol) were added to a solution of 2-[9-(pyridin-2-yl)-6-oxaspiro[4.5]decan-9-yl] acetic acid (19a, 138 mg, 0.5 mmol) in dimethylformamide (DMF, 10 ml), the solution was stirred at room temperature for ten minutes under the protection of argon, and then 7-(trifluoromethyl)-1,2,3,4-tetrahydroisoquinoline (88 mg, 0.5 mmol) and diisopropylethylamine (258 mg, 2 mmol) were added thereto, the reaction was stirred at room temperature overnight, and TLC detected the disappearance of raw materials. Water (30 ml) was added to the reaction solution, and the solution was extracted with dichloromethane (30 mL×3), the organic phases were combined, washed with saturated saline (30 mL×3), dried with anhydrous sodium sulfate, concentrated, and yellow solids 2-[9-(pyridin-2-yl)-6-oxaspiro[4.5] decane-9-yl]-1- (7- (trifluoromethyl)-3,4- dihydroisoquinoline-2(1H) -yl) ethan-1-one (19b, 110 mg) were obtained by thin chromatography (DCM:MeOH=20:1), with a yield of 58%.

Step 3: Preparing 2-[2-(9-(pyridin-2-yl)-6-oxaspiro[4.5]decan-9-yl)ethyl]-7-trifluoromethyl-1,2,3,4-tetrahydroisoquinoline Lithium aluminum tetrahydride (100 mg, 2.6 mmol) was added to a solution of 2-[9-(pyridin-2-yl)-6-oxaspiro[4.5]decan-9-yl]-1-(7- (trifluoromethyl)-3,4- dihydroisoquinoline-2(1H) -yl)ethan-1-one (19 b, 110 mg, 0.28 mmol) in anhydrous tetrahydrofuran (10 ml) at 0° C., after stirring for two hours, the reaction solution was quenched with 0.1 ml of water, 0.1 ml of 15% NaOH, and 0.3 ml of water in turn. Then the reaction solution was extracted with diethyl ether (30 mL×3), dried with anhydrous sodium sulfate, concentrated and a yellow oily substance 2-[2-(9-(pyridin-2-yl)-6-oxaspiro[4.5]decan-9-yl)ethyl]-7-trifluoromethyl-1,2,3,4-tetrahydroisoquinoline (19, 35 mg) was obtained by thin chromatography (DCM:MeOH=20:1), with a yield of 35%.

1H NMR (400 MHz, CDCl$_3$) ppm 8.60 (dd, J=4.8, 1.2 Hz, 1H), 7.65 (td, J=7.6, 1.6 Hz, 1H), 7.34 (d, J=8.0 Hz, 1H), 7.22 (s, 1H), 7.18-7.13 (m, 2H), 3.81 (d, J=2.4 Hz, 1H), 3.80 (d, J=2.8 Hz, 1H), 3.54-3.43 (q, J=11.6, 14.8 Hz, 2H), 2.86 (t, J=5.6 Hz, 2H), 2.56-2.38 (m, 5H), 2.11 (td, J=12.4, 4.0 Hz, 1H), 1.98 (m, 1H), 1.87-1.65 (m, 5H), 1.57-1.41 (m, 4H), 1.14 (m, 1H), 0.76-0.69 (m, 1H). LC-MS: m/z (ES+) was calculated to be C26H31F3N2O 445 [M+1]+.

Example 20: Preparation of 7-methoxy-2-[2-(9-pyridin-2-yl-6-oxa-spiro[4.5]decan-9-yl)-ethyl]-1,2,3,4-tetrahydroisoquinolin e (H20)

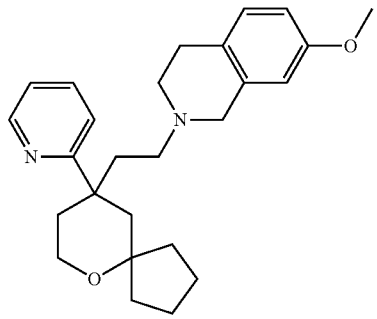 [SMILES: COc1ccc2c(c1)CN(CCC1(c3ccccn3)CCOC3(CCCC3)C1)CC2]

The preparation method was the same as that in Example 19, and the 7-trifluoromethyl-1,2,3,4-tetrahydroisoquinoline in the step 2 was replaced by 7-methoxy-1,2,3,4-tetrahydroisoquinoline to prepare 7-methoxy-2-[2-(9-pyridin-2-yl-6-oxa-spiro[4.5]decan-9-yl)-ethyl]-1,2,3,4-tetrahydroisoquinoline (20, 34 mg), with a yield of 36%, the appearance was a light yellow sticky substance.

1H NMR (400 MHz, CDCl$_3$) ppm 8.60 (dd, J=4.8, 1.2 Hz, 1H), 7.65 (td, J=7.6, 1.6 Hz, 1H), 7.35 (d, J=8.0 Hz, 1H), 7.14 (q , 1H), 6.67 (d, J=8.4 Hz, 1H), 6.68 (dd, J=8.4, 2.8 Hz, 1H), 6.50 (d, J=2.4 Hz, 1H), 3.81-3.78 (m, 2H), 3.76 (s, 3H), 3.48-3.38 (q, J=11.2, 14.4 Hz, 2H), 2.75 (t, J=6.0 Hz, 2H), 2.59-2.50 (m, 3H), 2.41-2.34 (m, 2H), 2.13-2.07 (td, J=11.6, 3.2 Hz, 1H), 1.99-1.74 (m, 6H), 1.57-1.48 (m, 4H), 1.14 (m, 1H), 0.76-0.68 (m, 1H). LC-MS: m/z (ES+) was calculated to be C26H34N2O2 407 [M+1]+.

Example 21: Preparation of {2-[9-(5-fluoro-pyridin-2-yl)-6-oxa-spiro[4.5]decan-9-yl]-ethyl}-(2-(trifluoromethoxy)-phenmeth yl)-amine (H21)

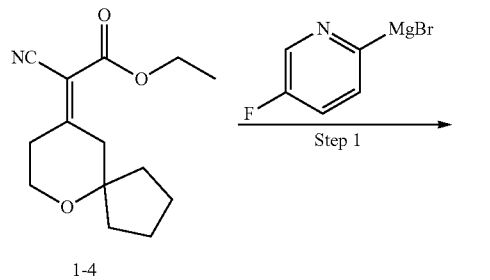

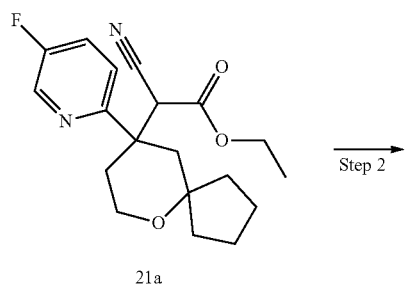

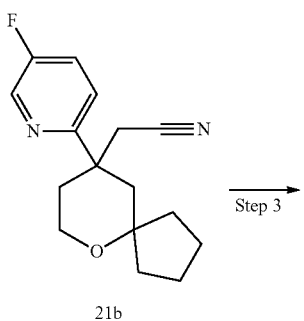

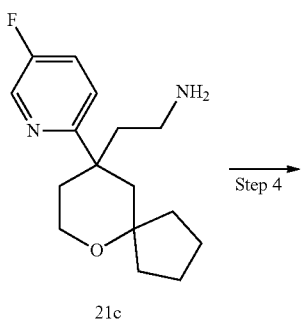

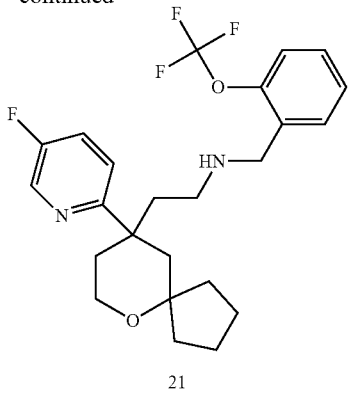

Step 1: Preparing cyano-[9-(5-fluoro-pyridin-2-yl)-6-oxa-spiro[4.5]decan-9-yl]-ethyl acetate (21a)

Tetrahydrofuran solution (6 mL, 12 mmol) containing 2.0 M isopropylmagnesium bromide was added into the reaction flask, then the solution of 2-bromo-5-fluoro-pyridine (1.0 mL, 10 mmol) in diethyl ether (4 ml) was added dropwise, and the reaction solution was stirred at room temperature for three hours to obtain the corresponding 1M Grignard reagent, 5-fluoro-2-pyridine magnesium bromide.

Anhydrous diethyl ether (10 ml) was added into a round bottom reaction flask filled with nitrogen, the Grignard reagent prepared above (1.0 M, 6 mL), cuprous iodide (96 mg, 0.5 mmol) were added, and the solution of 2-cyano-[(9Z)-6-oxaspiro[4.5]decan-9-ylidene] ethyl acetate (1-4, 1.25 g, 5 mmol) in diethyl ether (10 ml) was added dropwise into the above reaction solution in 30 minutes under ice bath, the reaction was kept stirring under an ice bath for three hours, the reaction solution was poured into 1N glacial hydrochloric acid (25 ml), extract with diethyl ether (3×50 ml), wash with saturated saline (50 ml), and dried with anhydrous sodium sulfate, concentrated and a yellow oily compound cyano-[9-(5-fluoro-pyridin-2-yl)-6-oxa-spiro[4.5]decan-9-yl]-ethyl acetate (680 mg, with a yield of 40%) was obtained by silica gel column (7% to 60% EtOAc/PE).

Step 2: Preparing 2-[9-(5-fluoro-pyridin-2-yl)-6-oxaspiro[4.5]decan-9-yl]acetonitrile (21b)

Cyano-[9-(5-fluoro-pyridin-2-yl)-6-oxa-spiro [4.5] decan-9-yl]-ethyl acetate (21a, 0.68 g, 2 mmol) was added to a solution of potassium hydroxide (112 mg, 2 mmol) in ethylene glycol (5 ml), the reaction solution was heated to 120° C. for three hours, cooled, water (50 ml) was added, extracted with diethyl ether (3×50 ml), and washed with water (50 ml), saturated saline (50 ml) in turn, dried with anhydrous sodium sulfate, concentrated and a solid compound 2-[9-(5-fluoro-pyridin-2-yl)-6-oxaspiro[4.5]decan-9-yl]acetonitrile (21b, 400 mg) was obtained by column chromatography (5% to 40% ethyl acetate/n-hexane), with a yield of 73%.

Step 3: Preparing 2-(9-(5-fluoropyridin-2-yl)-6-oxa-spiro[4.5]decan-9-yl)-ethylamine (21c)

Lithium aluminum tetrahydride (120 mg, 3 mmol) was added to a solution of the compound, 2-[9-(5-fluoro-pyridin-2-yl)-6-oxaspiro[4.5]decan-9-yl]acetonitrile (274 mg, 1.0 mmol) in anhydrous diethyl ether (10 ml) at 0° C., the reaction solution was stirred for two hours then was quenched with 0.1 ml of water, 0.1 ml of 15% NaOH, and 0.1 ml of water in turn, and extracted with diethyl ether (3×20 mL), dried with anhydrous sodium sulfate, concentrated to obtain 2-(9-(5-fluoropyridin-2-yl)-6-oxa-spiro[4.5]decan-9-yl)-ethylamine (200 mg, with a yield of 72%) as a yellow oily substance.

Step 4: Preparing {2-[9-(5-fluoro-pyridin-2-yl)-6-oxa-spiro[4.5]decan-9-yl]-ethyl}-(2-(trifluoromethoxy)-benzyl)-a mine (H21)

Magnesium sulfate (72 mg, 0.6 mmol) was added to a solution of dichloromethane (10 ml) containing 2-(9-(5-fluoropyridin-2-yl)-6-oxa-spiro[4.5]decan-9-yl)-ethylamine (21c, 70 mg, 0.25 mmol), and 2-trifluoromethoxybenzaldehyde (57 mg, 0.3 mmol) was added at room temperature. The reaction solution was stirred overnight, filtered, and the solution was concentrated, 5 ml of methanol was added at 0° C., and sodium borohydride (38 mg, 1 mmol) was added in one portion, then the reaction solution was stirred at 0° C. for one hour, quenched with water (10 ml), extracted with dichloromethane (3×20 ml), and the separated organic phase was washed with saturated saline, dried with anhydrous sodium sulfate, concentrated, and a yellow oily substance, {2-[9-(5-fluoro-pyridin-2-yl)-6-oxa-spiro[4.5]decan-9-yl]-ethyl}-(2-(trifluoromethoxy)-benzyl)-a mine (33 mg, 30%), was obtained by preparing a thin chromatography.

1H NMR (400 MHz, CDCl$_3$) ppm 1H NMR (400 MHz, CDCl$_3$) ppm 8.37 (d, J=2.8 Hz, 1H), 7.33-7.27 (m, 2H), 7.26-7.15 (m, 4H), 3.72-3.66 (m, 4H), 2.44 (td, J=11.2, 5.2 Hz, 1H), 2.36 (dd, J=14.0, 2.0 Hz, 1H), 2.27 (dd, J=13.6, 2.0 Hz, 1H), 2.44 (td, J=11.2, 4.8 Hz, 1H), 1.96-1.87 (m, 2H), 1.76-1.64 (m, 4H), 1.52-1.35 (m, 4H), 1.09 (m, 1H), 0.70-0.61 (m, 1H). LC-MS: m/z (ES+) was calculated to be C24H28F4N2O2 453 [M+1]+.

Example 22: Preparation of (2-trifluoromethoxy-benzyl)-[2-(9-pyridin-2-yl-6-oxa-spiro[4.5]decan-9-yl) -ethyl]-amine (H22)

The preparation method was the same as that in Example 1, and the 3-trifluoromethoxybenzaldehyde in the step 7 was replaced by 2-trifluoromethoxybenzaldehyde to prepare (2-trifluoromethoxybenzyl)-[2-(9-pyridin-2-yl-6-oxa-spiro[4.5]decan-9-yl) -ethyl]-amine (22, 34 mg), with a yield of 28%, the appearance was a light yellow sticky substance.

1H NMR (400 MHz, CDCl$_3$) ppm 8.54-8.52 (m, 1H), 7.59 (dd, J=1.2 Hz, 1H), 7.25-7.20 (m, 2H), 7.20-7.08 (m, 4H), 3.75-3.64 (m, 4H), 2.62-2.32 (m, 3H), 1.91-1.73 (m, 3H), 1.69-1.40 (m, 8H), 1.09 (m, 1H), 0.70-0.62 (m, 1H). LC-MS: m/z (ES+) was calculated to be C24H29F3N2O2 435 [M+1]+.

Example 23: Preparation of 6-[2-(9-pyridin-2-yl-6-oxa-spiro[4.5]decan-9-yl)-ethyl]-4,5,6,7-tetrahydro-thieno[2, 3-c]pyridine (H23)

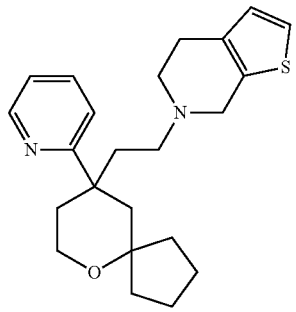 [SMILES: c1ccc(C2(CCN3CCc4ccsc4C3)CCOC3(CCCC3)C2)nc1]

The preparation method was the same as that in Example 19, and the 7-(trifluoromethyl)-1,2,3,4-tetrahydroisoquinoline in the step 2 was replaced by 4,5,6,7-tetrahydro-thieno [2,3-c]pyridine to prepare 6-[2-(9-pyridin-2-yl-6-oxa-spiro [4.5]decan-9-yl)-ethyl]-4,5,6,7-tetrahydro-thieno [2, 3-c] pyridine (23, 70 mg), with a yield of 64%, the appearance was a yellow oily substance.

1H NMR (400 MHz, CDCl$_3$) ppm 8.54-8.56 (m, 1H), 7.61 (dd, J=0.8 Hz, 1H), 7.31-7.29 (m, 1H), 7.11-7.02 (m, 2H), 6.70 (d, J=5.2 Hz, 1H), 3.78-3.71 (m, 2H), 3.54-3.52 (m, 2H), 2.62 (d, J=5.2 Hz, 4H), 2.36-2.32 (m, 3H), 2.07 (m, 1H), 1.97-1.91 (m, 2H), 1.84-1.73 (m, 4H), 1.47 (m, 2H), 1.09 (m, 1H), 0.70-0.62 (m, 1H). LC-MS: m/z (ES+) was calculated to be C23H30N2OS 383 [M+1]+.

Example 24: Preparation of 3-methylamino-thiophene-2-carboxylic acid [2-(9-pyridin-2-yl-6-oxa-spiro[4.5]decan-9-yl)-ethyl]-amide (H24)

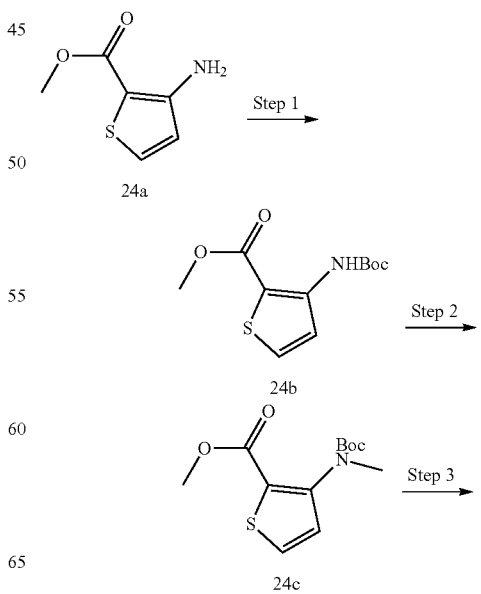

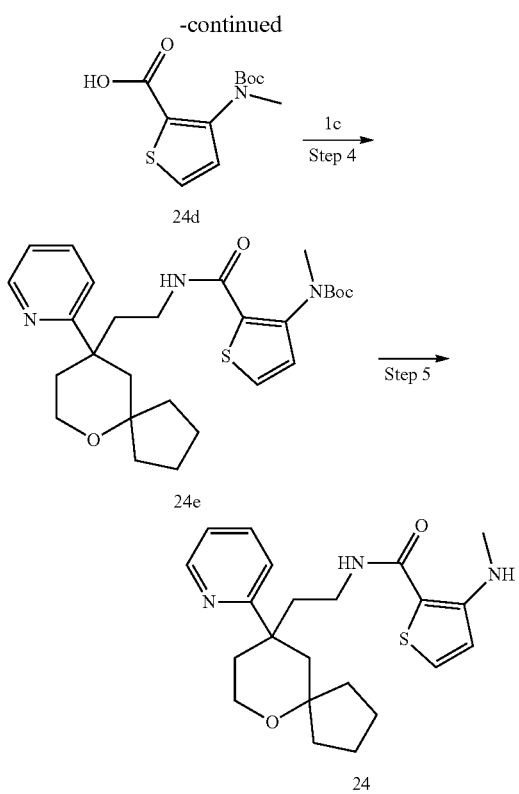

Step 1: Preparing 3-(tert-butoxycarboxamido) thiophene-2-formic acid methyl ester (24b)

Triethylamine (6.4 g, 64 mmol) and di-tert-butyl dicarbonate (8.3 g, 38 mmol) were added to a solution of the compound 2-aminothiophene-2-formic acid methyl ester (24a, 5 g, 31.8 mmol) in tetrahydrofuran (70 ml) at 0° C., the reaction solution was stirred overnight at room temperature, and the reaction solution was concentrated, diluted with water (100 mL), extracted with ethyl acetate (100 ml×3), the organic phases were combined, and the obtained organic phase was sequentially washed with water (100 mL) and saturated saline (100 mL), dried with anhydrous sodium sulfate, and concentrated to obtain 3-(tert-butoxycarboxamido) thiophene-2-formic acid methyl ester (24b, 7.5 g) as a yellow solid compound, with a yield of 92%.

Step 2: Preparing 3-((tert-butoxyformyl)(methyl) amino)thiophene-2-formic acid methyl ester (24c)

The compound 3-(tert-butoxycarboxamido)thiophene-2-formic acid methyl ester (24b, 5.2 g, 20 mmol) was dissolved in tetrahydrofuran (70 ml), and sodium hydride (960 mg, 24 mmol) was added under ice bath. The reaction solution was stirred for 30 minutes under ice bath, and then iodomethane (3.4 g, 24 mmol) was added dropwise. The reaction solution was stirred at room temperature overnight, quenched with saturated ammonium chloride, and extracted with ethyl acetate (100 ml×3), the organic phase was sequentially washed with water (30 mL×2) and saturated saline (30 mL), dried with anhydrous sodium sulfate, concentrated, and a yellow oily substance 3-((tert-butoxyformyl)(methyl)amino)thiophene-2-formic acid methyl ester (24c, 2.8 g) was obtained by silica gel column (PE:EA=100:1-3:1), with a yield of 51%.

Step 3: Preparing 3-((tert-butoxyformyl)(methyl) amino)thiophene-2-formic acid (24d)

The compound 3-((tert-butoxyformyl)(methyl)amino) thiophene-2-formic acid methyl ester (24c, 1.3 g, 5 mmol) was dissolved in ethanol (20 ml), and aqueous solution of sodium hydroxide (4 M, 10 mL, 40 mmol) was added. The reaction solution was stirred at room temperature overnight and the reaction solution was concentrated, diluted with water (10 mL), adjusted the pH to 3, then extracted with ethyl acetate (50 ml×3), the obtained organic phase was washed with water (50 mL×2) and saturated saline (50 mL) sequentially, dried with anhydrous sodium sulfate, and concentrated to obtain a yellow solid 3-((tert-butoxyformyl) (methyl)amino)thiophene-2-formic acid (24d, 1.1 g, with a yield of 92%).

Step 4: Preparing tert-butylmethyl(2-((9-(pyridin-2-yl)-6-oxa-spiro[4.5]decan-9-yl)-ethyl)carbamoyl) thiophen-3-yl) carbamic acid ester (24e)

HOBT (135 mg, 1 mmol) and EDCI (191 mg, 1 mmol) were added to a solution of 3-((tert-butoxyformyl)(methyl) amino)thiophene-2-carboxylic acid (24d, 122 mg, 0.5 mmol) in dichloromethane (20 mL), the solution was stirred at room temperature for ten minutes under the protection of argon, then 2-(9-(pyridin-2-yl)-6-oxaspiro[4.5]decan-9-yl) ethylamine (1c, 130 mg, 0.5 mmol) and diisopropylethylamine (258 mg, 2 mmol) were added, and the reaction solution was stirred at room temperature overnight and the raw materials was found to be disappeared by the point plate of TLC (DCM:MeOH=20:1, Rf=0.4). Water (30 mL) was added to the reaction solution, extracted with dichloromethane (30 mL×3), the organic phases were combined, and the obtained organic phase was washed with water (30 mL) and saturated saline (30 mL) sequentially, and dried with anhydrous sodium sulfate, concentrated, and a yellow solid tert-butylmethyl (2-((9-(pyridin-2-yl)-6-oxa-spiro[4.5]decan-9-yl)-ethyl) carbamoyl)thiophen-3-yl)carbamic acid ester (24e, 170 mg) was obtained by thin chromatography (DCM:MeOH=20:1), with a yield of 68%.

Step 5: Preparing 3-methylamino-thiophene-2-carboxylic acid [2-(9-pyridin-2-yl-6-oxa-spiro[4.5] decan-9-yl)-ethyl]-amide (H24)

Trifluoroacetic acid (2 mL) was added to a solution of tert-butylmethyl(2-((9-(pyridin-2-yl)-6-oxa-spiro[4.5]decan-9-yl)-ethyl)carbamoyl)thiophen-3-yl) carbamic acid ester (24e, 150 mg, 0.3 mmol) in dichloromethane (2 ml), and the reaction solution was stirred overnight, then the reaction solution was concentrated, diluted with water (10 ml), and the pH was adjusted to 9-10, then the reaction solution was extracted with ethyl acetate (30 ml×3), the organic phases were combined, and the obtained organic phase was washed with water (30 mL×2), washed with saturated saline (30 mL), dried with anhydrous sodium sulfate, concentrated, and the yellow solid compound 24 (90 mg, with a yield of 75%) was obtained by silica gel column (DCM:MeOH=100:1-10:1).

1H NMR (400 MHz, CDCl$_3$) ppm 8.55 (d, J=4.8 Hz, 1H), 7.90 (d, J=8.0 Hz, 1H), 7.66 (d, J=8.4 Hz, 1H), 7.28-7.22 (m, 1H), 7.10 (s, 1H), 6.55 (d, J=7.2 Hz, 1H), 6.07 (t, J=0.6 Hz, 1H), 3.83-3.75 (m, 2H), 3.41-3.44 (m, 1H), 3.24-3.21 (m, 1H), 2.89 (s, 3H), 2.59-2.56 (m, 2H), 2.27 (d, J=1.2 Hz, 1H), 2.09-2.03 (m, 1H), 1.94-1.81 (m, 2H), 1.52-1.40 (m, 7H), 1.09 (m, 1H), 0.70-0.62 (m, 1H). LC-MS: m/z (ES+) was calculated to be C22H29N3O2S 400 [M+1]+.

Example 25: Preparation of [(5-methoxy-1H-pyrazol-4-yl)methyl]-[2-(9-(pyridin-2-yl)-6-oxaspiro[4.5]decan-9-yl) ethyl] amine (H25)

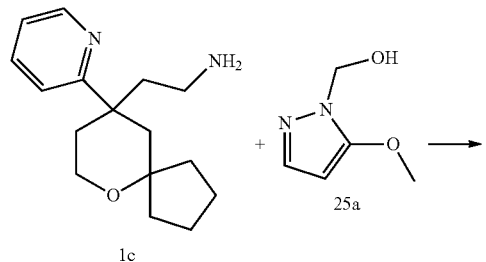

2-(9-(pyridin-2-yl)-6-oxaspiro[4.5]decan-9-yl)ethylamine (1c, 70 mg, 0.27 mmol), (5-methoxy-1H-pyrazol-1-yl) methanol (35 mg, 0.27 mmol) and p-toluenesulfonic acid monohydrate (TsOH.H2O, 10 mg, 0.054 mmol) were dissolved in dichloromethane (3 mL) and heated under reflux for 16 hours. Saturated aqueous sodium bicarbonate solution (30 mL) was added to the reaction solution, and the reaction solution was extracted with dichloromethane (15 mL×3), after combination, the organic layer was dried and concentrated, and separated and purified by preparative HPLC to obtain the compound [(5-methoxy-1H-pyrazol-4-yl) methyl]-[2-(9-(pyridin-2-yl)-6-oxaspiro[4.5]decan-9-yl) ethyl amine (20 mg, yellow oily substance), with a yield of 7%.

1H NMR (400 MHz, CDCl3) ppm 8.62 (dd, J=1.2 Hz, 1H), 8.00-7.96 (m, 1H), 7.65 (d, J=8.4 Hz, 1H), 7.50 (s, 1H), 7.45-7.42 (m, 1H), 3.86-3.85 (m, 5H), 3.75-3.73 (m, 2H), 2.93-2.85 (m, 1H), 2.49-2.31 (m, 3H), 2.15-2.07 (m, 1H), 1.92-1.42 (m, 9H), 1.52-1.40 (m, 7H), 1.13-1.07 (m, 1H), 0.75-0.67 (m, 1H). LC-MS: m/z (ES+) was calculated to be $C_{21}H_{30}N_4O_2$ 371 [M+1]+.

Example 26: Preparation of ((3-methoxythiophen-2-yl)methyl)-2-(9-(pyridin-2-yl)-6-oxaspiro[4.5]decan-9-yl)propyl]-1-amin e (H26)

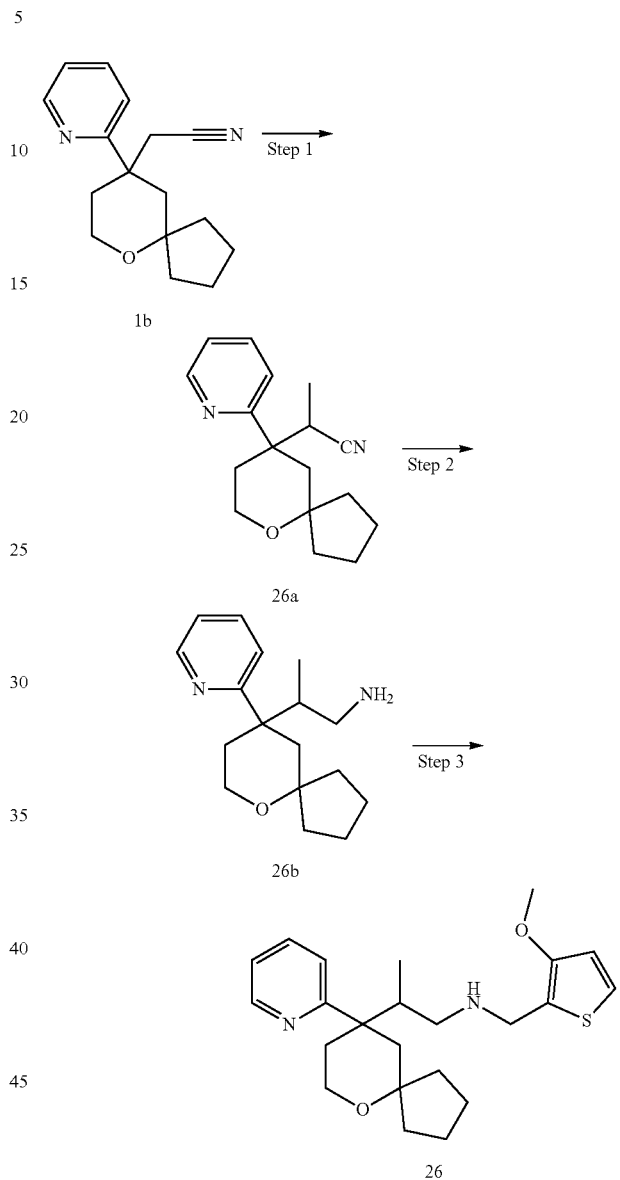

Step 1: Preparing 2- [9- (pyridin-2-yl)-6-oxaspiro [4.5] decan-9-yl] propionitrile (26a)

2-[9-(pyridin-2-yl)-6-oxaspiro[4.5]decan-9-yl]acetonitrile (1b, 0.256 g, 1 mmol) was dissolved in anhydrous N, N-dimethylformamide (10 mL), cooled to 0° C., sodium hydride (60 mg, 1.5 mmol) was added thereto, the reaction was continued at 0° C. for 30 minutes, then methyl iodide (284 mg, 2 mmol) was added, and the mixture was slowly warmed to room temperature and kept overnight. The reaction solution was quenched by adding ice water (10 mL) thereto, and extracted with ethyl acetate (15 mL×3), the organic layer was washed with water (15 mL×3), washed with saturated sodium chloride (15 mL), dried and concentrated, the yellow solid compound 2-[9-(pyridin-2-yl)-6-oxaspiro[4.5]decan-9-yl] propionitrile (26a, 0.2 g) was obtained by silica gel column (developing solvent was 5% to 40% ethyl acetate/n-hexane), yield 74%.

Step 2: Preparing 2-(9-(pyridin-2-yl)-6-oxaspiro [4.5]decan-9-yl) propan-1-amine (26b)

Lithium aluminum tetrahydride (120 mg, 3 mmol) was added dropwise to a solution of 2-[9-(pyridin-2-yl)-6-oxaspiro[4.5]decan-9-yl]propionitrile (26a, 270 mg, 1.0 mmol) in anhydrous diethyl ether (15 ml) at 0° C. After 2 hours, water (0.1 ml) and 15% aqueous sodium hydroxide solution (0.1 ml) were added to the reaction solution respectively, then quenched with water (0.1 ml). The reaction mixture was extracted with diethyl ether (3×20 ml), dried with anhydrous magnesium sulfate, filtered and followed by concentration to obtain 2-(9-(pyridin-2-yl)-6-oxaspiro[4.5]decan-9-yl)propan-1-amine (26b, 200 mg), yield 73%, as a yellow oily substance, which was used without further purification.

Step 3: Preparing ((3-methoxythiophen-2-yl) methyl)-2-(9-(pyridin-2-yl)-6-oxaspiro[4.5]decan-9-yl)propyl]-1-amin e (H26)

2-(9-(pyridin-2-yl)-6-oxaspiro[4.5]decan-9-yl)propan-1-amine (26b, 137 mg, 0.5 mmol) and anhydrous magnesium sulfate (72 mg, 0.6 mmol) were added to anhydrous dichloromethane (8 ml), and 3-methoxythiophene-2-aldehyde (78 mg, 0.55 mmol) was added, the mixture was stirred at room temperature overnight. The reaction solution was filtered, and the filtrate was concentrated then added to anhydrous methanol (5 ml), sodium borohydride (38 mg, 1 mmol) was added at 0° C., 1 hour later, water (10 ml) was added, and the system was extracted with dichloromethane (3×20 ml), washed with saturated saline (10 ml), and dried with anhydrous sodium sulfate, then purified by thin layer chromatography (developing solvent was 0-10% dichloromethane/methanol) to obtain the compound ((3-methoxythiophen-2-yl)methyl)-2-(9-(pyridin-2-yl)-6-oxaspiro[4.5]decan-9-yl)propyl]-1-amine (26,100 mg), with a yield of 50%.

1H NMR (400 MHz, CDCl$_3$) ppm 8.54 (dd, J=4.8, 0.8 Hz, 1H), 7.62 (td, J=7.6, 2.0 Hz, 1H), 7.24 (d, J=8.0 Hz, 1H), 7.18 (d, J=5.2 Hz, 1H), 7.12-7.06 (qd, J=4.8, 1.2 Hz, 1H), 6.85 (d, J=5.3 Hz, 1H), 3.78 (m, 5H), 3.74-3.71 (m, 2H), 2.53 (td, J=10.8, 5.2 Hz, 1H), 2.42-2.30 (m, 2H), 2.12 (td, J=11.2, 5.2 Hz, 1H), 2.01-1.94 (m, 1H), 1.89 (d, J=13.6 Hz, 1H), 1.77-1.60 (m, 3H), 1.50-1.35 (m, 4H), 1.08 (m, 4H), 0.70-0.64 (m, 1H). LC-MS: m/z (ES+) was calculated to be $C_{23}H_{32}N_2O_2S$ 401 [M+1]$^+$.

Example 27: Preparation of ((3-methoxythiophen-2-yl)methyl)-1-(9-(pyridin-2-yl)-6-oxaspiro[4.5]decan-9-yl)propyl]-2-amin e (H$_{27}$)

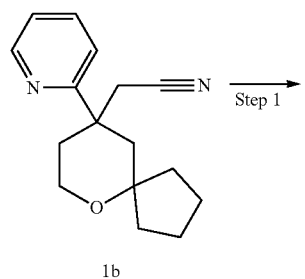

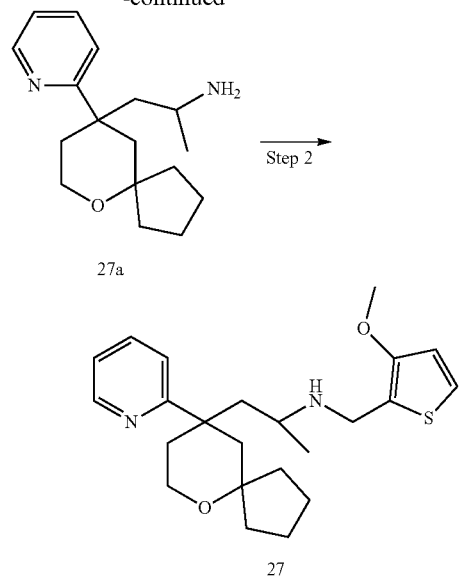

Step 1: Preparing 1-(9-(pyridin-2-yl)-6-oxaspiro [4.5]decan-9-yl) propan-2-amine (27a)

2-[9-(pyridin-2-yl)-6-oxaspiro[4.5]decan-9-yl]acetonitrile (1b, 0.256 g, 1 mmol) was dissolved in anhydrous tetrahydrofuran (10 mL) and cooled to −78° C., methyllithium (0.94 ml, 1.5 mmol, 1.6 M of diethyl ether solution) was slowly added dropwise thereto. After the addition, the reaction was continued for one hour at −78° C., and quenched by slowly adding methanol (10 ml), then slowly warmed to room temperature and continued stirring for 2 hours. The reaction solution was quenched by adding ice water (10 mL), and extracted with ethyl acetate (15 mL×3), the organic layer was washed with water (15 mL×3) and then with saturated sodium chloride (15 mL), dried and concentrated. The concentrated reaction solution was dissolved by adding methanol, and 10% palladium carbon (10 mg) was added, hydrogen was inlet, and the reaction was conducted at room temperature overnight. After filtration, the solvent was evaporated to dryness to obtain 1-(9-(pyridin-2-yl)-6-oxaspiro[4.5]decan-9-yl) propan-2-amine (27a) as a yellow oily substance (27a, 0.15 g), with a yield of 55%, which was used without further purification.

Step 2: Preparing ((3-methoxythiophen-2-yl) methyl)-1-(9-(pyridin-2-yl)-6-oxaspiro[4.5]decan-9-yl)propyl]-2-amin e (H$_{27}$)

2- (9-(pyridin-2-yl)-6-oxaspiro[4.5]decan-9-yl)propan-1-amine (26b) was replace by 1-(9-(pyridin-2-yl)-6-oxaspiro[4.5]decan-9-yl)propan-2-amine (27a), the ((3-methoxythiophen-2-yl)methyl)-1-(9-(pyridin-2-yl)-6-oxaspiro[4.5]decan-9-yl)propyl]-2-amin e (27, 34 mg) was prepared by the procedure described in the preparation of Example 26, with a yield of 28%, and the appearance was a light yellow sticky substance.

1H NMR (400 MHz, CDCl$_3$) ppm 8.55 (dd, J=4.8, 1.2 Hz, 1H), 7.61 (td, J=7.6, 2.0 Hz, 1H), 7.32 (d, J=8.0 Hz, 1H), 7.24 (d, J=5.2 Hz, 1H), 7.10-7.06 (qd, J=4.8, 1.2 Hz, 1H), 6.93 (d, J=5.2 Hz, 1H), 6.44 (s, 1H), 4.63 (s, 2H), 3.76-3.73 (m, 1H), 3.34-3.26 (m, 1H), 2.99-2.90 (m, 1H), 2.47 (dd, J=13.6, 2.0 Hz, 1H), 2.38 (dd, J=13.6, 2.0 Hz, 1H), 2.13-

2.05 (m, 1H), 1.90 (d, J=13.6 Hz, 2H), 1.83-1.58 (m, 5H), 1.53-1.44 (m, 3H), 1.09 (m, 4H), 0.71-0.64 (m, 1H). LC-MS: m/z (ES+) was calculated to be $C_{23}H_{32}N_2O_2S$ 401 [M+1]$^+$.

Example 28: Preparation of (3-bromo-2-trifluoromethoxybenzyl)-[2-(9-pyridin-2-yl-6-oxa-spiro[4.5]decan-9-yl)-ethyl]-amine (H$_{28}$)

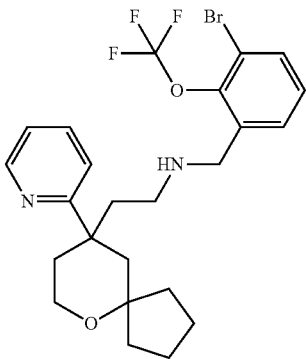 [SMILES: FC(F)(F)Oc1c(Br)cccc1CNCCC1(c2ccccn2)CCOC2(CCCC2)C1]

The preparation method was the same as that in Example 1, the 3-trifluoromethoxybenzaldehyde in the step 7 was replaced by 2-trifluoromethoxy-3-bromobenzaldehyde to prepare (3-bromo-2-trifluoromethoxybenzyl)-[2-(9-pyridin-2-yl-6-oxa-spiro[4.5]decan-9-yl)-ethyl]-amine (28, 35 mg) with a yield of 55%, and the appearance was a light yellow sticky substance.

1H NMR (400 MHz, CD$_3$OD): δ 8.50 (d, J=3.6 Hz, 1H), 7.77-7.73 (m, 1H), 7.62-7.60 (m, 1H), 7.46 (d, J=8.0 Hz, 1H), 7.38 (d, J=7.6 Hz, 1H), 7.24-7.21 (m, 2H), 3.80-3.71 (m, 4H), 2.49-2.38 (m, 3H), 2.05-1.87 (m, 3H), 1.77-1.38 (m, 8H), 1.13-1.08 (m, 1H), 0.77-0.69 (m, 1H). LC-MS: m/z (ES+) was calculated to be $C_{24}H_{28}BrF_3N_3O_2$ 513.1 [M+1]$^+$.

Example 29: Preparation of {2-[9-(5-fluoro-pyridin-2-yl)-6-oxa-spiro[4.5]decan-9-yl]-ethyl}-(2-(difluoromethoxy)-benzyl)-amine (H$_{29}$)

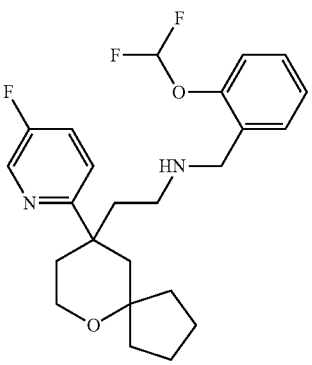 [SMILES: Fc1ccc(C2(CCNCc3ccccc3OC(F)F)CCOC3(CCCC3)C2)nc1]

The preparation method was the same as that in Example 21, the 2-trifluoromethoxybenzaldehyde in the step 4 was replaced by 2-difluoromethoxybenzaldehyde to prepare {2-[9-(5-fluoro-pyridin-2-yl)-6-oxa-spiro[4.5]decan-9-yl]-ethyl}-(2-(difluoromethoxy)-benzyl)-amine (29, 22 mg), with a yield of 18%, and the appearance was a yellow sticky substance.

1H NMR (400 MHz, CDCl$_3$) δ 8.38 (dd, J=3.0, 0.6 Hz, 1H), 7.35-7.24 (m, 4H), 7.13 (td, J=7.5, 1.2 Hz, 1H), 7.09-7.03 (m, 1H), 3.80-3.64 (m, 4H), 2.50 (td, J=11.2, 5.2 Hz, 1H), 2.37 (dd, J=13.7, 2.9 Hz, 1H), 2.28 (dd, J=13.9, 2.1 Hz, 1H), 2.09 (td, J=11.2, 4.8 Hz, 1H), 2.02-1.88 (m, 2H), 1.84-1.61 (m, 4H), 1.55-1.36 (m, 4H), 1.10 (dd, J=14.2, 6.6 Hz, 1H), 0.66 (dt, J=13.5, 9.0 Hz, 1H). LC-MS: m/z (ES+) was calculated to be $C_{24}H_{29}F_3N_2O_2$ 435.2 [M+1]$^+$.

Example 30: Preparation of {2-[9-(5-fluoro-pyridin-2-yl)-6-oxa-spiro[4.5]decan-9-yl]-ethyl}-((3-chlorothiophen-2-yl)-methyl)-amine (H30)

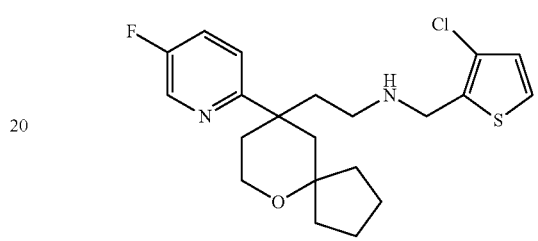

The preparation method was the same as that in Example 21, the 2-trifluoromethoxybenzaldehyde in the step 4 was replaced by 3-chlorothiophene formaldehyde to prepare {2-[9-(5-fluoro-pyridin-2-yl)-6-oxa-spiro[4.5]decan-9-yl]-ethyl}-((3-chlorothiophen-2-yl)-methyl)-amine (30, 46 mg), with a yield of 59%, and the appearance was a light yellow sticky substance.

1H NMR (400 MHz, CDCl$_3$) ppm 8.40 (dd, J=2.8 Hz, 1H), 7.31-7.36 (td, J=8.4, 3.2 Hz, 1H), 7.28-7.29 (d, J=4.4 Hz, 1H), 7.14-7.15 (d, J=5.6 Hz, 1H), 6.82-6.84 (d, J=5.6 Hz, 1H), 3.68-3.78 (m, 4H), 2.46-2.53 (td, J=11.2, 5.6 Hz, 1H), 2.38-2.42 (m, 1H), 2.28-2.32 (m, 1H), 2.07-2.14 (td, J=11.2, 5.6 Hz, 1H), 1.90-1.97 (m, 2H), 1.60-1.78 (m, 6H), 1.39-1.49 (m, 3H), 1.09-1.14 (m, 1H), 0.63-0.71 (m, 1H). LC-MS: m/z (ESI+) was calculated to be $C_{21}H_{26}ClFN_2OS$ 409.1 [M+1]$^+$.

Example 31: Preparation of {2-[9-(5-fluoro-pyridin-2-yl)-6-oxa-spiro[4.5]decan-9-yl]-ethyl}-(3,4-dimethyl-benzyl)-amine (H$_{31}$)

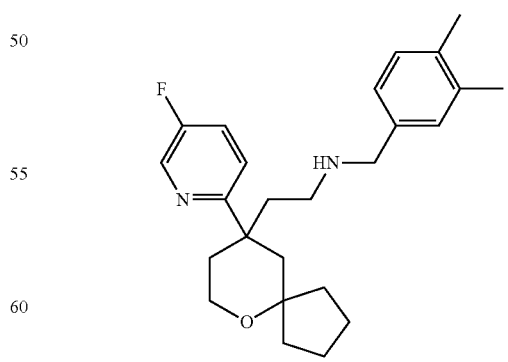

The preparation method was the same as that in Example 21, the 2-trifluoromethoxybenzaldehyde in the step 4 was replaced by 3,4-dimethylbenzaldehyde to prepare {2-[9-(5-fluoro-pyridin-2-yl)-6-oxa-spiro[4.5]decan-9-yl]-ethyl}-(3, 4-dimethyl-benzyl)-amine (31, 108 mg), with a yield of 38%, and the appearance was a yellow sticky substance.

$^1$H NMR (400 MHz, CDCl3) δ 8.31-8.25 (m, 1H), 7.35-7.23 (m, 2H), 7.06 (s, 1H), 7.03 (d, J=1.2 Hz, 2H), 3.75-3.61 (m, 4H), 2.71-2.57 (m, 1H), 2.31-2.20 (m, 2H), 2.20 (s, 1H), 2.18 (s, 3H), 2.16 (s, 4H), 2.04-1.96 (m, 1H), 1.87 (d, J=13.6 Hz, 1H), 1.73 (t, J=9.2 Hz, 1H), 1.69-1.58 (m, 1H), 1.52-1.31 (m, 4H), 1.03 (s, 1H), 0.59 (dt, J=13.3, 8.7 Hz, 1H). LC-MS: m/z (ES+) was calculated to be $C_{25}H_{33}FN_2O$ 397.3 $[M+1]^+$.

Example 32: Preparation of {2-[9-(5-fluoro-pyridin-2-yl)-6-oxa-spiro[4.5]decan-9-yl]-ethyl}-(3-chloro-2-methyl-benzyl)-amine (H32)

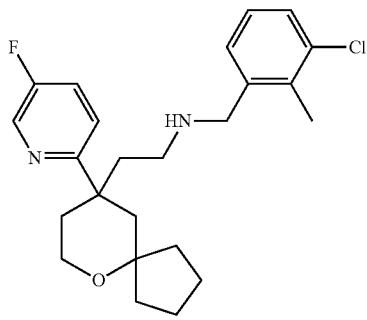 [SMILES: Cc1c(Cl)cccc1CNCCC1(c2ccc(F)cn2)CCOC2(CCCC2)C1]

The preparation method was the same as that in Example 21, the 2-trifluoromethoxybenzaldehyde in the step 4 was replaced by 3-chloro-2-methylbenzaldehyde to prepare {2-[9-(5-fluoro-pyridin-2-yl)-6-oxa-spiro[4.5]decan-9-yl]-ethyl}-(3-chloro-2-methyl-benzyl)-amine (32, 35 mg), with a yield of 29%, and the appearance was a yellow sticky substance.

$^1$H NMR (400 MHz, CDCl$_3$) δ 8.38 (d, J=2.9 Hz, 1H), 7.32 (ddd, J=8.8, 8.0, 2.9 Hz, 1H), 7.25 (d, J=8.2 Hz, 1H), 7.24-7.20 (m, 1H), 7.10-6.96 (m, 2H), 3.76-3.66 (m, 2H), 3.60 (s, 2H), 2.49 (td, J=11.2, 5.3 Hz, 1H), 2.38 (ddt, J=8.1, 5.4, 2.7 Hz, 1H), 2.32-2.23 (m, 4H), 2.09 (td, J=11.2, 4.9 Hz, 1H), 2.00-1.86 (m, 2H), 1.79-1.56 (m, 5H), 1.53-1.33 (m, 5H), 1.08 (dd, J=13.6, 6.4 Hz, 1H), 0.64 (dt, J=13.6, 8.9 Hz, 1H). LC-MS: m/z (ES+) was calculated to be $C_{24}H_{30}ClFN_2O$ 417.1 $[M+1]^+$.

Example 33: Preparation of {2-[9-(5-fluoro-pyridin-2-yl)-6-oxa-spiro[4.5]decan-9-yl]-ethyl}-((3-difluoromethoxythiophen-2-yl)-methyl)-amine (H$_{33}$)

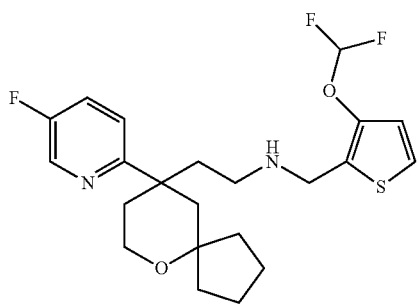 [SMILES: Fc1ccc(C2(CCNCc3sccc3OC(F)F)CCOC3(CCCC3)C2)nc1]

The preparation method was the same as that in Example 21, and the 2-trifluoromethoxybenzaldehyde in the step 4 was replaced by 2-difluoromethoxythiophene formaldehyde to prepare {2-[9-(5-fluoro-pyridin-2-yl)-6-oxa-spiro[4.5]decan-9-yl]-ethyl}-((3-difluoromethoxythiophen-2-yl)-methyl)-amine (33, 58 mg) with a yield of 36%, and the appearance was a light yellow sticky substance.

1H NMR (400 MHz, CDCl$_3$) δ 8.36 (d, J=2.8 Hz, 1H), 7.36-7.25 (m, 2H), 7.14 (d, J=5.5 Hz, 1H), 6.82-6.78 (m, 1H), 6.44 (t, J=73.7 Hz, 1H), 3.81 (s, 2H), 3.77-3.62 (m, 2H), 2.59-2.47 (m, 1H), 2.36 (d, J=13.5 Hz, 1H), 2.30-2.23 (m, 1H), 2.13 (td, J=11.3, 4.7 Hz, 1H), 2.04-1.92 (m, 1H), 1.84-1.56 (m, 5H), 1.44 (qd, J=18.0, 16.4, 6.6 Hz, 4H), 1.14-1.01 (m, 1H), 0.70-0.57 (m, 1H). LC-MS: m/z (ES+) was calculated to be $C_{22}H_{27}F_3N_2O_2S$ 441.2 $[M+1]^+$.

Biological Experiment

Experiment 1: Test of Agonistic Effects of the Compounds of the Present Invention on MOR, KOR, and DOR Opioid Receptors 1. Purpose and Method of the Experiment The purpose of the experiment was to test the agonistic effects of the compounds of the present invention on μ opioid receptor (MOR), κ opioid receptor (KOR) and δ opioid receptor (DOR), and to evaluate in vitro activity of the compounds according to the half-maximal effect concentration ($EC_{50}$).

1.1 Cell Culturing and the Preparation of Cell Plate

This test was performed using HEK293 cell lines (the stably expressed cell lines were provided by WuXi AppTec) which stably expressed μ opioid receptor, δ opioid receptor or κ opioid receptor respectively. Before the experiment, the cells were quickly thawed in water bath at 37° C., and transferred to a 50 ml conical tube, the DMEM-based cell culture medium (Invitrogen, Cat #11960) was added until 45 ml. The cells were centrifuged at 1000 rpm for 5 minutes at room temperature to precipitate. The supernatant was sucked out, be careful not to suck out cells. The precipitate was flicked into the loose cells and resuspend in 45 ml DMEM medium. The Vi-CELL XR automatic cell viability detector (BECKMAN COULTER) was used to count the cells, and the cell concentration was adjusted to $10 \times 10^5$ cells/ml based on the counting results. 20 μl of cell suspension ($20 \times 10^3$ cells/well) was transferred into a 384-well microplate (Greiner, #781280), and the plate was placed in a 5% $CO_2$ incubator (Thermo) at 37° C. overnight.

1.2 Preparation of the Solution of FLIPR Calcium Flow-4 Detection Kit (Thermo Fisher Scientific (China) Co., Ltd., Article Number $F_{30206}$)

Preparation of probenecid mother solution: 1 ml of FLIPR test solution was added to 77 mg probenecid to prepare a 250 mM solution. The solution was freshly prepared just before use.

Preparation of 2× (8 uM) Fluo-4 Direct™ loading buffer: a bottle of Fluo-4 Direct™ crystals (F10471, supplied in the kit) was thawed, and 10 ml of FLIPR test buffer (provided in the kit) was added into the sample bottle, and 0.2 ml of probenecid mother solution was added, the final concentration of probenecid was determined to be 2.5 mM, vortexed and left for 10 minutes (protected from light). The solution was freshly prepared just before use.

1.3 Preparation of the Compounds and Preparation of the Compound Plate

The test compounds H01-H$_{33}$, morphine and the corresponding positive drugs (which were DMAGO, DPDPE, U69593, respectively) were subjected to gradient dilution into 10 concentrations in 100% DMSO by the Echo-550 instrument (Labcyte), starting from 1200 nM, 4 fold gradient, with the concentration ranging from 0.004578 nM-1200 nM. The 900 nl of the compound solutions with the gradient concentration as above was transferred to a 384-well compound plate for later use (Greiner, #781280).

The positive drugs used in this experiment were: DMAGO ([D-Ala, NMePhe, Gly-ol] -enkephalin, 78123-71-4, tocris) for μopioid receptor; DPDPE ([D-Pen, D-Pen]-enkephalin, 88373-73-3, Jill Biochemical Co., Ltd.) for δ opioid receptor, U69593 (96744-75-1, Sigma) for κ opioid receptor.

1.4 Fluorescence Image Plate Reader (FLIPR) Detection

The cell plate prepared above was removed from the incubator and 20 ul 2× Fluo-4 Direct™ buffer was added thereto. The final volume in the cell plate was 40 λl. The plate was incubated at 37° C., under 5% $CO_2$ for 50 minutes, and incubated at room temperature for 10 minutes, then was placed into the FLIPR instrument (MD), and the compound plate and pipette box was placed into. The protocol was run on the FLIPRTETRA platform, 10 μl of positive drug or the test compound was transfered to the cell plate from the compound plate, and the fluorescent signal was read.

1.5 Data Processing and Statistics

The signal value generated by each well was calculated, and the calculation formula was that: the activity %=(signal value of the test compound−signal value of the solvent)/(signal value of the positive drug−signal value of the solvent). The data statistics and graphs of the percentage of the activity and the concentration of the corresponding compound were made by the agonist formula in the Graph Pad 7.0 software, the $EC_{50}$ value was calculated, as shown in the table below.

2. Test Results and Conclusions

The specific $EC_{50}$ values measured for the activity of the compounds of the present invention on MOR, DOR, and KOR receptors are shown in Table 1 below. As can be seen from Table 1, the agonistic effect of the compounds of the present invention on MOR receptors was better than that of morphine. In addition, the compounds of the present invention has weak agonistic activity on DOR and KOR, strong agonistic activity on MOR, and high selectivity to MOR receptors.

TABLE 1

$EC_{50}$ values of MOR, DOR, and KOR receptors after agonism using the compounds of the present invention

| Compound Number | $EC_{50}$ (nM) | | |
|---|---|---|---|
| | MOR | DOR | KOR |
| morphine | 30.10 | 10000 | 10000 |
| H01 | 6.71 | 10000 | 10000 |
| H02 | 9.91 | 10000 | 10000 |
| H03 | 6.47 | 10000 | 10000 |
| H04 | 6.05 | 10000 | 10000 |
| H05 | 7.05 | 10000 | 10000 |
| H06 | 6.10 | 10000 | 10000 |
| H07 | 3.15 | 10000 | 10000 |
| H08 | 3.42 | 10000 | 10000 |
| H09 | 4.12 | 10000 | 10000 |
| H10 | 2.15 | 10000 | 10000 |
| H11 | 2.08 | 10000 | 10000 |
| H12 | 2.04 | 10000 | 10000 |
| H13 | 5.16 | 10000 | 10000 |
| H14 | 2.10 | 10000 | 10000 |
| H15 | 3.32 | 10000 | 10000 |
| H16 | 9.06 | 10000 | 10000 |
| H17 | 8.68 | 10000 | 10000 |
| H18 | 7.32 | 10000 | 10000 |
| H19 | 5.43 | 10000 | 10000 |
| H20 | 3.53 | 10000 | 10000 |
| H21 | 4.02 | 10000 | 10000 |
| H22 | 1.04 | 10000 | 10000 |
| H23 | 4.08 | 10000 | 10000 |
| H24 | 10.68 | 10000 | 10000 |
| H25 | 2.02 | 10000 | 10000 |
| H26 | 1.76 | 10000 | 10000 |
| H27 | 4.01 | 10000 | 10000 |
| H28 | 6.35 | 10000 | 10000 |
| H29 | 6.09 | 10000 | 10000 |
| H30 | 5.62 | 10000 | 10000 |
| H31 | 3.83 | 10000 | 10000 |
| H32 | 7.35 | 10000 | 10000 |
| H33 | 5.25 | 10000 | 10000 |

Experiment 2: Test of the Agonistic Effect of the Compounds of the Present Invention on the cAMP Pathway of MOR Receptor

1. Purpose and Method of the Experiment

The purpose of this experiment was to test the agonistic effect of the compounds of the invention on the cAMP pathway of MOR and to evaluate the in vitro activity of the compounds according to $EC_{50}$.

1.1 Experimental Principles and Techniques

In this experiment, HitHunter cAMP Assay EFC technology of DiscoverX was used to measure the cAMP level in cells and monitor the functional status of G-protein coupled receptors (GPCRs).

HitHunter cAMP Assay EFC technology was a patent technology of Discover X, the principle was to divide β-galactosidase (β-gal) into two fragments, the enzyme donor (ED) and the enzyme acceptor (EA), each of which was inactive when separated, but they could rapidly complement each other and form active β-gal enzymes in solution to generate signals.

In this test, the intracellular cAMP and ED-cAMP (ED-labeled cAMP) were bound to cAMP antibody (Ab), ED-cAMP-Ab could not complement EA, but ED-cAMP could complement EA to form an active enzyme, which generated a luminescence signal. The amount of signal produced was directly proportional to the amount of cAMP in the cell.

The MOR receptor was bound to the inhibitory Gαi protein, so forskolin (for inducing cAMP signal) was used to induce cAMP expression in the experiment, and the inhibitory effect of the compounds on the above induction was measured.

1.2 Preparation of the Compounds

The compounds H01-H$_{33}$, morphine, and endorphin (used as a reference drug in this experiment) used in this experiment were dissolved in DMSO and prepared into a 1 mM mother solution. And the following working solutions were prepared: starting from the highest concentration of 4 uM, diluted 3 times, with a total of 10 concentration gradients, and the working solution concentration range was 0.000232-4 uM.

1.3 Cell Culturing and Preparation

The cAMP Hunter cell line (HEK293, DiscoverX) was removed from the freezer and expanded according to the Cell Standard Operating Procedure (SOP), 20 μL was collected and inoculated into a 384-well microplate and incubated at 37° C. overnight.

1.4 Experimental Process

The HitHunter cAMP Assay test kit (DiscoverX, 90-0075sm) was used, the kit contained cAMP buffer, cAMP detection solution, and cAMP working solution A.

The cell medium was replaced by 15 μL of cAMP buffer (ingredient: 10 ul of HBSS/10 mM Hepes solution, 5 ul of cAMP Ab reagent (antibody, for binding cAMP)). 5 μL of working solution of the compound solution or morphine solution or endorphin solution (containing 20 uM forskolin (DiscoverX, 92-0005)) was added and incubated at 37° C. for 60 minutes. 20 μL of cAMP detection solution (ingredient: CAMPXS+ED/CL (containing ED fragment for labeling cAMP)) was added and incubated for 1 hour, and finally 20 μL of cAMP working solution A (ingredient: CAMPXS+ EA (EA fragment, for binding ED-cAMP and generating signals)) was added and incubated for 3 hours, and the chemiluminescence signal was measured by PerkinElmer Envision™ instrument.

This experiment was set up with multiple holes.

1.5 Data Processing and Statistical Analysis

The formula was used to calculate the percentage of signal activity per well=100%×(1−(average RLU of the test samples−average RLU of the MAX controls)/(average RLU of the solvent controls−average RLU of the MAX controls)). wherein, the MAX control referred to the fluorescence signal value of the endorphin solution, and the solvent control referred to the fluorescence signal value of DMSO. The DiscoveRx CBIS data analysis workstation (ChemInnovation, CA) was used to perform statistical analysis of the the percentage of signal activity and the concentration of the compounds by the agonist formula (comes with the software, universal) to calculate the EC$_{50}$ value.

2. Test Results and Conclusions

The EC$_{50}$ values of cAMP levels affected by the agonistic effects of the compounds of the invention on MOR are shown in Table 2 below. From the data shown in Table 2, it can be seen that the agonistic activity of the cAMP pathway measured by the compounds of the invention is strong, and its performance is better than that of morphine.

TABLE 2

The EC$_{50}$ values of cAMP levels affected by the agonistic effects of the compounds of the invention on MOR

| Example number | EC50(nM) |
|---|---|
| morphine | 47.2 |
| H01 | 4.93 |
| H02 | 4.06 |
| H03 | 4.36 |
| H04 | 4.36 |
| H05 | 10.2 |
| H06 | 11.8 |
| H07 | 3.08 |
| H08 | 4.77 |
| H09 | 8.45 |
| H10 | 2.89 |
| H11 | 7.31 |
| H12 | 5.51 |
| H13 | 9.43 |
| H14 | 15.85 |
| H15 | 4.28 |
| H16 | 1.36 |
| H17 | 1.89 |
| H18 | 2.35 |
| H19 | 18.58 |
| H20 | 19.85 |
| H21 | 2.57 |
| H22 | 11.89 |
| H23 | 9.73 |
| H24 | 3.74 |
| H25 | 12.78 |
| H26 | 6.95 |
| H27 | 11.96 |
| H28 | 14.21 |
| H29 | 10.45 |
| H30 | 17.36 |
| H31 | 8.73 |
| H32 | 13.45 |
| H33 | 12.04 |

Experiment 3. Test of the Activity of the Compounds of the Invention on β-arrestin Signaling Pathway of MOR

1. Purpose and Method of the Experiment

The purpose of this experiment was to test the activity of the compounds of the invention on the β-arrestin signaling pathway of MOR.

1.1 Experimental Principles and Techniques

In this experiment, the level of cell β-arrestin was measured by enzyme fragment complementation technology (PathHunter β-arrestin GPCR test) of DiscoverX. GPCR activation after ligand binding resulted in the recruitment of β-arrestin to the receptor, and the signal detection was obtained by enzyme fragment complementation (EFC) technology to detect β-arrestin to measure the activation status of GPCR.

The PathHunter β-arrestin GPCR test divided the b-galactosidase (b-gal) enzyme into two fragments, namely the enzyme donor (ED) and the enzyme acceptor (EA), these fragments were inactive when they were independent, and in solution they could come together and complement each other to form an active b-gal enzyme and thus generated signal.

1.2 Preparation of the Compounds

The compounds H01-H$_{33}$, morphine, and endorphin (the reference drug in this experiment) used in this experiment were dissolved in DMSO and prepared into a 1 mM mother solution. And the following working solutions were prepared: starting from the highest concentration of 5 uM, diluted with 3 times, with a total of 10 concentration gradients, and the concentration range was 0.00029-5 um.

1.3 Culturing and Preparation of Cells

According to standard operating procedures (SOP), the PathHunter cell line (HEK293, DiscoverX) was removed from the freezer, amplified, and inoculated into a 384-well microplate at a volume of 20 μL and incubated at 37° C. for 60 mins. 5 μL of the working solution of the compound or morphine or endorphin was added into the wells of the above microplate, and incubated at 37° C. or room temperature for 180 minutes.

1.4 Signal Detection

A PathHunter detection kit (DiscoverX, 93-0001) was used.

The PathHunter detection reagent was added into the cell plate containing the compound or morphine or endorphin according to the recommendation of the kit supplier, and the test signal was generated by incubating at room temperature for 1 hour. The chemiluminescence signal was detected by a PerkinElmer Envision™ instrument. Activity calculation formula: the percentage of activity=100%×(average RLU of the test samples−average RLU of the solvent controls)/(average RLU of the MAX controls−average RLU of the solvent controls)) The MAX control was the value of the fluorescence signal generated by endorphin. The calculated percentage of activity was represented by the Max response (Emax).

2. Test Results and Conclusions

The EC$_{50}$ of the β-arrestin signaling pathway activity affected by the agonistic effects of the compounds of the present invention on MOR receptors was shown in Table 2 below. As can be seen from the data shown in Table 2 below, the activity of the β-arrestin signaling pathway measured by the compounds of the present invention is weaker, and better than that of morphine.

TABLE 3

The EC$_{50}$ of the β-arrestin signaling pathway activity affected by the agonisitic effects of the compounds of the present invention on MOR receptors

| Example number | EC$_{50}$(nM) | Emax (%) |
| --- | --- | --- |
| morphine | 0.33 | 30.48 |
| H01 | >10 | 6.259 |
| H02 | >10 | 0.14 |
| H03 | >10 | 3.185 |
| H04 | >10 | 6.12 |
| H05 | >10 | 0 |
| H06 | >10 | 0.66 |
| H07 | >10 | 1.55 |
| H08 | >10 | 3.80 |
| H09 | >10 | 3.28 |
| H10 | >10 | 3.7 |
| H11 | >10 | 2.28 |
| H12 | >10 | 32.21 |

TABLE 3-continued

The EC$_{50}$ of the β-arrestin signaling pathway activity affected by the agonisitic effects of the compounds of the present invention on MOR receptors

| Example number | EC$_{50}$(nM) | Emax (%) |
| --- | --- | --- |
| H13 | >10 | 3.41 |
| H14 | >10 | 1.82 |
| H15 | >10 | 15.78 |
| H16 | >10 | 3.12 |
| H17 | >10 | 1.78 |
| H18 | >10 | 0.48 |
| H19 | >10 | 1.12 |
| H20 | >10 | 2.12 |
| H21 | >10 | 0.08 |
| H22 | >10 | 2.31 |
| H23 | >10 | 2.20 |
| H24 | >10 | 2.76 |
| H25 | >10 | 3.20 |
| H26 | >10 | 22.56 |
| H27 | >10 | 3.32 |
| H28 | >10 | 6.26 |
| H29 | >10 | 7.07 |
| H30 | >10 | 2.91 |
| H31 | >10 | 5.06 |
| H32 | >10 | 11.68 |
| H33 | >10 | 8.69 |

Experiment 4: Test of the Effect of the Compounds on Rat Surgical Incision Injury Model

1. Abstract 8-week-old male SD rats weighing 200 g-300 g were used as experimental animals to determine the effect of the compound of Example H02, the compound of Example H04, the compound of Example H10, the compound of Example H16, the compound of Example H17, the compound of Example H18, the compound of Example H21 and the compound of Example H24 on surgical pain in rats after intravenous administration. The analgesic effect of the compounds was discussed.

2. Experimental Scheme

2.1 Experimental Compounds

The compound of Example H02, the compound of Example H04, the compound of Example H10, the compound of Example H16, the compound of Example H17, the compound of Example H18, the compound of Example H21 and the compound of Example H24.

2.2 Preparation of the Compounds

A certain amount of the compounds or TRV130 (MCE, 15150) was weighed, and dissolved in ethanol/castor oil/water=10/10/80 as a clear and transparent solution.

2.3 Operation

2.3.1 Experimental Process

Three days after the rats were acclimatized to the experimental environment, the preoperative base value was determined, and followed by the surgical pain operation described below, about 24 hours after the surgery, the basic value was measured before administration on all animals, and mechanically hypersensitive animals (the paw withdrawal threshold (PWT) was less than 5 g) was randomly assigned to each administration group according to PWT. The pain threshold was determined 30 minutes and 60 minutes after intravenous administration of the positive drug TRV130 or each compound of the present invention (at a dose of 0.3 mg/kg).

2.3.2 Surgical Pain Operation

The surgical procedure was performed aseptically, and the surgical instruments (scissors, tweezers, scalpels, surgical cotton and sutures) were sterilized before surgery. The animals were anesthetized with sodium pentobarbital (50 mg/kg, injected intraperitoneally), and the toes of the animals were squeezed to confirm that the animals were completely anesthetized before surgery. From the position of 0.5 cm away from the heel, an incision about 1 cm was made in the longitudinal direction of the toe. After cutting the skin, the musculus flexor digitorum brevis was raised and a blunt injury was caused longitudinally. After pressing to stop bleeding, the wound was sutured. When the animal was completely awake (free to move), the animal was put back into the cage (the reference of the construction of surgical pain model: Timothy J. Brennan, Erik P. Vandermeulen, G. F. Gebhart. Characterization of a rat model of incisional pain. Pain, 64(1996):493-501).

2.3.3 Determination of Pain Threshold

An up-down method was used for the determination of pain sensitivity. The mechanical pain results were expressed as animal paw withdrawal response threshold (PWT). The rat was placed separately in a plexiglass box with a mesh at the bottom of the box to ensure that the rat's feet could be tested. The rat was acclimatized for 15 minutes before the test, and after the acclimatization, the test fiber (von frey fiber, West coast) was used to test in the middle part of the hind foot of the rat. The test fibers included 8 test strengths: 3.61 (0.4 g), 3.84 (0.6 g), 4.08 (1 g), 4.31 (2 g), 4.56 (4 g), 4.74 (6 g), 4.93 (8 g), and 5.18 (15 g). During the test, the test fiber was pressed vertically against the skin and a force was applied to bend the fiber for 6-8 seconds, at an interval of 5 seconds between each test. During the test, the animal's rapid withdrawal was recorded as a pain response. When the test fiber left the animal's skin, the animal's withdrawal was also recorded as a pain response. Starting from 2 g, depending on whether the rats had any pain response, the test was changed into the next test intensity or the previous test intensity. A series of responses of the rats to different test intensities were recorded. If the rat had a pain reaction, it was indicated by "X", if there was no pain reaction, it was indicated by "O", and a series of "O" or "X" combinations could be obtained, and the "O" prior to the occurance of "X" was taking as the starting point, 6 consecutive stimulation responses including the starting point were selected, such as "OXOXOO", as the key sequence for estimating the 50% paw withdrawal response threshold, the 50% paw withdrawal response threshold was calculated using the following formula: 50% paw withdrawal response threshold (g)=$10^{(Xf+k\delta)}$/10,000. Wherein, Xf was the logarithmic value of von Frey fiber used in the last test, and K value was the animal withdrawal reaction mode (recorded during the test), which was the value obtained after looking up the table according to the obtained sequence of "X" and "O", $\delta$=Mean of logarithmic difference between von Frey fibers used in the test.

2.4 Experimental Results and Conclusions

The test results of the efficacy of the compounds of the present invention on the surgical pain of rats are shown in Table 4 below. From the data shown in Table 4 below, it can be seen that 0.5 hour and 1 hour after the administration at a dose of 0.3 mg/kg, the compounds of the present invention can inhibit mechanical hypersensitivity to pain induced by postoperative pain model in rats, and the effect is better than that of the positive drug TRV130. Experimental results show that the compounds of the present invention have good analgesic effect and long duration of efficacy.

TABLE 4

Efficacy test of the compounds of the invention on surgical pain in rats

| | | 50% PWT(g) | | |
| --- | --- | --- | --- | --- |
| compound | Dose (mg/kg) | Base value before administration | 30 min after administration | 60 min after administration |
| TRV130 | 0.3 | 4.12 ± 0.23 | 6.05 ± 0.44 | 5.71 ± 0.33 |
| H02 | 0.3 | 4.30 ± 0.21 | 9.62 ± 1.91 | 7.92 ± 1.37 |
| H04 | 0.3 | 4.31 ± 0.22 | 11.72 ± 0.56 | 8.29 ± 1.06 |
| H10 | 0.3 | 4.24 ± 0.25 | 8.05 ± 0.24 | 7.59 ± 1.02 |
| H16 | 0.3 | 4.32 ± 0.20 | 13.72 ± 0.56 | 10.29 ± 1.06 |
| H17 | 0.3 | 4.32 ± 0.21 | 8.85 ± 1.59 | 7.91 ± 1.43 |
| H18 | 0.3 | 4.24 ± 0.26 | 7.85 ± 0.54 | 6.91 ± 0.33 |
| H21 | 0.3 | 4.20 ± 0.24 | 10.72 ± 2.56 | 8.29 ± 1.06 |
| H24 | 0.3 | 4.26 ± 0.28 | 11.32 ± 2.35 | 7.29 ± 1.23 |

Experiment 5: Effects of the Compounds on Respiratory Depression in Rats

1. Abstract 8-week-old male SD rats weighing 200 g-300 g were used as experimental animals to determine the effect of the compound of Example H05, the compound of Example H08, the compound of Example H10, the compound of Example H16, the compound of Example H17, the compound of Example H18, the compound of Example H21, and the compound of Example H24 on the partial pressure of blood in rats after intravenous administration. The effects of the compounds of the invention on respiratory depression were investigated.

2. Experimental Scheme

2.1 Experimental Compounds

The compound of Example H05, the compound of Example H08, the compound of Example H10, the compound of Example H16, the compound of Example H17, the compound of Example H18, the compound of Example H21, and the compound of Example H24

2.2 Preparation of the Compounds

A certain amount of the compounds or morphine was weighed, and dissolved in ethanol/castor oil/water=10/10/80 as a clear and transparent solution.

2.3 Operation

After the rats were acclimatized to the experimental environment for 3 days, each animal was anesthetized with sodium pentobarbital (50-60 mg/kg, ip), and then the right common carotid artery was isolated and the unilateral carotid artery tube-bury surgery was performed (PE60, ID*OD*length as 0.76 mm*1.22 mm*20 cm, buried into the artery 1 cm deep, and the tube was filled with heparin sodium tube sealing solution). The rats were recovered for 1 day after surgery, after weighing, each compound of the present invention or morphine was administered intravenously in a single dose at the effective dose of the surgical pain, and 0.4-0.5 mL of arterial blood was taken through the buried tube at 5 min, 30 min, 60 min, and 120 min before and after administration respectively, and the pH, carbon dioxide partial pressure ($PCO_2$) and oxygen partial pressure ($PO_2$) of the blood were measured using a blood-gas analyzer (Radiometer Medical ApS, ABL90FLEX) immediately.

2.4 Experimental Results and Conclusions

The partial pressure of carbon dioxide measured at each time point before and after administration of the compounds of the present invention and morphine is shown in Table 5 below. As can be seen from Table 5 below, the compounds of the present invention have a weaker respiratory depression effect at a pharmacologically effective dose.

pound of Example H07, the compound of Example H16, the compound of Example H17, the compound of Example H18, the compound of Example H21, and the compound of Example H24 were determined.

2.2 Preparation of the Compounds

A certain amount of the compounds were weighed, and dissolved in ethanol/castor oil/water=10/10/80 to form a uniform solution.

2.3 Collection and Treatment of Plasma

The above compounds were administered intravenously to rats at a dose of 1 mg/kg, and 0.2 ml of blood was collected from the orbit at 0.083, 0.25, 0.5, 1.0, 2.0, 4.0, 6.0, 8.0, 12.0, 24.0 hours before and after administration, and placed in an anticoagulant tube, the plasma was separated by centrifugation at 6,000 rpm for 10 minutes at 4° C., and stored at −80° C.

50 μL of plasma was taken at different times, 150 μL of acetonitrile solution containing internal standard tolbutamide (200 ng/mL) was added, the system was mixed and shaked for 5 minutes, 12000 rpm, centrifuged for 5 minutes, 100 μL of supernatant was removed, and then mixed with

TABLE 5

Test of the effect of the compound of the invention on respiratory inhibition in rats

| compound | Dose (mg/kg) | $PCO_2$(mmHg) | | | | |
|---|---|---|---|---|---|---|
| | | 5 min before administration | 5 min after administration | 30 min after administration | 60 min after administration | 120 min after administration |
| morphine | 24 | 36.41 ± 0.98 | 37.26 ± 1.18 | 40.94 ± 2.78 | 58.63 ± 3.53 | 56.9 ± 4.05 |
| H05 | 0.3 | 35.65 ± 0.44 | 36.15 ± 1.93 | 33.65 ± 0.95 | 34.85 ± 0.43 | 35.7 ± 0.95 |
| H08 | 0.3 | 33.77 ± 0.88 | 35.48 ± 1.54 | 34.03 ± 0.69 | 34.27 ± 1.4 | 34.83 ± 1.15 |
| H10 | 0.3 | 35.72 ± 1.88 | 37.48 ± 1.94 | 35.03 ± 1.89 | 36.27 ± 1.67 | 36.83 ± 1.85 |
| H16 | 0.3 | 35.27 ± 0.43 | 30.48 ± 1.24 | 30.03 ± 0.62 | 31.27 ± 1.2 | 31.83 ± 1.40 |
| H17 | 0.3 | 34.77 ± 1.88 | 35.48 ± 1.74 | 34.03 ± 1.69 | 34.27 ± 1.4 | 34.83 ± 1.15 |
| H18 | 0.3 | 33.77 ± 0.88 | 35.48 ± 1.54 | 34.03 ± 0.69 | 36.27 ± 1.4 | 34.83 ± 1.45 |
| H21 | 0.3 | 36.77 ± 1.78 | 35.48 ± 1.72 | 36.03 ± 1.42 | 37.27 ± 1.94 | 36.83 ± 1.65 |
| H24 | 0.3 | 36.77 ± 1.94 | 36.48 ± 1.80 | 33.03 ± 0.72 | 36.27 ± 1.57 | 36.83 ± 1.73 |

Experiment 6. Pharmacokinetic Test of the Compounds of the Invention

1. Abstract 8-week-old male SD rats weighing 200-300 g were used as experimental animals, and LC/MS/MS method was used to determine the drug concentration in plasma at different times after the administration of the compound of Example H01, the compound of Example H04, the compound of Example H05, the compound of Example H07, the compound of Example H16, the compound of Example H17, the compound of Example H18, the compound of Example H21, and the compound of Example H24. The pharmacokinetic behavior of the compounds of the present invention in rats was studied, and its pharmacokinetic characteristics were evaluated.

2. Experimental Scheme 2.1 Experimental Compounds

The compound of Example H01, the compound of Example H04, the compound of Example H05, the com- 200 μL of water, then the sample was loaded for analysis. The internal standard tolbutamide solid (Aladdin, T129578) powder was dissolved in DMSO to prepare into a 1 mg/mL stock solution. The stock solution was diluted with 100% acetonitrile to obtain a solution of 200 ng/mL as a protein precipitator.

2.4 Chromatographic Conditions and Analysis Software

The liquid chromatography system was an LC-20AD UFLC high performance liquid chromatography system (Shimadzu, LC-20AD). The mass spectrometry system was an AB Sciex API4000 triple quadrupole mass spectrometer equipped with an electrospray ionization source (ESI) (Applied Biosystems, Canada). The software used to control the liquid-mass coanalyzer and quantitative analysis was Analyst 1.6 (Applied Biosystems, Canada), and the pharmacokinetic parameters were analyzed using WinNonlin (version 5.2, Pharsight, Mountain View, Calif.) non-compartment model.

Liquid chromatographic separation was performed using AQ-$C_{18}$ column (50×2.1 mm, internal diameter of 5 m). The column temperature was maintained at room temperature. The composition and gradient of the mobile phase are shown in table 6 below.

TABLE 6

Liquid phase conditions of the compounds

| time (min) | flow rate (mL/min) | A (%) (water with 0.1% formic acid, v/v) | B (%) (acetonitrile with 0.1% formic acid, v/v) |
| --- | --- | --- | --- |
| initial | 1.0 | 80 | 20 |
| 1.00 | 1.0 | 20 | 80 |
| 1.50 | 1.0 | 20 | 80 |
| 1.60 | 1.0 | 80 | 20 |
| 3.00 | 1.0 | 80 | 20 |

The mass spectrum conditions of the compounds to be measured and the internal standard are shown in table 7 below.

TABLE 7

Mass spectrometry conditions

| compound | scanning mode | ionization mode | Parent ions/ daughter ions |
| --- | --- | --- | --- |
| compound | MRM | electro spray: positive | 400.2/245.2 |
| internal standard (tolbutamide) | MRM | electro spray: positive | 271.1/154.8 |

2.5 Preparation of the Standard and Quality Control Solutions

The compound to be tested was dissolved in DMSO to prepare a stock solution with a concentration of 1 mg/mL, and diluted with 70% acetonitrile to obtain a series of standard working solutions with concentrations of 30, 10, 3, 1, 0.3, 0.1, 0.03, and 0.01. μg/mL, and a series of standard quality control solutions (24, 8 and 0.03 μg/mL). 5 μL of standard solution and 45 μL of blank plasma matrix were mixed uniformity to obtain standard solutions (3000, 1000, 300, 100, 30, 10, 3, and 1 ng/mL) and quality control standards (plasma samples: 2400, 800, 80, and 3 ng/mL) at each concentration point of the standard curve.

The solid powder of internal standard tolbutamide was dissolved in DMSO to prepare a 1 mg/mL stock solution. The stock solution was diluted with 100% acetonitrile to obtain a solution of 200 ng/mL as a protein precipitator.

2.6 Experimental Results

The pharmacokinetic parameters after administration of the compounds of the present invention are shown in Table 6 below. It can be seen from the data shown in table 6 that the compounds of the invention have better pharmacokinetic absorption and have better pharmacokinetic characteristics.

TABLE 6

Pharmacokinetic parameters of the compounds of the invention

| | Dose (1 mg/kg) | | |
| --- | --- | --- | --- |
| compound | plasma concentration (Cmax, g/ml) | curve area (AUC, g/ml · h) | half life (T½, h) |
| H01 | 201.50 ± 33.50 | 295.00 ± 1.00 | 1.11 ± 0.24 |
| H04 | 378.50 ± 17.50 | 494.00 ± 34.00 | 2.92 ± 0.02 |
| H05 | 261.00 ± 21.00 | 336.50 ± 14.10 | 3.93 ± 0.13 |
| H07 | 483.33 ± 33.33 | 582.83 ± 31.83 | 1.25 ± 0.05 |
| H16 | 820.50 ± 37.50 | 1194.00 ± 54.00 | 5.3 ± 0.02 |
| H17 | 388.33 ± 23.33 | 482.13 ± 31.83 | 1.45 ± 0.15 |
| H18 | 483.24 ± 23.34 | 582.03 ± 11.83 | 3.45 ± 0.55 |
| H21 | 283.42 ± 13.33 | 382.13 ± 10.83 | 2.05 ± 0.25 |
| H24 | 583.21 ± 23.33 | 682.13 ± 21.03 | 3.05 ± 0.15 |

Experiment 7. Acute Toxicity Test of the Compounds of the Invention

1. Abstract 8-week-old ICR mice (half male and half female) weighing 200-220 g were used as experimental animals, the compound of Example H10, the compound of Example H16, the compound of Example H17, the compound of Example H21, and the compound of Example H24 were injected intravenously, and administered once, the mice were continuously observed for 14 days, including clinical observation, weight and pathological examination.

2. Experimental Scheme

2.1 Experimental Compounds

The compound of Example H10, the compound of Example H16, the compound of Example H17, the compound of Example H21, and the compound of Example H24 were determined.

2.2 The Preparation of the Compounds

A certain amount of the compounds were weighed, and dissolved in ethanol/castor oil/water=10/10/80 to prepare a uniform solution.

2.3 Operation

The acute toxicity of mice after the single intravenous administration of the compounds of examples was observed using the up-down method, with 10 mice in each dose group, half male and half female. The doses of administration were 10 mg/kg, 15 mg/kg, 20 mg/kg, 25 mg/kg, 35 mg/kg, and the volume of administration was 10 ml/kg, the compound was prepared to be a clear and transparent solution using the above solvent and then injected intravenously.

2.4 Experimental Statistics

Based on the mortality of the animals at each dose, Bliss software was used to calculate the half-lethal dose ($LD_{50}$).

2.5 Experimental Results and Conclusions

At least 80% of the animals died at the highest dose and at most 20% of the animals died at the lowest dose.

All animals were observed for 14 consecutive days after administration and all the animals did not show other abnormal manifestations. The weight of the administered animals in each group decreased slightly on the second day of administration, but the difference was not significant compared to the control group. After the 14-day observation period, all animals were euthanized, and gross anatomical examination was performed. There were no obvious abnormalities on the body surface, and no visible lesions in the chest, abdominal cavity, pelvic cavity and cranial cavity.

Under the experimental conditions, the LD$_{50}$ value of the compounds of the present invention after intravenous administration was between 20-30 mg/kg. And the security was better.

The invention claimed is:

1. A compound represented by the general formula I, and stereoisomers, tautomers, enantiomers, diastereomers, racemates, and pharmaceutically acceptable salts thereof,

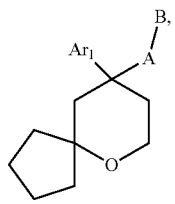

I wherein,
A is a —C$_{1-2}$ alkylene;
B is —NH—CH$_2$—Ar$_2$, wherein
Ar$_1$ is

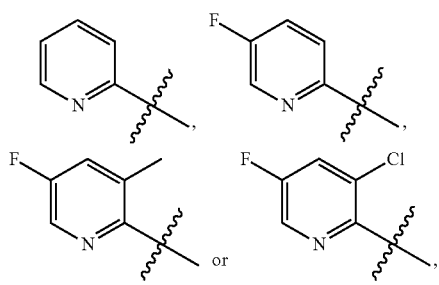

Ar$_2$ is

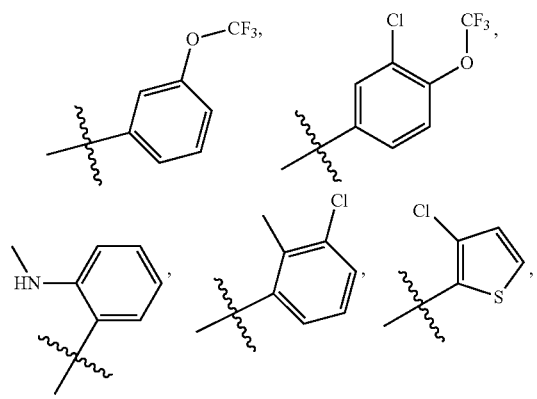

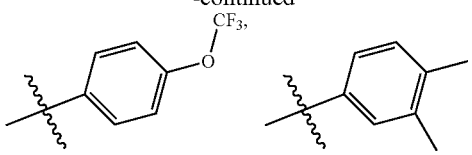

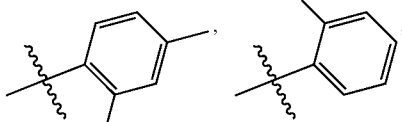

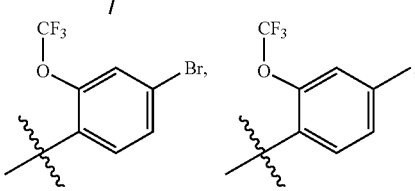

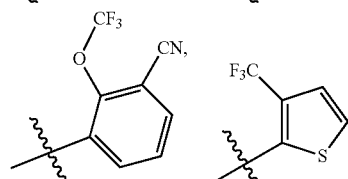

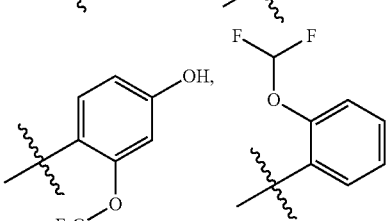

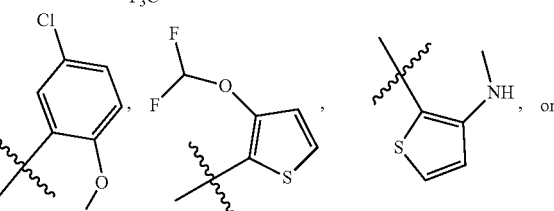

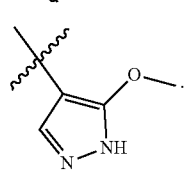

2. A compound according to claim 1 or stereoisomers, tautomers, enantiomers, diastereomers, racemates, and pharmaceutically acceptable salts thereof, the compound is:
(3-trifluoromethoxybenzyl)-[2-(9-(pyridin-2-yl)-6-oxaspiro[4.5]decan-9-yl)ethyl]amine; (2-chloro-4-trifluoromethoxybenzyl)42-(9-(pyridin-2-yl)-6-oxaspiro[4.5]decan-9-yl)ethyl]amine;
N-methyl-2-(((2-(9-(pyridin-2-yl)-6-oxaspiro[4.5]decan-9-yl)ethyl)amino)methyl)aniline;
(3-chloro-2-methylbenzyl)-[2-(9-(pyridin-2-yl)-6-oxaspiro[4.5]decan-9-yl)ethyl]amine;
((3-chloro-thiophen-2-methyl)-[2-(9-(pyridin-2-yl)-6-oxaspiro[4.5]decan-9-yl)ethyl]amine;
(4-trifluoromethoxybenzyl)-[2-(9-(pyridin-2-yl)-6-oxaspiro[4.5]decan-9-ethyl]amine;

(3,4-dimethylbenzyl)-[2-(9-(pyridin-2-yl)-6-oxaspiro[4.5]decan-9-yl)ethyl]amine;

(2,4-dimethylbenzyl)-[2-(9-(pyridin-2-yl)-6-oxaspiro[4.5]decan-9-yl)ethyl]amine;

(2-trifluoromethoxybenzyl)42-(9-(3-chloro-5-fluoropyridin-2-yl)-6-oxaspiro[4.5]decan-9-yl)ethyl]amine;

(2-trifluoromethoxybenzyl)42-(9-(3-methyl-5-fluoropyridin-2-yl)-6-oxaspiro[4.5]decan-9-yl)ethyl]amine;

(4-bromo-2-trifluoromethoxybenzyl)42-(9-(pyridin-2-yl)-6-oxaspiro[4.5]decan-9-yl)ethyl]amine;

(4-methyl-2-trifluoromethoxybenzyl)42-(9-(pyridin-2-yl)-6-oxaspiro[4.5]decan-9-yl)ethyl]amine;

3-{[(2-(9-(pyridin-2-yl)-6-oxaspiro[4.5]decan-9-yl)ethyl]aminomethyl}-2-trifluoromethoxylbenzonitrile;

((3-trifluoromethylthiophen-2-yl)methyl)42-(9-(pyridin-2-yl)-6-oxaspiro[4.5]decan-9-yl)ethyl]amine;

4-{[2-(9-(pyridin-2-yl)-6-oxaspiro[4.5]decan-9-yl)ethyl-amine]methyl-3-trifluoromethoxphenol;

(2-difluoromethoxybenzyl)42-(9-(pyridin-2-yl)-6-oxaspiro[4.5]decan-9-ethyl]amine;

(5-chloro-2-trifluoromethoxybenzyl)42-(9-(pyridin-2-yl)-6-oxaspiro[4.5]decan-9-yl)ethyl]amine;

((3-difluoromethoxythiophen-2-yl)methyl)42-(9-(pyridin-2-yl)-6-oxaspiro[4.5]decan-9-yl)ethyl]amine;

{249-(5-fluoro-pyridin-2-yl)-6-oxa-spiro[4.5]decan-9-A-ethyl-(2-(trifluoromethoxy)-benzyl)-amine;

(2-trifluoromethoxybenzyl)-[2-(9-pyridin-2-yl-6-oxa-spiro[4.5]decan-9-yl)-ethyl]-amine;

[(5-methoxy-1 [(5-methoxy-1H-pyrazol-4-yl)methyl]-[2-(9-(pyridin-2-yl)-6-oxaspiro[4.5]decan-9-yl)ethyl]amine;

(3-bromo-2-trifluoromethoxybenzyl)42-(9-pyridin-2-yl-6-oxa-spiro[4.5]decan-9-yl)-ethylamine;

{2-(5-fluoro-pyridin-2-yl)-6-oxa-spiro[4.5]decan-9-yl]-ethyl-(2-(difluoromethoxy)-benzyl)-amine;

{2-(5-fluoro-pyridin-2-yl)-6-oxa-spiro[4.5]decan-9-yl)ethyl((3-chlorothiophene-2-yl)-methyl)-amine;

{2-[9-(5-fluoro-pyridin-2-yl)-6-oxa-spiro[4.5]decan-9-A-ethyl-(3,4-dimethyl-benzyl)-amine;

{249-(5-fluoro-pyridin-2-yl)-6-oxa-spiro[4.5]decan-9-yl]-ethyl-(3-chloro-2-methyl-benzyl)-amine; or {2-[9-(5-fluoro-pyridin-2-yl)-6-oxa-spiro[4.5]decan-9-A-ethyl-((3-difluoromethoxythiophen-2-yl)-methyl)-amine.

3. A pharmaceutical composition, characterized by including a therapeutically effective amount of the compound according to claim 1 or stereoisomers, tautomers, enantiomers, diastereomers, racemates, and pharmaceutically acceptable salts thereof, and optionally one or more of the medically acceptable carriers and/or additives, the carriers such as saline, hot-pressed water, Ringer solution, buffered saline, glucose, maltodextrin, glycerol, ethanol, and mixtures thereof; the additives such as diluents, lubricants, adhesives, glidants, disintegrants, sweeteners, flavoring agents, wetting agents, dispersants, surfactants, buffered saline, coating agents, foaming agents, preservatives, stabilizers or fragrances.

4. A method for preparing a compound as defined in claim 1, wherein when A is a —C$_{1-2}$ alkylene, and B is —NH—CH$_2$—Ar$_2$, the synthesis route is as shown in Scheme 1:

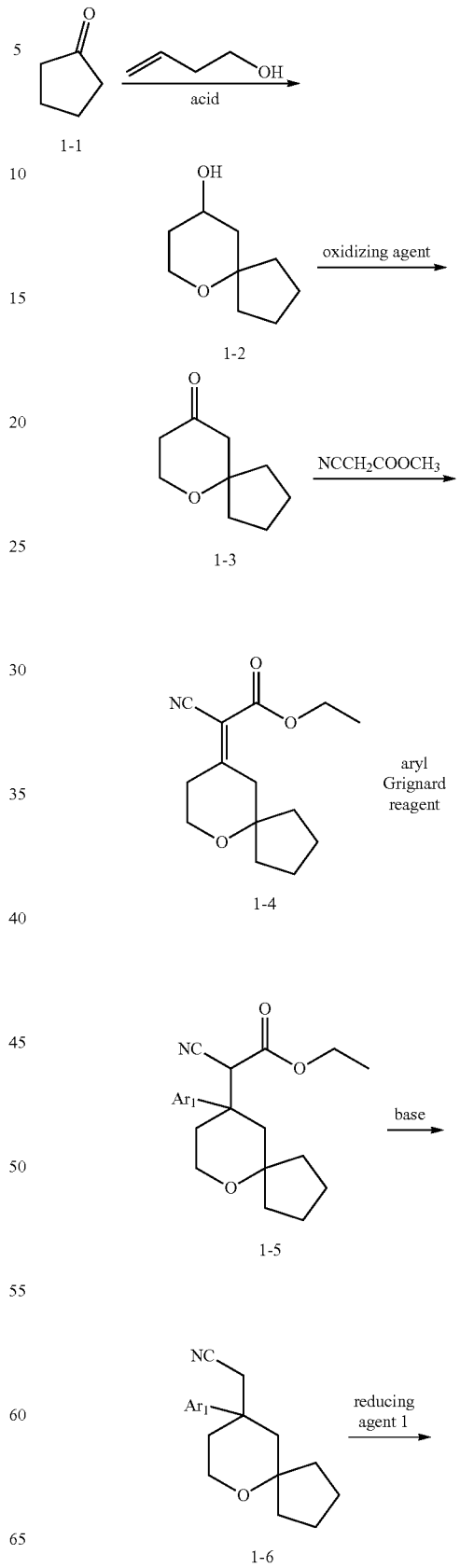

-continued
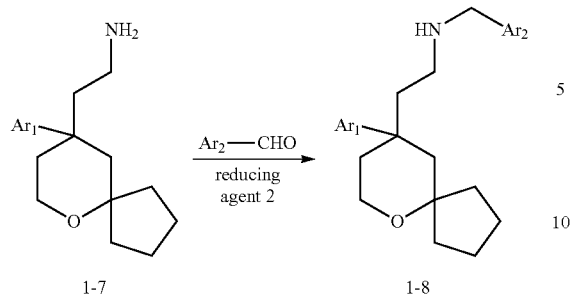
wherein Ar1 and Ar2 are as defined in claim 1,
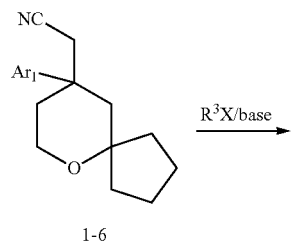
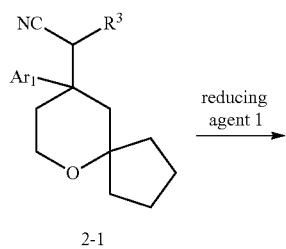
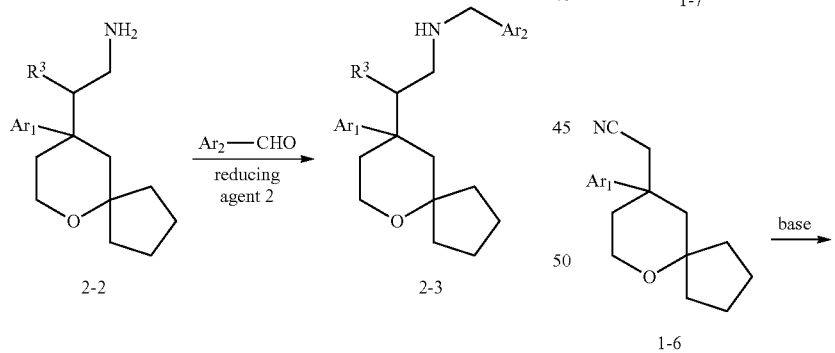
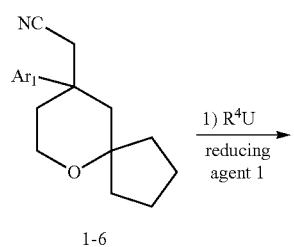
-continued
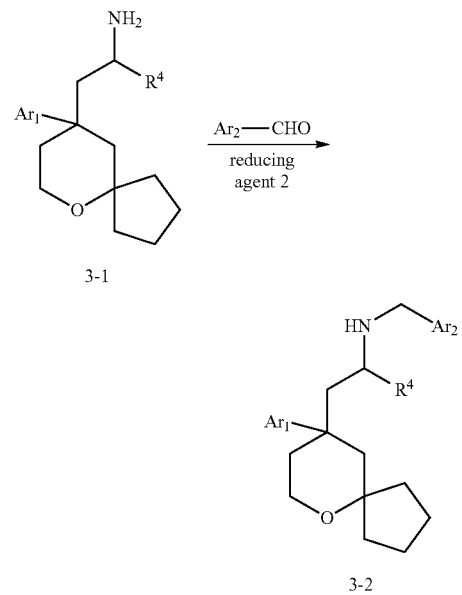
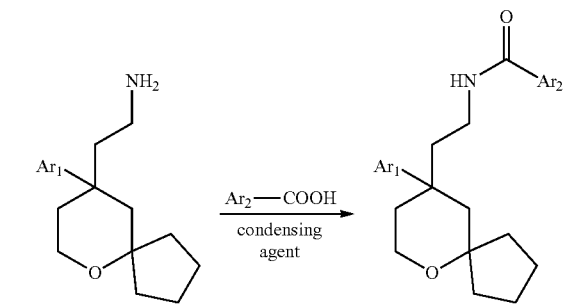
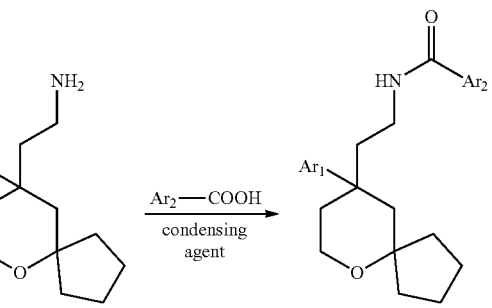
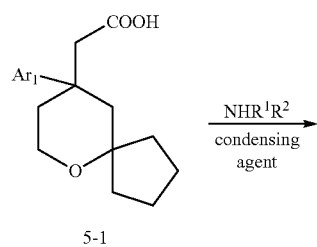

-continued

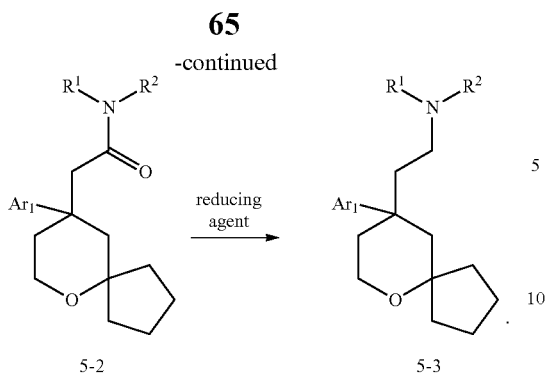

5-2     5-3

5. The method according to claim 4, wherein in the Scheme 1, the acid is sulfuric acid, hydrochloric acid, phosphoric acid, trifluoromethanesulfonic acid, hydrobromic acid or a combination thereof; the oxidizing agent is pyridinium chlorochromate (PCC), pyridinium dichromate (PDC), or a combination thereof;

the aryl Grignard reagent is aryl magnesium bromide, aryl magnesium chloride, or a combination thereof; the base is potassium hydroxide, sodium hydroxide or a combination thereof; the reducing agent 1 is lithium aluminum tetrahydride, borane tetrahydrofuran, borane dimethyl sulfide or a combination thereof; and the reducing agent 2 is sodium borohydride, potassium borohydride, sodium triacetoxyborohydride, sodium cyanoborohydride or a combination thereof.

* * * * *